US008664274B2

(12) United States Patent
Dai et al.

(10) Patent No.: US 8,664,274 B2
(45) Date of Patent: Mar. 4, 2014

(54) SULFONYL SEMICARBAZIDES, SEMICARBAZIDES AND UREAS, PHARMACEUTICAL COMPOSITIONS THEREOF, AND METHODS FOR TREATING HEMORRHAGIC FEVER VIRUSES, INCLUDING INFECTIONS ASSOCIATED WITH ARENA VIRUSES

(75) Inventors: Dongcheng Dai, Corvallis, OR (US); Tove Bolken, N. Keizer, OR (US); Dennis E. Hruby, Albany, OR (US); Thomas R. Bailey, Phoenixville, PA (US)

(73) Assignee: Siga Technologies, Inc., New York, NY (US)

( * ) Notice: Subject to any disclaimer, the term of this patent is extended or adjusted under 35 U.S.C. 154(b) by 294 days.

(21) Appl. No.: 13/176,866

(22) Filed: Jul. 6, 2011

(65) Prior Publication Data

US 2013/0261087 A1 Oct. 3, 2013

Related U.S. Application Data

(60) Division of application No. 11/653,972, filed on Jan. 17, 2007, now Pat. No. 7,994,221, which is a continuation-in-part of application No. PCT/US2005/043931, filed on Dec. 6, 2005.

(60) Provisional application No. 60/632,990, filed on Dec. 6, 2004.

(51) Int. Cl.
*A61K 31/166* (2006.01)
*C07C 233/64* (2006.01)

(52) U.S. Cl.
USPC ........... 514/615; 564/123; 564/161; 564/183; 514/613

(58) Field of Classification Search
USPC ................... 564/123, 161, 183; 514/613, 615
See application file for complete search history.

(56) References Cited

U.S. PATENT DOCUMENTS

| | | | | |
|---|---|---|---|---|
| 5,182,303 | A | 1/1993 | Daub et al. | |
| 5,194,084 | A | 3/1993 | Findeisen et al. | |
| 5,274,098 | A | 12/1993 | Werner | |
| 5,625,073 | A | 4/1997 | Lindig et al. | |
| 5,869,681 | A | 2/1999 | Muller et al. | |
| 5,904,857 | A | 5/1999 | Bailey et al. | |
| 6,077,661 | A | 6/2000 | Natarajan et al. | |
| 6,524,567 | B2 | 2/2003 | Laub | |
| 7,687,641 | B2 | 3/2010 | Jordan et al. | |
| 7,994,221 | B2 * | 8/2011 | Dai et al. | 514/615 |
| 2003/0186842 | A1 | 10/2003 | Fritz et al. | |
| 2004/0054005 | A1 | 3/2004 | Lan et al. | |
| 2004/0063765 | A1 | 4/2004 | Ammendola et al. | |
| 2004/0077607 | A1 | 4/2004 | Uckun | |
| 2007/0254934 | A1 | 11/2007 | Hruby et al. | |
| 2007/0287735 | A1 | 12/2007 | Jordan et al. | |
| 2008/0004452 | A1 | 1/2008 | Jordan et al. | |
| 2008/0103181 | A9 | 5/2008 | Jordan et al. | |
| 2008/0300265 | A1 | 12/2008 | Hruby et al. | |
| 2009/0036513 | A1 | 2/2009 | Hruby et al. | |
| 2009/0180980 | A1 | 7/2009 | Hruby et al. | |
| 2009/0203675 | A1 | 8/2009 | Deng et al. | |
| 2010/0256096 | A1 | 10/2010 | Dai et al. | |
| 2011/0118505 | A1 | 5/2011 | Dai | |

FOREIGN PATENT DOCUMENTS

| | | | |
|---|---|---|---|
| EP | 0283876 | A2 | 9/1988 |
| EP | 0294666 | A2 | 12/1988 |
| EP | 0398096 | A1 | 11/1990 |
| JP | H05-097793 | | 4/1993 |
| JP | H11-240859 | | 9/1999 |
| JP | 2001-507362 | A | 6/2001 |
| WO | WO9533719 | A1 | 12/1995 |
| WO | WO9834629 | A1 | 8/1998 |
| WO | WO9920272 | A1 | 4/1999 |
| WO | 9933790 | A1 | 7/1999 |
| WO | WO9933790 | A1 | 7/1999 |
| WO | WO03062265 | A2 | 7/2003 |
| WO | WO2004096197 | A2 | 11/2004 |
| WO | WO 2004/112718 | | 12/2004 |
| WO | WO 2005037257 | | 4/2005 |
| WO | 2006062898 | A2 | 6/2006 |
| WO | WO 2006/062898 | | 6/2006 |
| WO | WO 2007/100888 | | 9/2007 |
| WO | WO 2007/103111 | | 9/2007 |
| WO | WO 2007/120374 | | 10/2007 |

(Continued)

OTHER PUBLICATIONS

Borio et al. Hemorrhagic Fever Viruses as Biological Weapons: Medical and Public Health Management, JAMA, 2002, vol. 287 (18) 2391-2405.

(Continued)

*Primary Examiner* — Golam M M Shameem

(74) *Attorney, Agent, or Firm* — Kramer Levin Naftalis & Frankel LLP

(57) ABSTRACT

Compounds, methods and pharmaceutical compositions for treating viral infections, by administering certain novel sulfonyl semicarbazides, carbonyl semicarbazides, semicarbazides, ureas and related compounds in therapeutically effective amounts are disclosed. Methods for preparing the compounds and methods of using the compounds and pharmaceutical compositions thereof are also disclosed. In particular, the treatment and prophylaxis of viral infections such as caused by hemorrhagic fever viruses is disclosed, i.e., including but not limited to, Arenaviridae (Junin, Machupo, Guanarito, Sabia, Lassa, Tacaribe, Pinchinde, and VSV), Filoviridae (ebola and Marburg viruses), Flaviviridae (yellow fever, omsk hemorrhagic fever and Kyasanur Forest disease viruses), and Bunyaviridae (Rift Valley fever).

10 Claims, 6 Drawing Sheets

(56) References Cited

FOREIGN PATENT DOCUMENTS

| | | | |
|---|---|---|---|
| WO | WO 2008079159 | | 7/2008 |
| WO | WO 2008130348 | | 10/2008 |
| WO | WO 2008/147962 | | 12/2008 |
| WO | WO 2008147474 | | 12/2008 |
| WO | WO2008147474 | A2 | 12/2008 |
| WO | 2009029622 | A2 | 3/2009 |
| WO | WO 2009/029622 | | 3/2009 |
| WO | 2009123776 | A2 | 10/2009 |
| WO | WO 2009/123776 | | 10/2009 |
| WO | WO 2009149054 | | 12/2009 |
| WO | WO2012060820 | A1 | 5/2012 |

OTHER PUBLICATIONS

Buchmeier, M.J., Clegg, J.C.S., Franze-Fernandez, M. T., Kolakofsky, D., Peters, C. J., and Southern, P. J., "Virus Taxonomy: Sixth Report of the International Committee on Taxonomy of Viruses," Murphy, F.A., Fauquet, C. M. et al., Eds. Sprnger-Verlag, New York, 319-323 (1995).
Childs, J. E., and Peters, C. J., "The Arenaviridae" Ed Salvato (ed.), Plenum Press, New York, pp. 331-384 (1993).
Office Action Dated Feb. 19, 2010, U.S. Appl. No. 11/712,918, filed Mar. 2, 2007, Inventor Hruby et al.
Office Action Dated Sep. 14, 2009, U.S. Appl. No. 10/561,153, filed Apr. 6, 2006, Inventor Jordan et al.
Office Action Dated May 6, 2009, U.S. Appl. No. 11/785,997, filed Apr. 23, 2007, Inventor Jordan et al.
Supplementary European Search Report EP Application No. 07751990.8, Dated Mar. 18, 2010.
Database Registry, Chemical Abstracts Service, Columbus Ohio, Jan. 2, 2001, XP002612388, Database Accession No. 312503-27-8, Abstract.
Database Registry, Chemical Abstracts Service, Columbus Ohio, Jun. 5, 2001, XP002612389, Database Accession No. 339367-98-5, Abstract.
Database Registry, Chemical Abstracts Service, Columbus Ohio, Jan. 9, 2002, XP002612390, Database Accession No. 381239-42-5, Abstract.
Database Registry, Chemical Abstracts Service, Columbus Ohio, May 6, 2003, XP002612391, Database Accession No. 511240-64-5.
European Search Report, Application No. 05 85 2986, Dated Dec. 3, 2010.
Popov A.U. et al.: "Synthesis of 1,1-bis-(trifluoromethyl)alkylisocyanates, carbamates, and areas" Russian Chemical Bulletin, 2000, pp. 1202-1206.
Bolken T C et al: "Identification and characterization of potent small molecule inhibitor of hemorrhagic fever New World arenaviruses" Antiviral Research, Elsevier BV, NL, vol. 69,No. 2, Feb. 1, 2006, pp. 86-97.
Patani A et al: 'Biososterism: A Rational Approach in Drug Design Chemical Reviews, ACS, Washington, DC, US, vol. 96,No. 8, Jan. 1, 1996, pp. 3147-3176.
Co-Pending U.S. Appl. No. 12/673,983 ; Inventor Dai et al. ; Filed Feb. 18, 2010.
Popov A. V. et al.: Synthesis of 1,1-bis-(trifluoromethyl)alkly isocyanates, carbamates, and ureas, Russian Chemical Bulletin, Springer New York LLC, US; RU, vol. 49, No. 7, Jul. 1, 2000, pp. 1202-1206, XP002566001.
Bolken T.C. et al.: Identification and characterization of potent small molecule inhibitor of hemorrhagic fever New World arenaviruses, Antiviral Research, Elsevier BV, NL, vol. 69, No. 2, Feb. 1, 2006, pp. 86-97 XP025031484.
Examination Report Application No. 05 852 986, Dated Aug. 2, 2011.
Borio et al. Hemorrhagic Fever Viruses as Biological Weapons: Medical and Public Health Management, JAMA, 2002, vol. 287(18): 2391-2405.
Supplementary European Search Report EP Application No. 08825856.1, Dated Mar. 5, 2010.
Supplementary European Search Report EP Application No. 08825856.1, Dated Sep. 7, 2012.
Popov, A.V., et al., Russian Chemical Bulletin, International Edition, vol. 49, No. 7, pp. 1202-1206, Jul. 2000.
Krespan, C.G., Journal of Organic Chemistry, vol. 34, No. 5, pp. 1278-1281, 1969.
Registry (STN)[online], CAS Registry No. 664983-16-8; Mar. 19, 2004.
Registry (STN) [online], CAS Registry No. 355829-58-2; Sep. 11, 2001.
Registry (STN) [online], CAS Registry No. 345245-69-4; Jul. 10, 2001.
Registry (STN) [online], CAS Registry No. 345245-65-0; Jul. 10, 2001.
Registry (STN) [online], CAS Registry No. 345245-54-7; Jul. 10, 2001.
Registry (STN) [online], CAS Registry No. 339359-46-5; Jun. 5, 2001.
Registry (STN) [online], CAS Registry No. 339359-44-3; Jun. 5, 2001.
Registry (STN) [online], CAS Registry No. 339359-33-0; Jun. 5, 2001.
Registry (STN) [online], CAS Registry No. 339359-32-9; Jun. 5, 2001.
Registry (STN) [online], CAS Registry No. 339359-30-7; Jun. 5, 2001.
Registry (STN) [online], CAS Registry No. 339359-27-2; Jun. 5, 2001.
Registry (STN) [online], CAS Registry No. 339359-22-7; Jun. 5, 2001.
Registry (STN) [online], CAS Registry No. 339359-17-0; Jun. 5, 2001.
Registry (STN) [online], CAS Registry No. 339359-12-5; Jun. 5, 2001.
Registry (STN) [online], CAS Registry No. 339359-11-4; Jun. 5, 2001.
Registry (STN) [online], CAS Registry No. 339359-10-3; Jun. 5, 2001.
Registry (STN) [online], CAS Registry No. 339359-09-0; Jun. 5, 2001.
Registry (STN) [online], CAS Registry No. 339359-08-9; Jun. 5, 2001.
Registry (STN) [online], CAS Registry No. 339359-06-7; Jun. 5, 2001.
Registry (STN) [online], CAS Registry No. 339359-05-6; Jun. 5, 2001.
Registry (STN) [online], CAS Registry No. 312536-98-4; Jan. 2, 2001.
Registry (STN) [online], CAS Registry No. 301320-31-0; Nov. 6, 2000.
Registry (STN) [online], CAS Registry No. 345245-68-3; Jul. 10, 2001.
Registry (STN) [online], CAS Registry No. 339369-40-3; Jun. 5, 2001.
Registry (STN) [online], CAS Registry No. 339368-22-8; Jun. 5, 2001.
Registry (STN) [online], CAS Registry No. 339367-97-4; Jun. 5, 2001.
International Preliminary Report on Patentability for PCT/US2010/055086, dated May 16, 2013.
Patani A. et al.: Bioisosterism: A Rational Approach in Drug Design, Chemical Reviews, ACS, Washington, DC. US, vol. 96, No. 8, Jan. 1, 1996, pp. 3147-3176.
Bagai, S. and Lamb, R. A., J. Cell Biol., 135: 73-84 (1996).
Beyer, W. R., et al., "Oncoretrovirus and lentivirus vectors pseudotyped with lymphocytic choriomeningitis virus glycoprotein: generation, concentration, and broad host range." J. Virol. 76:1488-1495 (2002).
Beyer, W. R., et al., J. Virol., 77: 2866-72 (2003).
Bowen, M. D., et al., Virology, 219: 285-90 (1996).
Buchmeier, M.J., Clegg, J.C.S., Franze-Fernandez, M. T., Kolakofsky, D., Peters, C. J., and Southern, P. J., "Virus Taxonomy:

(56) References Cited

OTHER PUBLICATIONS

Sixth Report of the International Committee on Taxonomy of Viruses," Murphy, F.A., Fauquet, C. M. et al., Eds. Spmger-Verlag, New York, 319-323 (1995).
Candurra, N. A., Maskin, L., and Pamonte, E.B., Inhibition of arenavirus multiplication in vitro byphenotiazines, Antiviral Res., 31(3): 149-158 (1996).
Castagna, A., et al., Drugs, 65: 879-904 (2005).
Charrel, R. N. and de Lamballerie X., Antiviral Research. 57:89-100 (2003).
Childs, J. E., and Peters, C. J., "The Arenaviridae" Ed Salvato (ed.), Plenum Press, New York, pp. 331-84 (1993).
Cianci, C., et al., Antimicrob Agents Chemother, 48: 2448-54 (2004).
Clegg, J. C., Curr Top Microbiol Immunol, 262: 1-24 (2002).
Clegg, J.C.S., Bowen, M.D., et al., "Arenavirideal" in Van Regenmortel, M. H. V., Fauquet, C. M.,Bishop, D. H. L., Carsten, E.B., Estes, M.K., Lemon, S.M., Maniloff, J., Mayo, M.A., McGeoch, D.J., Pringle, C.R., Wickner, R. B. (Eds) Virus Taxonomy. Seven Report of the International Committee for the Taxonomy of Viruses, Academic Press, New York, pp. 633-640 (2000).
Connor, R. I., et al., "Vpr is required for efficient replication of human immunodeficiency virus type-1 in mononuclear phagocytes." Virology 206:935-944 (1995).
Enria, D.A., and Maiztegui, J.I., Antiviral treatment of Argentine Hemorrhagic Fever, Antiviral Res., 23: 23-31 (1994).
Froeschke, M., et al., J. Biol Chem., 278: 41914-20 (2003).
Garcia, C. C., et al., Antivir Chem Chemother, 11: 231-7 (2000).
Hall, W. C., et al., Am J Trop Med Hyg, 55: 81-8 (1996).
Harman, A., et al., J Virol, 76: 10708-16 (2002).
Huggins, J.W., Prospects for Treatment of Viral Hemorrhagic Fevers With Ribavirin, A Broad-Spectrum Antiviral Drug, Rev. Infect. Dis., II:Suppl.4:S750-S761 (1989).
Jeetendra, E., et al., J Virol, 77: 12807-18 (2003).
Kilgore, P. E., Ksiazek, T. G., Rollin, P. E., et al., Treatment of Bolivian Hemorrhagic Fever with intravenous ribavirin, Clin. Infect. PIS., 24: 718-722 (1997).
Kinomoto, M., et al., J Virol, 79: 5996-6004 (2005).
Kunz, S., et al., Virology, 314: 168-78 (2003).
Leifer, E., Gocke, D.J., et al., Report of a laboratory-acquired infection treated with plasma from a person recently recovered from the disease, Am. J. Trop. Med. Hyg., 19:677-679 (1970).
Lenz, O., et al., Proc Natl Acad Sci USA, 98: 12701-5 (2001).
Maron, M. D. and Ames, B. N., Mutat Res, 113: 173-215 (1983).
McCormick, J. B., Epidemiology and control of Lassa fever, Curr. Top. Microbiol. Immunol., 134: 69-78 (1987).
McCormick, J.B., King, I.J., Webb, P.A., et al., Lassa Fever: Effective therapy with Ribavirin, N. Engl. J. Med., 314: 20-26 (1986).
Naldini, L., et al., "In vivo gene delivery and stable transduction of nondividing cells by a lentiviral vector." Science 272:263-267 (1996).
Oldfield, V., et al., Drugs, 65: 1139-60 (2005).
Peters C. J., "Arenavirus diseases," in Porterfield J., ed., Exotic Viral Infection, London: Chapman and Hall Medical, 227-246 (1995).
Peters, C. J., et al., Curr Top Microbiol Immunol, 134: 5-68 (1987).
Rawls, W. E., Banerjee, S.N., McMillan, C. A., and Buchmeier, M. J., Inhibition of Pichinde virus replication by actinomycin D, J. Gen. Virol., 33(3): 421-434 (1976).
Rojek, J. M., et al., "Characterization of the cellular receptors for the South American hemorrhagic fever viruses Junin, Guanarito, and Machupo." Virology 349:476-491 (2006).
Simmons, G., et al., "Characterization of severe acute respiratory syndrome-associated coronavirus (SARS-CoV) spike glycoprotein-mediated viral entry." Proc. Natl. Acad. Sci. USA 101:4240-4245 (2004).
Southern, P. J., Virology, 2: 1505-51 (2001).
Wachsman, M. B., Lopez, E. M. F., Ramirez, J. A., Galagovsky, L. R., and Coto, C. E., Antiviral effect ofbrassinosteroids against herpes virus and arenavirus, Antiviral. Chem. Chemother., 11(1): 71-77 (2000).
Weissenbacher, M. C., et al., Infect Immun, 35: 425-30 (1982).
West, J. T., et al., J Virol, 75: 9601-12 (2001).
Wool-Lewis, R. J., and P. Bates, "Characterization of Ebola virus entry by using pseudotyped viruses: identification of receptor-deficient cell lines." J. Virol. 72:3155-3160 (1998).
Yao, Q. and Compans, R. W., J Virol, 69: 7045-53 (1995).
Goff et. al. A survey of antiviral drugs of bioweapons, Antiviral Chemistry and Chemotherapy. 2005, vol. 16, pp. 283-294.
Bolken et. al. Identification and characterization of potent small molecule inhibitor of hemorrhagic fever new world arenaviruses. Antiviral Research, Mar. 2005, vol. 65, No. 3, pp. 86-97.

* cited by examiner

FORMULA: $C_{13}H_{15}N_3O_3F_6S_1$

MW: 407.33

4000pfu +5uM ST-336 (1A) → 1/10 DILUTION → 400pfu +0.5uM ST-336 (1B) → 1/10 DILUTION → 40pfu +0.05uM ST-336 (1C)

4000pfu +DMSO (2A) → 400pfu +DMSO (2B) → 40pfu +DMSO (2C)

400pfu AND ADD +0.5uM ST-336 (3B) → 40pfu AND ADD +0.05uM ST-336 (3C)

WT TACARIBE

| 1A | 2A | Cells Only |
| 1B | 2B | 3B |
| 1C | 2C | 3C |

FORMULA: $C_{12}H_{11}N_3O_4F_8S_1$

MW: 445.29

```
                         SEQUENCE LISTING


<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

gcctaactga accaggtgaa tc                                                22


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

taagacttcc gcaccacagg                                                   20


<210> SEQ ID NO 3
<211> LENGTH: 60
<212> TYPE: PRT
<213> ORGANISM: Tacaribe virus

<400> SEQUENCE: 3

Asp Phe Leu Ile Ser Glu Ile Leu Ser Lys Glu Tyr Ser Glu Arg Gln
1               5                   10                  15

Gly Arg Thr Pro Ile Thr Leu Val Asp Ile Cys Phe Trp Ser Thr Val
            20                  25                  30

Phe Phe Thr Ser Thr Leu Phe Leu His Leu Ile Gly Phe Pro Thr His
        35                  40                  45

Arg His Ile Arg Gly Glu Gly Cys Pro Leu Pro His
    50                  55                  60


<210> SEQ ID NO 4
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

```
Asp Phe Leu Ile Ser Glu Ile Leu Ser Lys Glu Tyr Ser Glu Arg Gln
1               5                   10                  15

Gly Arg Thr Pro Thr Thr Leu Val Asp Ile Cys Phe Trp Ser Thr Val
            20                  25                  30

Phe Phe Thr Ser Thr Leu Phe Leu His Leu Ile Gly Phe Pro Thr His
        35                  40                  45

Arg His Ile Arg Gly Glu Gly Cys Pro Leu Pro His
    50                  55                  60


<210> SEQ ID NO 5
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Phe Leu Ile Ser Glu Ile Leu Ser Lys Glu Tyr Ser Glu Arg Gln
1               5                   10                  15

Gly Arg Asn Pro Ile Thr Leu Val Asp Ile Cys Phe Trp Ser Thr Val
            20                  25                  30

Phe Phe Thr Ser Thr Leu Phe Leu His Leu Ile Gly Phe Pro Thr His
        35                  40                  45

Arg His Ile Arg Gly Glu Gly Cys Pro Leu Pro His
    50                  55                  60


<210> SEQ ID NO 6
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Phe Leu Ile Ser Glu Ile Leu Ser Lys Glu Tyr Ser Glu Arg Gln
1               5                   10                  15

Gly Arg Thr Pro Ile Thr Leu Val Asp Ile Cys Phe Trp Ser Thr Val
            20                  25                  30

Phe Phe Thr Ile Thr Leu Phe Leu His Leu Ile Gly Phe Pro Thr His
        35                  40                  45

Arg His Ile Arg Gly Glu Gly Cys Pro Leu Pro His
    50                  55                  60


<210> SEQ ID NO 7
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Phe Leu Ile Ser Glu Ile Leu Ser Lys Glu Tyr Ser Glu Arg Gln
1               5                   10                  15

Gly Arg Thr Pro Ile Thr Leu Val Asp Ile Cys Phe Trp Ser Thr Val
            20                  25                  30

Phe Phe Thr Ser Thr Leu Ile Leu His Leu Ile Gly Phe Pro Thr His
        35                  40                  45

Arg His Ile Arg Gly Glu Gly Cys Pro Leu Pro His
    50                  55                  60
```

<210> SEQ ID NO 8
<211> LENGTH: 60
<212> TYPE: PRT
<213> ORGANISM: Machupo virus

<400> SEQUENCE: 8

Asp Phe Leu Ile Ser Glu Met Leu Ser Lys Glu Tyr Ala Glu Arg Gln
1 5 10 15

Gly Lys Thr Pro Ile Thr Leu Val Asp Ile Cys Phe Trp Ser Thr Val
20 25 30

Phe Phe Thr Ala Ser Leu Phe Leu His Leu Val Gly Ile Pro Thr His
35 40 45

Arg His Leu Lys Gly Glu Ala Cys Pro Leu Pro His
50 55 60

<210> SEQ ID NO 9
<211> LENGTH: 60
<212> TYPE: PRT
<213> ORGANISM: Junin virus

<400> SEQUENCE: 9

Asp Phe Leu Ile Ser Glu Met Leu Ser Lys Glu Tyr Ser Asp Arg Gln
1 5 10 15

Gly Lys Thr Pro Leu Thr Leu Val Asp Ile Cys Phe Trp Ser Thr Val
20 25 30

Phe Phe Thr Ala Ser Leu Phe Leu His Leu Val Gly Ala Pro Thr His
35 40 45

Arg His Ile Arg Gly Glu Ala Cys Pro Leu Pro His
50 55 60

<210> SEQ ID NO 10
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Asp Phe Leu Ile Ser Glu Met Leu Ser Lys Glu Tyr Ser Asp Arg Gln
1 5 10 15

Gly Lys Thr Pro Leu Thr Leu Val Asp Ile Cys Ile Asn Ser Thr Val
20 25 30

Phe Phe Thr Ala Ser Leu Phe Leu His Leu Val Gly Ala Pro Ser His
35 40 45

Arg His Ile Arg Gly Glu Ala Cys Pro Leu Pro His
50 55 60

<210> SEQ ID NO 11
<211> LENGTH: 60
<212> TYPE: PRT
<213> ORGANISM: Guanarito virus

<400> SEQUENCE: 11

Asp His Leu Ile Ala Glu Met Leu Ser Lys Glu Tyr Gln Asp Arg Gln
1 5 10 15

Gly Lys Thr Pro Leu Thr Leu Val Asp Leu Cys Phe Trp Ser Ala Ile
20 25 30

Phe Phe Thr Thr Ser Leu Phe Leu His Leu Val Gly Phe Pro Thr His
35 40 45

-continued

```
Arg His Ile Gln Gly Asp Pro Cys Pro Leu Pro His
    50                  55                  60


<210> SEQ ID NO 12
<211> LENGTH: 60
<212> TYPE: PRT
<213> ORGANISM: Sabia virus

<400> SEQUENCE: 12

Asp His Leu Leu Ser Glu Met Leu Asn Lys Glu Tyr Ile Asp Arg Gln
1               5                   10                  15

Gly Lys Thr Pro Leu Thr Leu Val Asp Ile Cys Phe Trp Ser Thr Leu
            20                  25                  30

Phe Phe Thr Thr Thr Leu Phe Leu His Leu Val Gly Phe Pro Thr His
        35                  40                  45

Arg His Ile Arg Gly Glu Pro Cys Pro Leu Pro His
    50                  55                  60


<210> SEQ ID NO 13
<211> LENGTH: 60
<212> TYPE: PRT
<213> ORGANISM: Amapari virus

<400> SEQUENCE: 13

Asp His Leu Leu Ala Glu Ile Leu Ser Lys Glu Tyr Gln Asp Arg Gln
1               5                   10                  15

Gly Lys Thr Pro Ile Thr Leu Val Asp Met Cys Phe Trp Ser Ala Ile
            20                  25                  30

Phe Phe Asp Asn Lys Ser Leu Leu His Leu Val Gly Pro Pro Thr Ser
        35                  40                  45

Arg His Ile Val Gly Glu Ala Cys Pro Leu Pro His
    50                  55                  60
```

SULFONYL SEMICARBAZIDES, SEMICARBAZIDES AND UREAS, PHARMACEUTICAL COMPOSITIONS THEREOF, AND METHODS FOR TREATING HEMORRHAGIC FEVER VIRUSES, INCLUDING INFECTIONS ASSOCIATED WITH ARENA VIRUSES

This application is a divisional of U.S. application Ser. No. 11/653,972 filed Jan. 17, 2007, now granted as U.S. Pat. No. 7,994,221, which is a continuation-in-part of international application number PCT/US2005/43931, filed on Dec. 6, 2005, which claims priority of U.S. Provisional Application No. 60/632,990, filed Dec. 6, 2004, all of which are hereby incorporated by reference in their entirety.

STATEMENT REGARDING FEDERALLY SPONSORED RESEARCH OR DEVELOPMENT

This invention was made with U.S. government support under Grant R43 AI056525-01, Grant R43AI056525-02 and Grant R44 AI056525-04 awarded by the National Institute of Health (NIH). The U.S. Government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 12, 2011, is named 56441026.txt and is 7,802 bytes in size.

FIELD

The use of sulfonyl semicarbazides, carbonyl semicarbazides semicarbazides, and ureas, as well as derivatives and analogs thereof, and pharmaceutical compositions containing the same, for the treatment or prophylaxis of viral infections and diseases associated therewith. In particular, those viral infections and associated diseases caused by hemorrhagic fever vinases, such as Arenaviruses may be treated.

BACKGROUND

Hemorrhagic fever viruses have been discussed in the scientific literature. The following publications, patents, and patent applications are cited in this application as superscript numbers:

1. Charrel, R. N. and de Lamballerie X., Antiviral Research. 57:89-100 (2003).
2. Peters C. J., "*Arenavirus diseases*," in Porterfield 3., ed., Exotic Viral Infection. London: Chapman and Hall Medical, 227-246 (1995).
3. Buchmeier, M. J., Clegg, J. C. S., Franze-Fernandez, M. T., Kolakofsky, D., Peters, C. J., and Southern, P. J., "*Virus Taxonomy: Sixth Report of the International Committee on Taxonomy of Viruses*," Murphy, F. A., Fauquet, C. M. et al., Eds. Sprnger-Verlag, New York, 319-323 (1995).
4. Clegg, J. C. S., Bowen, M. D., et al., "*Arenavirideal*" in Van Regenmortel, M. H. V., Fauquet, C. M., Bishop, D. H. L., Carsten, E. B., Estes, M. K., Lemon, S. M., Maniloff, J., Mayo, M. A., McGeoch, D. J., Pringle, C. R., Wickner, R. B. (Eds) *Virus Taxonomy. Seven Report of the International Committee for the Taxonomy of Viruses*, Academic Press, New York, pp 633-640 (2000).
5. McCormick, J. B., *Epidemiology and control of Lassa fever*, Curr. Top. Microbiol. IMMUNOL., 134: 69-78 (1987).
6. Leifer, E., Gocke, D. J., et al., *Report of a laboratory-acquired infection treated with plasma from a person recently recovered from the disease*, Am. J. Trop. Med. Hyg., 19:677-679 (1970).
7. McCormick, J. B., King, I. J., Webb, P. A., et al., *Lassa Fever: Effective therapy with Ribavirin*, N. Engl. J. Med., 314: 20-26 (1986).
8. Kilgore, P. E., Ksiazek, T. G., Rollin, P. E., et al., *Treatment of Bolivian Hemorrhagic Fever with intravenous ribavirin*, Clin. Infect. Pis., 24: 718-722 (1997).
9. Enria, D. A., and Maiztegui, J. I., *Antiviral treatment of Argentine Hemorrhagic Fever*, Antiviral Res., 23: 23-31 (1994).
10. Huggins, J. W., *Prospects For Treatment Of Viral Hemorrhagic Fevers With Ribavirin, A Broad-Spectrum Antiviral Drug*, Rev. Infect. Dis., II:Suppl. 4:S750-S761 (1989).
11. Candurra, N. A., Maskin, L., and Pamonte, E. B., *Inhibition of arenavirus multiplication in vitro byphenotiazines*, Antiviral Res., 31(3): 149-158 (1996).
12. Glushakova, S. E., Lakuba, A. I., Vasiuchkov, A. P., Mar'iankova, R. F., Kukareko, T. M., Stel'makh, T. A., Kurash, T. P., and Lukashevich, I. S., *Lysosomotropic agents inhibit the penetration of arenavirus into a culture of BHK-*21 *andvero cells*, Voprosy Virusolog II. 35(2): 146-150 (1990).
13. Petkevich, A. S., Sabynin, V. M., Lemeshko, N. N., Lukashevich, I. S., and Beloruss, N., *Study of the effect ofrimantadine on the reproduction of several arenaviruses*, Epidemiol. Mikrobiol., 138-143 (1982).
14. Wachsman, M. B., Lopez, E. M. F., Ramirez, J. A., Galagovsky, L. R., and Coto, C. E., *Antiviral effect of brassinosteroids against herpes virus and arenavirus*, Antiviral. Chem. Chemother., 11(1): 71-77 (2000).
15. Rawls, W. E., Banerjee, S. N., McMillan, C. A., and Buchmeier, M. J., *Inhibition of Pichinde virus replication by actinomycin D*, J. Gen. Virol., 33(3): 421-434 (1976).
16. Enria, D. A., Feuillade, M. R., Levis, S., Briggiler, A. M., Ambrosio, A. M., Saavedra, M. C, Becker, J. L., Aviles, G., Garcia, J., Sabattini, M., "*Impact of vaccination of a high-risk population for Argentine hemorrhagic fever with a live-attenuated Junin virus vaccine*" in Saluzzo, J. F., Dodet, B., (eds) FACTORS IN THE EMERGENCE AND CONTROL FOR RODENT-BORNE VIRAL DISEASES, Paris: Elsevier, 1999, pp. 273-279 (1999).
17. Bagai, S, and Lamb, R. A., J. Cell Biol., 135: 73-84 (1996).
18. Beyer, W. R., et al., J. Virol., 77: 2866-72 (2003).
19. Bowen, M. D., et al., Virology, 219: 285-90 (1996).
20. Castagna, A., et al., Drugs, 65: 879-904 (2005).
21. Childs, J. E., and Peters, C. J., "*The Arenaviridae*" Ed Salvato (ed.), Plenum Press, New York, pp. 331-84 (1993).
22. Cianci, C., et al., Antimicrob Agents Chemother, 48: 2448-54 (2004).
23. Clegg, J. C., Curr Top Microbiol Immunol, 262: 1-24 (2002).
24. Froeschke, M., et al., J. Biol Chem., 278: 41914-20 (2003).
25. Garcia, C. C., et al., Antivir Chem Chemother, 11: 231-7 (2000).
26. Hall, W. C., et al., Am J Trop Med Hyg, 55: 81-8 (1996).
27. Harman, A., et al., J Virol, 76: 10708-16 (2002).
28. Jeetendra, E., et al., J Virol, 77: 12807-18 (2003).
29. Kinomoto, M., et al., J Virol, 79: 5996-6004 (2005).
30. Kunz, S., et al., Virology, 314: 168-78 (2003).

31. Lenz, O., et al., Proc Natl Acad Sci USA, 98: 12701-5 (2001).

32. Maron, M. D. and Ames, B. N., MUTAT RES, 113: 173-215 (1983).

33. Oldfield, V., et al., Drugs, 65: 1139-60 (2005).

34. Peters, C. J., et al., Curr Top Microbiol Immunol, 134: 5-68 (1987).

35. Petkevich, A. S., et al., Vopr Virusol, 244-5 (1981).

36. Southern, P. J., Virology, 2: 1505-51 (2001).

37. Weissenbacher, M. C., et al., Infect Immun, 35: 425-30 (1982).

38. West, J. T., et al., J Virol, 75: 9601-12 (2001).

39. Yao, Q. and Compans, R. W., J Virol, 69: 7045-53 (1995).

40. Beyer, W. R., et al., "*Oncoretrovirus and lentivirus vectors pseudo typed with lymphocytic choriomeningitis virus glycoprotein: generation, concentration, and broad host range*." J. Virol. 76:1488-1495 (2002).

41. Connor, R. I., et al., "*Vpr is required for efficient replication of human immunodeficiency virus type-I in mononuclear phagocytes*." Virology 206:935-944 (1995).

42. Naldini, L., et al., "*In vivo gene delivery and stable transduction of nondividing cells by a lentiviral vector*." Science 272:263-267 (1996).

43. Rojek, J. M., et al., "Characterization of the cellular receptors for the South American hemorrhagic fever viruses Junin, Guanarito, and Machupo." Virology 349: 476-491 (2006).

44. Simmons, G., et al., "Characterization of severe acute respiratory syndrome-associated coronavirus (SARS-CoV) spike glycoprotein-mediated viral entry." Proc. Natl. Acad. Sci. USA 101:4240-4245 (2004).

45. Wool-Lewis, R. J., and P. Bates, "*Characterization of Ebola virus entry by using pseudoryped viruses: identification of receptor-deficient cell lines*." J. Virol. 72:3155-3160 (1998).

All of the publications, patents, and patent applications cited in this application are herein incorporated by reference in their entirety to the same extent as if each individual publication, patent, or patent application was specifically and individually indicated to be incorporated by reference in its entirety.

The National Institute of Allergy and Infectious Diseases (NIAID) and the Centers for Disease Control and Prevention (CDC) have classified a number of viruses as potential agents of bioterrorism (www.bt.cdc.gov/agent/agentlist-category.asp). The highest threat agents, the Category A pathogens, have the greatest potential for adverse public health impact and mass casualties if used in ill-intentioned ways. Within the Category A pathogens, there are a number of viruses that can cause viral hemorrhagic fevers with high case fatality rates. The Category A hemorrhagic fever viruses pose serious threats as potential biological weapons because: 1) they can be disseminated through aerosols; 2) a low dose (1-10 plaque forming unit (pfu)) can cause disease; 3) they cause severe morbidity and mortality (case fatality rates of 15-30%); 4) they can cause fear and panic in the general public; 5) there are no U.S.-approved effective vaccines or specific antivirals available; 6) these pathogens are easily available and can be readily produced in large quantities; and 7) research on weaponizing various hemorrhagic fever viruses has been conducted).[1]

Arenaviruses are enveloped viruses with a genome that consists of two single-stranded RNA segments designated small (S, 3.5 Kb) and large (L, 7.5 Kb), both with an ambisense coding arrangement.[36] The S RNA segment encodes the major structural proteins, nucleocapsid protein (NP) and a precursor envelope protein (GPC) encoding two envelope glycoproteins (external GP1 and transmembrane GP2),[18,24,30,31] and the L RNA segment encodes the RNA polymerase protein L and an 11 KDa protein, Z protein, with putative regulatory function.[19] GP1 and GP2, which form the tetrameric surface glycoprotein spike, are responsible for virus entry into targeted host cells.

The family Arenaviridae consists of a single genus (Arenavirus) that includes several viruses (currently 23 recognized viruses[1]) causing severe hemorrhagic fever diseases in humans.[2] The Arenaviridae family has been divided into two groups according to sequence-based phylogeny. The "Old World" group, originated from Africa, includes the human pathogens lymphocytic choriomeningitis (LCM) virus and Lassa virus. The "New World" group, originated from Latin America, is divided into 3 clades. Clade B includes, in addition to Tacaribe and Amapari viruses, the Category A human pathogenic viruses Junin (Argentine hemorrhagic fever), Machupo (Bolivian hemorrhagic fever), Guanarito (Venezuelan hemorrhagic fever), and Sabia (Brazilian hemorrhagic fever). These Category A viruses are capable of causing severe and often fatal hemorrhagic fever disease in humans.

Rodents are the natural host of arenaviruses, although Tacaribe virus is found in bats. The arenaviruses characteristically produce chronic viremic infections in their natural host,[15] which in turn shed virus in their urine and feces, ultimately infecting humans in close contact with these infected materials either by aerosol or direct contact with skin abrasions or cuts. The natural history of the human disease is determined by the pathogenicity of the virus, its geographical distribution, the habitat and the habits of the rodent reservoir host, and the nature of the human-rodent interaction.[21]

Several Arenaviruses are associated with severe hemorrhagic disease in human. Lassa virus (from the Old World group) is responsible for Lassa hemorrhagic fever, while 4 viruses from the New World group (all from Clade B) cause severe hemorrhagic fever in human. Those viruses are: Junin virus responsible for Argentine hemorrhagic fever, Machupo virus for Bolivian hemorrhagic fever, and Guanarito virus for Venezuelan hemorrhagic fever. Sabia virus was isolated from a fatal case of hemorrhagic fever in Brazil. It is estimated that Lassa virus causes 100,000-300,000 infections and approximately 5,000 deaths annually.[5] So far, an estimated 30,000 confirmed cases of Junin infections have been documented, while about 2,000 of Machupo, 200 of Guanarito and only 2 of Sabia.[1]

Recent concerns over the use of Arenaviruses as biological weapons have underscored the necessity of developing small molecule therapeutics that target these viruses.[1] The availability of antiviral drugs directed at these viruses would provide treatment and a strong deterrent against their use as biowarfare agents. Since antiviral drugs can be easily administered (oral, pill, or liquid) and exert their antiviral effect within hours of administration, they will serve to effectively treat diseased patients, protect those suspected of being exposed to the pathogen (post-exposure prophylaxis), and assist in the timely containment of an outbreak.

Currently, there are no virus-specific treatments approved for use against Arenavirus hemorrhagic fevers. Present disease management consists of general supportive care: monitoring and correcting fluid, electrolyte and osmotic imbalances and treating hemorrhaging with clotting factor or platelet replacement. Convalescent immune serum therapy may be effective in treating cases of Junin and Machupo virus disease, but the availability of such serum is extremely limited.

Ribavirin, a nucleoside analog, has been used with some success in Lassa fever patients. In small trials, intravenous ribavirin given to patients within the first 6 days after development of fever decreased mortality from 76% to 9%.[7-9] A controlled trial of 18 patients with Argentine hemorrhagic fever resulted in 13% mortality in treated patients compared with 40% in untreated patients)° Ribavirin therapy is associated with adverse effects including a dose-related, reversible hemolytic anemia and also has demonstrated teratogenicity and embryo lethality in several animal species. It is therefore classified as a pregnancy category X drug, contraindicated during pregnancy. Intravenous ribavirin is available in limited supplies in the U.S. for compassionate use under an FND application. The dosing regimen for ribavirin therapy that has been used in cases of Lassa fever consists of an initial 30 mg/kg intravenous (IV) loading dose, followed by 16 mg/kg IV every 6 hours for 4 days; then 8 mg/kg IV every 8 hours for 6 days (total treatment time 10 days). The cost of treatment for an adult male is approximately $800. The attributes of ribavirin make it less than ideal for the treatment of Arenavirus hemorrhagic fevers.

A number of in vitro inhibitors of Arenavirus replication have been reported in the literature including phenothiazines, trifluoroperazine and chlorpromazine,[1] amantadine,[12,13] brassinosteroids[14] and actinomycin D.[15] The anti-Arenavirus activities of these compounds are generally weak and nonspecific.

The only Arenavirus hemorrhagic fever for which studies have been undertaken toward development of a vaccine has been Argentine hemorrhagic fever (AHF) caused by Junin virus. A live-attenuated vaccine, called Candid 1, has been evaluated in controlled trials among agricultural workers in AHF-endemic areas, where it appeared to reduce the number of reported AHF cases with no serious side effects.[16] It is not known if the Candid 1 vaccine would be useful against other Arenavirus hemorrhagic fevers and this vaccine is not available in the United States of America.

Tacaribe virus is a biosafety level 2 (BSL 2) New World arenavirus (NWA) that is found in Clade B and phylogenetically related to the Category A NWA (Junin, Machupo, Guanarito and Sabiá). Tacaribe virus is 67% to 78% identical to Junin virus at the amino acid level for all four viral proteins. In order to screen for inhibitors of NWA a high-throughput screening (HTS) assay for virus replication was developed using Tacaribe virus as a surrogate for Category A NWA. A 400,000 small molecule library was screened using this HTS assay. A lead series was chosen based on drug properties and this series was optimized through iterative chemistry resulting in the identity of a highly active and specific small molecule inhibitor of Tacaribe virus with selective activity against human pathogenic NWA (Junin, Machupo, Guanarito and Sabiá). This molecule demonstrates favorable pharmacodynamic properties which permitted the demonstration of in vivo anti-arenavirus activity in a newborn mouse model.

All human pathogens Arenaviruses from the New World group causing hemorrhagic fever are from the Clade B. These human pathogen viruses require manipulation under high-level containment (BSL-4). However, Amapari and Tacaribe viruses also from Clade B can be grown in tissue culture under BSL-2 (low-level) containment. Working under low-level containment makes experimentations easier and safer with these viruses. While Amapari virus produces low cytopathic effect, Tacaribe virus can be grown readily in cell culture and produce robust CPE in 4 to 6 days. Since this CPE is directly related to viral replication, compounds that inhibit virus replication in cell culture can be identified readily as conferring protection from virus-induced CPE (although it is theoretically possible to inhibit CPE without inhibiting virus replication). Moreover, compounds having identified activity against Tacaribe virus will also likely be active against Arenavirus human pathogen causing hemorrhagic fever (Junin, Machupo, Guanarito and Sabia) given the high degree of homology (around 70% identity for all 4 proteins of Tacaribe virus compared to Junin virus, with long stretch of protein with perfect identity) between these viruses.

What is needed in the art are new therapies and preventives for the treatment of viral infections and associated diseases, such as caused by hemorrhagic fever viruses like Arenaviruses.

SUMMARY

Provided are compounds and compositions and/or methods for the treatment and prophylaxis of viral infections, as well as diseases associated with viral infections in living hosts. In particular, provided are compounds and compositions and/or methods for the treatment and prophylaxis of hemorrhagic fever viruses, such as Arenaviruses.

In one embodiment provided herein is a method for the treatment or prophylaxis of a viral infection or disease associated therewith, comprising administering in a therapeutically effective amount to a mammal in need thereof, a compound of Formula I or a pharmaceutically acceptable salt thereof. In another embodiment, a pharmaceutical composition that comprises a pharmaceutically-effective amount of the compound or a pharmaceutically-acceptable salt thereof, and a pharmaceutically-acceptable carrier is provided. In addition, compounds of Formula I, as well as pharmaceutically-acceptable salts thereof are provided.

Compounds of Formula I include

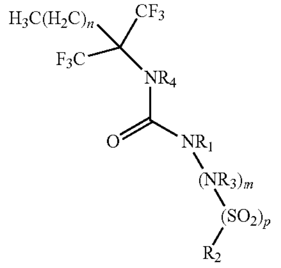

wherein n is an integer from 0-6;

m is an integer from 0-1;

p is an integer from 0-1;

$R_1$ is selected from the group consisting of H and alkyl;

$R_2$ is selected from the group consisting of substituted or unsubstituted phenyl, substituted and unsubstituted aryl, substituted and unsubstituted heteroaryl, substituted or unsubstituted alkyl, substituted or unsubstituted branched alkyl, and substituted or unsubstituted unsaturated cycloheteroalkyls; or where $R_1$ and $R_2$ combine together to form a substituted or unsubstituted $C_{4-10}$ cyclic saturated heteroalkyl;

$R_3$ is selected from the group consisting of H and alkyl;

or a pharmaceutically-acceptable salt thereof.

Other compounds of Formula I include:

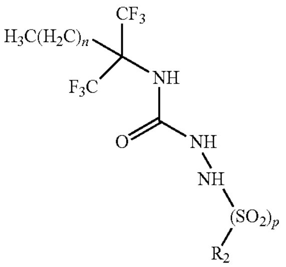

IA wherein $R_2$ is selected from the group consisting of substituted or unsubstituted phenyl, substituted and unsubstituted aryl, substituted and unsubstituted heteroaryl, substituted or unsubstituted alkyl, substituted or unsubstituted branched alkyl, and substituted or unsubstituted unsaturated cycloheteroalkyls or a pharmaceutically-acceptable salt thereof.

Further compounds of Formula I include:

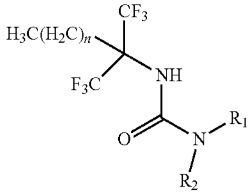

IB wherein $R_1$ is selected from the group consisting of H and alkyl;

$R_2$ is selected from the group consisting of substituted or unsubstituted phenyl, substituted and unsubstituted aryl, substituted and unsubstituted heteroaryl, substituted or unsubstituted alkyl, substituted or unsubstituted branched alkyl, and substituted or unsubstituted unsaturated cycloheteroalkyls;

or where $R_1$ and $R_2$ combine together to form a substituted or unsubstituted $C_{4-10}$ cyclic saturated heteroalkyl;

or a pharmaceutically-acceptable salt thereof.

In other embodiments, in the compound of Formula I, n is 0 or 1. Also, in other embodiments, in the compound of Formula I, m is 1 and p is 1 or alternatively, m is 0 and p is 0.

In further embodiments, in Formula I, $R_1$ and $R_2$ combine together to form a substituted or unsubstituted $C_{4-10}$ cyclic saturated heteroalkyl selected from the group consisting of:

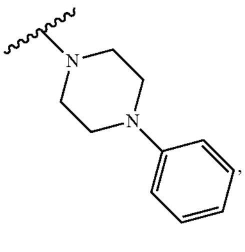,
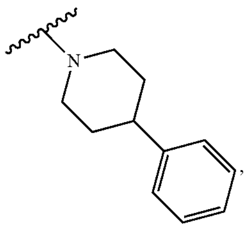,

-continued

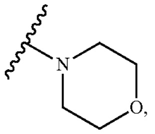
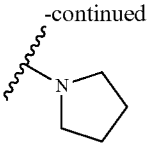,
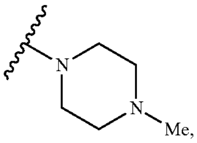
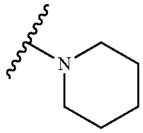
and
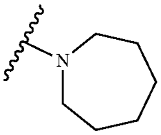

In still further embodiments, in Formula I, $R_2$ is selected from the group consisting of:

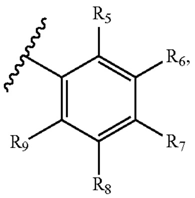
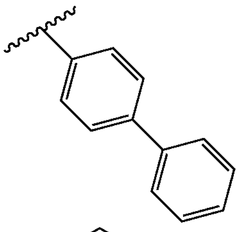,
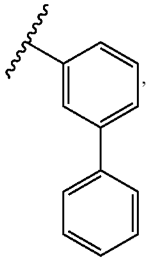,
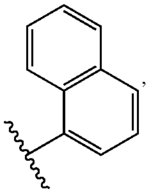,
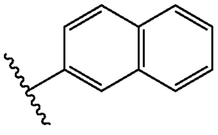
and
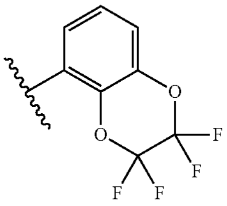

wherein each of $R_5$, $R_6$, $R_7$, $R_8$ and $R_9$ is independently selected from the group consisting of: hydrogen, acetyl, methoxy, trifluoromethyl, fluoro, chloro, bromo, iodo, acylamino, methyl, sulfonamide, trifluoromethoxy, carboxy, cyano and 1,1,2,2-tetrafluoroethoxy.

In particular, certain embodiments relate to a compound of Formula I selected from the group consisting of N-2-(1,1,1,3,3,3-Hexafluoro-2-methylpropyl)-2-[(4-(phenyl)-phenylsulfonyl]hydrazine-1-carboxamide;

N-2-(1,1,1,3,3,3-Hexafluoro-2-methylpropyl)-2-[(4-(2-methyl-2-propyl)-phenylsulfonyl]hydrazine-1-carboxamide;

N-2-(1,1,1,3,3,3-Hexafluoro-2-methylpropyl)-2-[7-(4-methyl-3,4-dihydro-2H-benzo[1,4]oxazinyl)sulfonyl]hydrazine-1-carboxamide;

N-2-(1,1,1,3,3,3-Hexafluoro-2-methylpropyl)-2-[5-dimethylamino-naphthyl) sulfonyl]hydrazine-1-carboxamide;

N-2-(1,1,1,3,3,3-Hexafluoro-2-methylpropyl)-2-[(2,4,6-trimethylphenyl)sulfonyl]hydrazine-1-carboxamide;

N-2-(1,1,1,3,3,3-Hexafluoro-2-methylpropyl)-2-[(3-chloro-6-methoxyphenyl) sulfonyl]hydrazine-1-carboxamide;

N-2-(1,1,1,3,3,3-Hexafluoro-2-methylpropyl)-2-[(3,6-dimethoxyphenyl)sulfonyl]hydrazine-1-carboxamide;

N-2-(1,1,1,3,3,3-Hexafluoro-2-methylpropyl)-2-[(4-(4-[1,2,3]thiadiazolyl)phenyl)sulfonyl]hydrazine-1-carboxamide;

N-2-(1,1,1,3,3,3-Hexafluoro-2-methylpropyl)-2-[(3-bromophenyl)sulfonyl]hydrazine-1-carboxamide;

N-2-(1,1,1,3,3,3-Hexafluoro-2-methylpropyl)-2-[(4-bromophenyl)sulfonyl]hydrazine-1-carboxamide;

N-2-(1,1,1,3,3,3-Hexafluoro-2-methylpropyl)-2-[(4-methylphenyl)sulfonyl]hydrazine-1-carboxamide;

N-2-(1,1,1,3,3,3-Hexafluoro-2-methylpropyl)-2-[(4-methoxyphenyl)sulfonyl]hydrazine-1-carboxamide;

N-2-(1,1,1,3,3,3-Hexafluoro-2-methylpropyl)-2-[(4-difluoromethoxyphenyl)sulfonyl]hydrazine-1-carboxamide;

N-2-(1,1,1,3,3,3-Hexafluoro-2-methylpropyl)-2-[(3-fluoro-4-chloro-phenyl)sulfonyl]hydrazine-1-carboxamide;

N-2-(1,1,1,3,3,3-Hexafluoro-2-methylpropyl)-2-[(4-trifluoromethoxyphenyl)sulfonyl]hydrazine-1-carboxamide;

N-2-(1,1,1,3,3,3-Hexa fluoro-2-methylpropyl)-2-[(4-fluorophenyl)sulfonyl]hydrazine-1-carboxamide;

N-2-(1,1,1,3,3,3-Hexa fluoro-2-methylpropyl)-2-[(3-methoxyphenyl)sulfonyl]hydrazine-1-carboxamide;

N-2-(1,1,1,3,3,3-Hexafluoro-2-methylpropyl)-2-[(2-methylphenyl)sulfonyl]hydrazine-1-carboxamide;

N-2-(1,1,1,3,3,3-Hexafluoro-2-methylpropyl)-2-[(3-trifluoromethylphenyl)sulfonyl]hydrazine-1-carboxamide;

N-2-(1,1,1,3,3,3-Hexafluoro-2-methylpropyl)-2-[(2,4-dimethoxyphenyl)sulfonyl]hydrazine-1-carboxamide;

N-2-(1,1,1,3,3,3-Hexafluoro-2-methylpropyl)-2-[2-(5-chloro-1,3-dimethyl-/H-pyrazolyl)sulfonyl]hydrazine-1-carboxamide;

N-2-(1,1,1,3,3,3-Hexafluoro-2-methylpropyl)-2-[(3-methylphenyl)sulfonyl]hydrazine-1-carboxamide;

N-2-(1,1,1,3,3,3-Hexafluoro-2-methylpropyl)-2-[(4-trifluoromethylphenyl)sulfonyl]hydrazine-1-carboxamide;

N-2-(1,1,1,3,3,3-Hexafluoro-2-methylpropyl)-2-[(2-trifluoromethylphenyl)sulfonyl]hydrazine-1-carboxamide;

N-2-(1,1,1,3,3,3-Hexafluoro-2-methylpropyl)-2-[4-(pyrrolidin-1-sulfonyl)phenyl sulfonyl]hydrazine-1-carboxamide;

N-2-(1,1,1,3,3,3-Hexafluoro-2-methylpropyl)-2-[(2-chlorophenyl)sulfonyl]hydrazine-1-carboxamide;

N-2-(1,1,1,3,3,3-Hexafluoro-2-methylpropyl)-2-[2-(5-morpholin-4-yl)pyridyl sulfonyl]hydrazine-1-carboxamide;

N-2-(1,1,1,3,3,3-Hexafluoro-2-methylpropyl)-2-[(2-trifluoromethoxyphenyl) sulfonyl]hydrazine-1-carboxamide;

N-2-(1,1,1,3,3,3-Hexafluoro-2-methylpropyl)-2-[(2,4-dichlorophenyl)sulfonyl]hydrazine-1-carboxamide;

N-2-(1,1,1,3,3,3-Hexafluoro-2-methylpropyl)-2-[phenylsulfonyl]hydrazine-1-carboxamide;

N-2-(1,1,1,3,3,3-Hexafluoro-2-methylpropyl)-2-[(3-difluoromethoxyphenyl)sulfonyl]hydrazine-1-carboxamide;

N-2-(1,1,1,3,3,3-Hexafluoro-2-methylpropyl)-2-[(3-cyanophenyl)sulfonyl]hydrazine-1-carboxamide;

N-2-(1,1,1,3,3,3-Hexafluoro-2-methylpropyl)-2-[(4-cyanophenyl)sulfonyl]hydrazine-1-carboxamide;

N-2-(1,1,1,3,3,3-Hexafluoro-2-methylpropyl)-2-[(5-(2,3-dihydrobenzo[1,4]dioxinyl) sulfonyl]hydrazine-1-carboxamide;

N-2-(1,1,1,3,3,3-Hexafluoro-2-methylpropyl)-2-[(4-methylphenyl)sulfonyl]-1-methylhydrazine-1-carboxamide;

N-2-(1,1,1,3,3,3-Hexafluoro-2-methylpropyl)-2-[(3-fluorophenyl)sulfonyl]hydrazine-1-carboxamide;

N-2-(1,1,1,3,3,3-Hexafluoro-2-methylpropyl)-2-[(3,4-difluorophenyl)sulfonyl]hydrazine-1-carboxamide;

N-2-(1,1,1,3,3,3-Hexafluoro-2-methylpropyl)-2-[(2,4-dimethylthiazol-5-yl)sulfonyl]hydrazine-1-carboxamide;

N-2-(1,1,1,3,3,3-Hexafluoro-2-methylpropyl)-2-[(4-acetylphenyl)sulfonyl]hydrazine-1-carboxamide;

N-2-(1,1,1,3,3,3-Hexafluoro-2-methylpropyl)-2-[(2,6-difluorophenyl)sulfonyl]hydrazine-1-carboxamide;

N-2-(1,1,1,3,3,3-Hexafluoro-2-methylpropyl)-2-[(2-fluorophenyl)sulfonyl]hydrazine-1-carboxamide;

N-2-(1,1,1,3,3,3-Hexafluoro-2-methylpropyl)-2-[(2,5-difluorophenyl)sulfonyl]hydrazine-1-carboxamide;

N-2-(1,1,1,3,3,3-Hexafluoro-2-methylpropyl)-2-[(4-methylphenyl)sulfonyl]-2-methylhydrazine-1-carboxamide;

N-2-(1,1,1,3,3,3-Hexafluoro-2-methylpropyl)-2-[(2,6-dichlorophenyl)sulfonyl]hydrazine-1-carboxamide;

N-2-(1,1,1,3,3,3-Hexafluoro-2-methylpropyl)-2-[(2,6-ditrifluoromethylphenyl)sulfonyl]hydrazine-1-carboxamide;

N-2-(1,1,1,3,3,3-Hexafluoro-2-methylpropyl)-2-[(4-methylphenyl)sulfonyl]hydrazine-1-methylcarboxamide;

N-2-(1,1,1,3,3,3-Hexafluoro-2-methylpropyl)-2-[(3,5-dimethylisoxazol-5-yl)sulfonyl]hydrazine-1-carboxamide;

N-2-(1,1,1,3,3,3-Hexafluoro-2-methylpropyl)-2-[(4-nitrophenyl)sulfonyl]hydrazine-1-carboxamide;

N-2-(1,1,1,3,3,3-Hexafluoro-2-methylpropyl)-2-[methylimidazol-4-yl)sulfonyl]hydrazine-1-carboxamide;

N-2-(1,1,1,3,3,3-Hexafluoro-2-methylpropyl)-2-[methylsulfonyl]hydrazine-1-carboxamide;

4-Phenylpiperazine-1-(2,2,2-trifluoro-1-methyl-1-trifluoromethylethyl)-carboxamide;

4-Morpholino-1-(2,2,2-trifluoro-1-methyl-1-trifluoromethylethyl)-carboxamide;

1-(2-Acetylphenyl)-3-(2,2,2-trifluoro-1-methyl-1-trifluoromethylethyl)-urea;

1-Piperidino-1-(2,2,2-trifluoro-1-methyl-1-trifluoromethylethyl)-carboxamide;

1-(2,2,2-trifluoro-1-methyl-1-trifluoromethylethyl)-3-(3,4,5-trimethoxyphenyl)-urea;

1-(4-Trifluoromethylphenyl)-3-(2,2,2-trifluoro-1-methyl-1-trifluoromethylethyl)-urea;

4-Methylpiperazine-1-(2,2,2-trifluoro-1-methyl-1-trifluoromethylethyl)-carboxamide;

1-Naphthalen-1-yl-3-(2,2,2-trifluoro-1-methyl-1-trifluoromethylethyl)-urea;

1-(4-Chlorophenyl)-3-(2,2,2-trifluoro-1-methyl-1-trifluoromethylethyl)-urea;

4-Phenylpiperidin-1-yl-1-(2,2,2-trifluoro-1-methyl-1-trifluoromethylethyl)-carboxamide;

1-(2-Phenyl(phenyl))-3-(2,2,2-trifluoro-1-methyl-1-trifluoromethylethyl)-urea;

1-(2,6-Difluorophenyl)-3-(2,2,2-trifluoro-1-methyl-1-trifluoromethylethyl)-urea;

2-[3-(1,1-Bis-trifluoromethylethyl)-ureido]benzamide;

1-(2-Chloro-6-fluorophenyl)-3-(2,2,2-trifluoro-1-methyl-1-trifluoromethylethyl)-urea;

1-(3-Trifluoromethylphenyl)-3-(2,2,2-trifluoro-1-methyl-1-trifluoromethylethyl)-urea;

2-[3-(1,1-Bis-trifluoromethylethyl)-ureido]benzenesulfonamide;

1-(2,2,3,3-Tetrafluoro-2,3-dihydrobenzo[1,4]dioxin-5-yl)-3-(2,2,2-trifluoro-1-methyl-1-trifluoromethylethyl)-urea;

1-(3-Trifluoromethoxyphenyl)-3-(2,2,2-trifluoro-1-methyl-1-trifluoromethylethyl)-urea;

1-(4-Trifluoromethoxyphenyl)-3-(2,2,2-trifluoro-1-methyl-1-trifluoromethylethyl)-urea;

4-Methyl-1-piperidine-1-(2,2,2-trifluoro-1-methyl-1-trifluoromethylethyl)-carboxamide;

1-Naphthalen-2-yl-3-(2,2,2-trifluoro-1-methyl-1-trifluoromethylethyl)-urea;

1-(2-fluorophenyl)-3-(2,2,2-trifluoro-1-methyl-1-trifluoromethylethyl)-urea;

1-(2,6-Dimethoxyphenyl)-3-(2,2,2-trifluoro-1-methyl-1-trifluoromethylethyl)-urea;

3-Trifluormethoxy-4-[3-(1,1-bis-trifluoromethylethyl)-ureido]benzoic acid;

1-Phenyl-3-(2,2,2-trifluoro-1-methyl-1-trifluoromethylethyl)-urea;

1-(3-Cyanophenyl)-3-(2,2,2-trifluoro-1-methyl-1-trifluoromethylethyl)-urea;

1-(3-Methoxyphenyl)-3-(2,2,2-trifluoro-1-methyl-1-trifluoromethylethyl)-urea;

1-(2-(1,1,2,2-Tetrafluoroethoxy)phenyl)-3-(2,2,2-trifluoro-1-methyl-1-trifluoromethylethyl)-urea;

3-[3-(1,1-Bis-trifluoromethylethyl)-ureido]benzenesulfonamide;

1-(3-fluorophenyl)-3-(2,2,2-trifluoro-1-methyl-1-trifluoromethylethyl)-urea;

1-(4-Bromophenyl)-3-(2,2,2-trifluoro-1-methyl-1-trifluoromethylethyl)-urea;

1-(2-Cyanophenyl)-3-(2,2,2-trifluoro-1-methyl-1-trifluoromethylethyl)-urea;

1-(4-Cyanophenyl)-3-(2,2,2-trifluoro-1-methyl-1-trifluoromethylethyl)-urea;

1-(2,2-Difluorobenzo[1,3]dioxol-4-yl)-3-(2,2,2-trifluoro-1-methyl-1-trifluoromethylethyl)-urea;

1-(4-Chlorophenyl)-3-(2,2,2-trifluoro-1-methyl-1-trifluoromethylethyl)-urea;

1-(3-Methylphenyl)-3-(2,2,2-trifluoro-1-methyl-1-trifluoromethylethyl)-urea;

4-[3-(1,1-Bis-trifluoromethylethyl)-ureido]benzenesulfonamide;

1-(2,6-Dibromophenyl)-3-(2,2,2-trifluoro-1-methyl-1-trifluoromethylethyl)-urea;

1-(2-Methylphenyl)-3-(2,2,2-trifluoro-1-methyl-1-trifluoromethylethyl)-urea;

1-(4-Methylphenyl)-3-(2,2,2-trifluoro-1-methyl-1-trifluoromethylethyl)-urea;

1-Pyrrolidinyl-1-(2,2,2-trifluoro-1-methyl-1-trifluoromethylethyl)-carboxamide;

1-(4-Fluorophenyl)-3-(2,2,2-trifluoro-1-methyl-1 fluoromethylethyl)-urea;

1-(2,4-Dibromophenyl)-3-(2,2,2-trifluoro-1-methyl-1-trifluoromethylethyl)-urea;

Azepane-1-carboxylic acid (2,2,2-trifluoro-1-methyl-1-trifluoromethylethyl)-amide;

1-(4-Bromo-2-trifluoromethoxyphenyl)-3-(2,2,2-trifluoro-1-methyl-1-trifluoromethylethyl)-urea;

1-(2-Trifluoromethoxyphenyl)-3-(2,2,2-trifluoro-1-methyl-1-trifluoromethylethyl)-urea;

1-(2-Trifluoromethylphenyl)-3-(2,2,2-trifluoro-1-methyl-1-trifluoromethylethyl)-urea;

1-(2-Methoxyphenyl)-3-(2,2,2-trifluoro-1-methyl-1-trifluoromethylethyl)-urea; and N-2-(1,1,1,3,3,3-hexafluoro-1-methylpropyl)-2-[(4-difluoromethoxyphenyl)sulfonyl]hydrazine-1-carboxamide.

In another embodiment provide herein is a method for the treatment or prophylaxis of a viral infection or disease associated therewith, comprising administering in a therapeutically effective amount to a mammal in need thereof, a compound of Formula II or a pharmaceutically-acceptable salt thereof. In another embodiment, a pharmaceutical composition that comprises a pharmaceutically-effective amount of the compound or a pharmaceutically-acceptable salt thereof, and a pharmaceutically-acceptable carrier is provided. In addition, compounds of Formula II, as well as pharmaceutically-acceptable salts thereof are provided.

Compounds of Formula II include:

Formula II

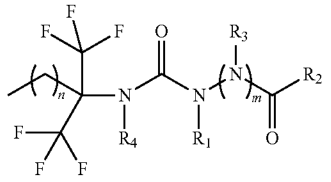

wherein n is an integer from 0-6;

m is an integer from 0-1;

$R_1$ is selected from the group consisting of H and alkyl;

$R_2$ is selected from the group consisting of substituted or unsubstituted phenyl, substituted and unsubstituted aryl, substituted and unsubstituted heteroaryl, substituted or unsubstituted alkyl, substituted or unsubstituted branched alkyl, and substituted or unsubstituted unsaturated cycloheteroalkyls;

or where $R_1$ and $R_2$ combine together to form a substituted or unsubstituted $C_{4-10}$ cyclic saturated heteroalkyl;

$R_3$ and $R_4$ are independently selected from the group consisting of H and alkyl;

or a pharmaceutically-acceptable salt thereof.

In particular, certain embodiments relate to a compound of Formula II selected from the group consisting of:

2-[2,5-bis(2,2,2-trifluoroethoxy)benzoyl]-N-[1,1-bis(trifluoromethyl)propyl]hydrazinecarboxamide;

N-[1,1-bis(trifluoromethyl)propyl]-2-(4-tert-butylbenzoyl)hydrazinecarboxamide;

2-(1,1'-biphenyl-4-ylcarbonyl)-N-[1,1-bis(trifluoromethyl)propyl]hydrazinecarboxamide;

N-[1,1-bis(trifluoromethyl)propyl]-2-(4-naphthoyl)hydrazinecarboxamide;

2-(1,1'-biphenyl-2-ylcarbonyl)-N-[1,1-bis(trifluoromethyl)propyl]hydrazinecarboxamide;

N-[1,1-bis(trifluoromethyl)propyl]-2-(4-methylbenzoyl)hydrazinecarboxamide;

N-[1,1-bis(trifluoromethyl)propyl)-2-(2-naphthoyl)hydrazinecarboxamide;

N-(1,1-bis(trifluoromethyl)propyl]-2-(2,5-dimethoxybenzoyl)hydrazinecarboxamide;

N-[1,1-bis(trifluoromethyl)propyl]-2-(3,4-dichlorobenzoyl)hydrazinecarboxamide;

N-[1,1-bis(trifluoromethyl)propyl]-2-(4-bromobenzoyl)hydrazinecarboxamide;

N-[1,1-bis(trifluoromethyl)propyl]-2-(4-isopropylbenzoyl)hydrazinecarboxamide;

N-[1,1-bis(trifluoromethyl)propyl]-2-(3,5-dimethylbenzoyl)hydrazinecarboxamide;

N-[1,1-bis(trifluoromethyl)propyl]-2-(mesitylcarbonyl)hydrazinecarboxamide; and

N-[1,1-bis(trifluoromethyl)propyl]-2-(5-chloro-2-methoxybenzoyl)hydrazinecarboxamide.

In an embodiment, the mammal being treated is a human. In particular embodiments, the viral infection being treated is a hemorrhagic fever virus, such as an Arenavirus. The Arenavirus may be selected from the group consisting of Junin, Machupo, Guanarito, Sabia, Lassa, Tacaribe, Pinchinde, and VSV. Details of methods and formulations are more fully described below.

BRIEF DESCRIPTION OF THE SEVERAL VIEWS OF THE DRAWINGS

FIG. 2 shows the effect of the time of addition of ST-336 on Tacaribe virus yield and plaque formation.

FIG. 3 shows that ST-336 binds with slow $K_{off}$ to intact Tacaribe virion in the absence of cells.

FIG. 4 shows the mapping of ST-336 drug resistant variants ("DRVs"). FIG. 4B discloses SEQ ID NOS 3, 3, 3, 3 and 4-13, respectively, in order of appearance.

DETAILED DESCRIPTION

Figure 1:
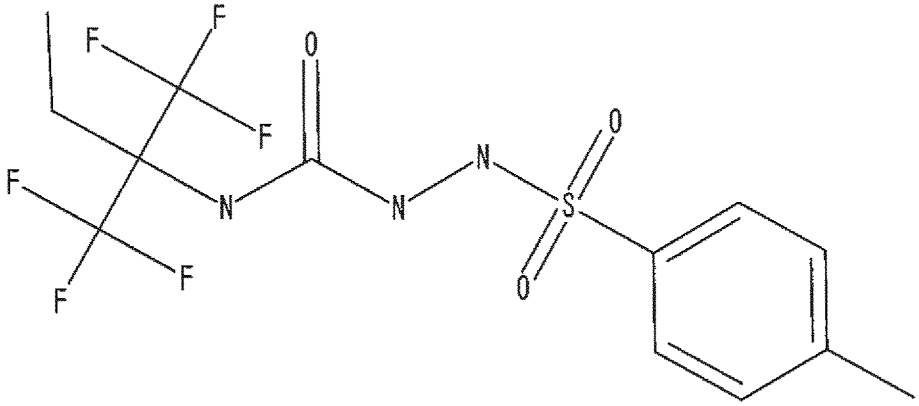
FIG. 1 provides the chemical structure, formula, and molecular weight of ST-336.

Compounds which are useful for the treatment and prophylaxis of viral infections, as well as diseases associated with viral infections in living hosts, are provided. In particular, provided are compounds and compositions and/or methods for the treatment and prophylaxis of hemorrhagic fever viruses, such as Arenaviruses. However, prior to providing further detail, the following terms will first be defined.

DEFINITIONS

In accordance with this detailed description, the following abbreviations and definitions apply. It must be noted that as used herein, the singular forms "a," "an," and "the" include plural referents unless the context clearly dictates otherwise.

The publications discussed herein are provided solely for their disclosure. Nothing herein is to be construed as an admission regarding antedating the publications. Further, the dates of publication provided may be different from the actual publication dates, which may need to be independently confirmed.

Where a range of values is provided, it is understood that each intervening value is encompassed. The upper and lower limits of these smaller ranges may independently be included in the smaller, subject to any specifically-excluded limit in the stated range. Where the stated range includes one or both of the limits, ranges excluding either both of those included limits are also included in the invention. Also contemplated are any values that fall within the cited ranges.

Unless defined otherwise, all technical and scientific terms used herein have the same meaning as commonly understood by one of ordinary skill in the art. Any methods and materials similar or equivalent to those described herein can also be used in practice or testing. All publications mentioned herein are incorporated herein by reference to disclose and describe the methods and/or materials in connection with which the publications are cited.

By "patient" or "subject" is meant to include any mammal. A "mammal," for purposes of treatment, refers to any animal classified as a mammal, including but not limited to, humans, domestic and farm animals, and zoo, sports, or pet animals, such as dogs, horses, cats, cows, rats, mice, guinea pigs and the like.

The term "efficacy" as used herein in the context of a chronic dosage regime refers to the effectiveness of a particular treatment regime. Efficacy can be measured based on change of the course of the disease in response to an agent.

The term "success" as used herein in the context of a chronic treatment regime refers to the effectiveness of a particular treatment regime. This includes a balance of efficacy, toxicity (e.g., side effects and patient tolerance of a formulation or dosage unit), patient compliance, and the like. For a chronic administration regime to be considered "successful" it must balance different aspects of patient care and efficacy to produce a favorable patient outcome.

The terms "treating," "treatment," and the like are used herein to refer to obtaining a desired pharmacological and physiological effect. The effect may be prophylactic in terms of preventing or partially preventing a disease, symptom, or condition thereof and/or may be therapeutic in terms of a partial or complete cure of a disease, condition, symptom, or adverse effect attributed to the disease. The terms "treating" and "treatment," as used herein, covers any treatment of a disease in a mammal, such as a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; and (c) relieving the disease, i.e., causing regression of the disease and/or its symptoms or conditions. Treating a patient's suffering from disease related to pathological inflammation is contemplated. Preventing, inhibiting, or relieving adverse effects attributed to pathological inflammation over long periods of time and/or are such caused by the physiological responses to inappropriate inflammation present in a biological system over long periods of time are also contemplated.

As used herein, "acyl" refers to the groups H—C(O)—, alkyl-C(O)—, substituted alkyl-C(O)—, alkenyl-C(O)—, substituted alkenyl-C(O)—, alkynyl-C(O)-, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Lower alkenyl" refers to an alkenyl group preferably having from 2 to 6 carbon atoms and having at least 1 site and preferably only I site of alkenyl unsaturation (i.e., >C═C<). This term is exemplified by groups such as allyl, ethenyl, propenyl, butenyl, and the like.

"Substituted alkenyl" refers to alkenyl groups having from 1 to 5 substituents independently selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidine, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, cycloalkyloxy, substituted cycloalkyloxy, heteroaryloxy, substituted heteroaryloxy, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —NRS(O)-2-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Alkoxy" refers to the group "alkyl-O-" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—."

"Alkyl" refers to linear or branched alkyl groups having from 1 to 10 carbon atoms, alternatively 1 to 6 carbon atoms. This term is exemplified by groups such as methyl, t-butyl, n-heptyl, octyl and the like.

"Lower alkyl" refers to monovalent alkyl groups having from 1 to 5 carbon atoms including straight and branched chain alkyl groups. This term is exemplified by groups such as methyl, ethyl, iso-propyl, n-propyl, n-butyl, iso-butyl, sec-butyl, (-butyl, n-pentyl and the like. "Lower alkyl" may be optionally substituted with a halogen, such as chloro, fluoro, bromo, and the like.

"Substituted alkyl" refers to an alkyl group, of from 1 to 10 carbon atoms, having from 1 to 5 substituents independently selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, cycloalkyloxy, substituted cycloalkyloxy, heteroaryloxy, substituted heteroaryloxy, —OS(O)2-alkyl, —OS(O)2-substituted alkyl, —$OS(O)_2$-aryl, —OS(O)-2-substituted aryl, —OS(O)-2-heteroaryl, —$OS(O)_2$-substituted heteroaryl, —OS(O)-2-heterocyclic, —$OS(O)_2$-substituted heterocyclic, —$OSO_2$—NRR where R is hydrogen or alkyl, —NRS(O)-2-alkyl, —$NRS(O)_2$-substituted alkyl, —NRS(O)-2-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkylamino, mono- and di-arylamino, mono- and di-substituted arylamino, mono- and di-heteroarylamino, monoand di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Amidino" refers to the group $H_2$NC(═NH)— and the term "alkylamidino" refers to compounds having 1 to 3 alkyl groups (e.g., alkylHNC(═NH)—).

"Amino" refers to the group —$NH_2$.

"Substituted amino" refers to the group —NRR, where each R group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, provided that both R groups are not hydrogen; or the R groups can be joined together with the nitrogen atom to form a heterocyclic or substituted heterocyclic ring.

"Aminoacyl" refers to the groups —NRC(O)alkyl, —NRC(O)substituted alkyl, NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like) provided that the point of attachment is through an aromatic ring atom.

"Substituted aryl" refers to aryl groups which are substituted with from Ito 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl I, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)-2-alkyl, —$S(O)_2$-substituted alkyl, —$S(O)_2$-cycloalkyl, —$S(O)_2$-substituted cycloalkyl, —S(O)-2-alkenyl, —S(O)-2-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —$OS(O)_2$-alkyl, —OS(O)-2-substituted alkyl, —$OS(O)_2$-aryl, —$OS(O)_2$-substituted aryl, —OS(O)-2-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —NRS(O)-2-substituted alkyl, —$NRS(O)_2$-aryl, —NRS(O)-2-substituted aryl, —$NRS(O)_2$-heteroaryl, —NRS(O)-2-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2$NRR where R is hydrogen or alkyl.

"Cycloalkenyl" refers to cyclic alkenyl groups of from 3 to 8 carbon atoms having single or multiple unsaturation but which are not aromatic.

"Cycloalkoxy" refers to —O-cycloalkyl groups.

"Substituted cycloalkoxy" refers to —O-substituted cycloalkyl groups.

"Cycloalkyl," with regard to the compounds of Formulae I and II and the PEG derivatives, refers to cyclic alkyl groups of from 3 to 12 carbon atoms having a single or multiple condensed rings including, by way of example, adamantyl, cyclopropyl, cyclobutyl, cyclopentyl, cyclohexyl, cyclooctyl and the like.

"Cycloalkyl" refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Lower cycloalkyl" refers to cyclic alkyl groups of from 3 to 6 carbon atoms having a single cyclic ring including, by way of example, cyclopropyl, cyclobutyl, cyclopentyl and cyclohexyl.

"Substituted cycloalkyl" and "substituted cycloalkenyl" refers to a cycloalkyl or cycloalkenyl group, typically of from 3 to 8 carbon atoms, having from 1 to 5 substituents independently selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS$(O)_2$-alkyl, —OS$(O)_2$-substituted alkyl, —OS$(O)_2$-aryl, —OS$(O)_2$-substituted aryl, —OS$(O)_2$-heteroaryl, —OS$(O)_2$-substituted heteroaryl, —OS$(O)_2$-heterocyclic, —OS$(O)_2$-substituted heterocyclic, —$OSO_2$—NRR where R is hydrogen or alkyl, —NRS$(O)_2$-alkyl, —NRS$(O)_2$-substituted alkyl, —NRS(O)-2-aryl, —NRS$(O)_2$-substituted aryl, —NRS$(O)_2$-heteroaryl, —NRS$(O)_2$-substituted heteroaryl, —NRS$(O)_2$-heterocyclic, —NRS$(O)_2$-substituted heterocyclic, —NRS$(O)_2$—NR-alkyl, —NRS$(O)_2$—NR-substituted alkyl, —NRS$(O)_2$—NR-aryl, —NRS$(O)_2$—NR-substituted aryl, —NRS$(O)_2$—NR-heteroaryl, —NRS$(O)_2$—NR-substituted heteroaryl, —NRS$(O)_2$—NR-heterocyclic, —NRS$(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

“Halo” or “halogen” refers to fluoro, chloro, bromo and iodo.

“Heteroaryl” refers to an aromatic carbocyclic group of from 2 to 10 carbon atoms and 1 to 4 heteroatoms selected from the group consisting of oxygen, nitrogen and sulfur within the ring or oxides thereof. Such heteroaryl groups can have a single ring (e.g., pyridyl or furyl) or multiple condensed rings (e.g., indolizinyl or benzothienyl) wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Additionally, the carbon atoms of the ring may be substituted with an oxo (═O). The term “heteroaryl having two nitrogen atoms in the heteroaryl ring” refers to a heteroaryl group having two, and only two, nitrogen atoms in the heteroaryl ring and optionally containing 1 or 2 other heteroatoms in the heteroaryl ring, such as oxygen or sulfur.

“Substituted heteroaryl” refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$S(O)_2$-alkyl, —$S(O)_2$-substituted alkyl, —S(O)-2-cycloalkyl, —$S(O)_2$-substituted cycloalkyl, —$S(O)_2$-alkenyl, —$S(O)_2$-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —OS(O)-2-alkyl, —OS$(O)_2$-substituted alkyl, —OS$(O)_2$-aryl, —OS$(O)_2$-substituted aryl, —OS$(O)_2$-heteroaryl, —OS$(O)_2$-substituted heteroaryl, —OS$(O)_2$-heterocyclic, —OS$(O)_2$-substituted heterocyclic, —$OSO_2$—NRR where R is hydrogen or alkyl, —NRS$(O)_2$-alkyl, —NRS(O)-2-substituted alkyl, —NRS$(O)_2$-aryl, —NRS$(O)_2$-substituted aryl, —NRS$(O)_2$-heteroaryl, —NRS$(O)_2$-substituted heteroaryl, —NRS$(O)_2$-heterocyclic, —NRS$(O)_2$-substituted heterocyclic, —NRS$(O)_2$—NR-alkyl, —NRS$(O)_2$—NR-substituted alkyl, —NRS$(O)_2$—NR-aryl, —NRS$(O)_2$—NR-substituted aryl, —NRS$(O)_2$—NR-heteroaryl, —NRS$(O)_2$—NR-substituted heteroaryl, —NRS$(O)_2$—NR-heterocyclic, —NRS$(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2$NRR where R is hydrogen or alkyl.

“Heteroaryloxy” refers to the group —O-heteroaryl and “substituted heteroaryloxy” refers to the group —O-substituted heteroaryl.

“Heteroaralkoxy” refers to the group heteroaryl-alkylene-O—.

“Substituted heteroaralkoxy” refers to the group substituted heteroaryl-alkylene-O—.

“Heterocycle” or “heterocyclic” refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking group: such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, morpholinyl, thiomorpholino, thiomorpholinyl (also referred to as thiamorpholinyl), piperidinyl, pyrrolidine, tetrahydrofuranyl, and the like.

"Optionally substituted" means that the recited group may be unsubstituted or the recited group may be substituted.

"Pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use. A pharmaceutically-acceptable carrier or excipient includes both one or more than one of such carriers.

"Pharmaceutically-acceptable cation" refers to the cation of a pharmaceutically-acceptable salt.

"Pharmaceutically-acceptable salt" refers to salts which retain the biological effectiveness and properties of compounds which are not biologically or otherwise undesirable. Pharmaceutically-acceptable salts refer to pharmaceutically-acceptable salts of the compounds, which salts are are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl a mines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

Pharmaceutically-acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

A compound may act as a pro-drug. Pro-drug means any compound which releases an active parent drug in vivo when such pro-drug is administered to a mammalian subject. Pro-drugs are prepared by modifying functional groups present in such a way that the modifications may be cleaved in vivo to release the parent compound. Prodrugs include compounds wherein a hydroxy, amino, or sulfhydryl group is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylamino-carbonyl) of hydroxy functional groups, and the like.

A "therapeutically-effective amount" means the amount of a compound or antibody that, when administered to a mammal for treating a disease, is sufficient to effect such treatment for the disease. The "therapeutically-effective amount" will vary depending on the compound, the disease, and its severity and the age, weight, etc., of the mammal to be treated.

Pharmaceutical Formulations of the Compounds

In general, compounds will be administered in a therapeutically-effective amount by any of the accepted modes of administration for these compounds. The compounds can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compounds can be administered continuously by infusion or by bolus injection.

The actual amount of the compound, i.e., the active ingredient, will depend on a number of factors, such as the severity of the disease, i.e., the condition or disease to be treated, age, and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compounds lies within a range of circulating concentrations that include the $ED_{50}$ with little or no toxicity. The dosage may vary within this range depending upon the dosage form employed and the route of administration utilized. For any compound used, the therapeutically-effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The amount of the pharmaceutical composition administered to the patient wil vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically-effective dose." Amounts effective for this use will depend on the disease condition being treated as well as by the judgment of the attending clinician depending upon factors such as the severity of the inflammation, the age, weight, and general condition of the patient, and the like.

The compositions administered to a patient are in the form of pharmaceutical compositions described supra. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. It will be understood that use of certain of the foregoing excipients, carriers, or stabilizers will result in the formation of pharmaceutical salts.

The active compound is effective over a wide dosage range and is generally administered in a pharmaceutically- or therapeutically-effective amount. The therapeutic dosage of the compounds will vary according to, for example, the particular use for which the treatment is made, the manner of administration of the compound, the health and condition of the patient, and the judgment of the prescribing physician. For example, for intravenous administration, the dose will typically be in the range of about 0.5 mg to about 100 mg per kilogram body weight. Effective doses can be extrapolated from dose-response curves derived from in vitro or animal model test systems. Typically, the clinician will administer the compound until a dosage is reached that achieves the desired effect.

When employed as pharmaceuticals, the compounds are usually administered in the form of pharmaceutical compositions. Pharmaceutical compositions contain as the active ingredient one or more of the compounds above, associated with one or more pharmaceutically-acceptable carriers or excipients. The excipient employed is typically one suitable for administration to human subjects or other mammals. In making the compositions, the active ingredient is usually mixed with an excipient, diluted by an excipient, or enclosed within a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained, or delayed-release of the active ingredient after administration to the patient by employing procedures known in the art.

The quantity of active compound in the pharmaceutical composition and unit dosage form thereof may be varied or adjusted widely depending upon the particular application, the manner or introduction, the potency of the particular compound, and the desired concentration. The term "unit dosage forms" refers to physically-discrete units suitable as unitary dosages for human subjects and other mammals, each unit containing a predetermined quantity of active material calculated to produce the desired therapeutic effect, in association with a suitable pharmaceutical excipient.

The compound can be formulated for parenteral administration in a suitable inert carrier, such as a sterile physiological saline solution. The dose administered will be determined by route of administration.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost-effective. All of these factors ultimately determine the overall success and usefulness of an intravenous formulation.

Other accessory additives that may be included in pharmaceutical formulations and compounds as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer may be necessary to maintain the aqueous pH in the range of from about 4 to about 8. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer: alendronate (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

A useful buffer is sodium citrate/citric acid in the range of 5 to 50 mg per ml sodium citrate to 1 to 15 mg per ml citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

An intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient.

The tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically-acceptable, aqueous or organic solvents, or mixtures thereof, and powders. The liquid or solid compositions may contain suitable pharmaceutically-acceptable excipients as described supra. Compositions in pharmaceutically-acceptable solvents may be nebulized by use of inert gases. Nebulized solutions may be breathed directly from the nebulizing device or the nebulizing device may be attached to a face mask tent, or intermittent positive pressure breathing machine. Solution, suspension, or powder compositions may be administered from devices which deliver the formulation in an appropriate manner.

The compounds can be administered in a sustained release form. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly(vinyl alcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et ah, supra), degradable lactic acid-glycolic acid copolymers such as the LUPRON DEPOT™ (i.e., injectable microspheres composed of lactic acid-glycolic acid copolymer and leuprolide acetate), and poly-D-(−)-3-hydroxybutyric acid (EP 133,988).

The compounds can be administered in a sustained-release form, for example a depot injection, implant preparation, or osmotic pump, which can be formulated in such a manner as to permit a sustained-release of the active ingredient. Implants for sustained-release formulations are well-known in the art implants may be formulated as, including but not limited to, microspheres, slabs, with biodegradable or non-biodegradable polymers. For example, polymers of lactic acid and/or glycolic acid form an erodible polymer that is well-tolerated by the host.

The following formulation examples illustrate pharmaceutical compositions.

Formulation Example I

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/capsule) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/capsule) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium Carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules, which after mixing, are compressed on a tablet machine to yield tablets each weighing 150 mg.

Formulation Example 5

Capsules, each containing 40 mg of medicament, are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Formulation Example 6

Suppositories, each containing 25 mg of active ingredient, are made as follows:

| Ingredient | Amount |
|---|---|
| Active Ingredient | 25 mg |
| Saturated fatty acids glycerides | to 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose, are made as follows:

| Ingredient | Amount |
|---|---|
| Active Ingredient | 50.0 mg |
| Xanthan gum | 4.0 mg |
| Sodium carboxymethyl cellose (11%) | |
| Microcrystalline cellulose (89%) | 500 mg |
| Sucrose | 1.75 g |
| Sodium benzoate | 10.0 mg |
| Flavor and color | q.v. |
| Purified water | to 5.0 ml |

The medicament, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Hard gelatin tablets, each containing 15 mg of active ingredient, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
|---|---|
| Active Ingredient | 250.0 mg |
| Isotonic saline | 1000 ml |

Therapeutic compound compositions generally are placed into a container having a sterile access port, for example, an intravenous solution bag or vial having a stopper pierceable by a hypodermic injection needle or similar sharp instrument.

Formulation Example 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

An aerosol formulation may be prepared as follows: A solution of the candidate compound in 0.5% sodium bicarbonate/saline (w/v) at a concentration of 30.0 mg/ml is prepared using the following procedure:

| A. Preparation of 0.5% Sodium Bicarbonate/ Saline Stock Solution: 100.0 ml | | |
|---|---|---|
| Ingredient | Gram /100.0 ml | Final Concentration |
| Sodium Bicarbonate | 0.5 g | 0.5% |
| Saline | q.s. ad 100.0 ml | q.s. ad 100% |

Procedure:

1. Add 0.5 g sodium bicarbonate into a 100 ml volumetric flask.
2. Add approximately 90.0 ml saline and sonicate until dissolved.
3. Q.S. to 100.0 ml with saline and mix thoroughly.

| B. Preparation of 30.0 mg/ml Candidate Compound: 10.0 ml | | |
|---|---|---|
| Ingredient | Gram /10.0 ml | Final Concentration |
| Candidate Compound | 0.300 g | 30.0 mg/ml |
| 0.5% Sodium Bicarbonate/ Saline Stock Solution | q.s. ad 10.0 ml | q.s ad 100% |

Procedure:

1. Add 0.300 g of the candidate compound into a 10.0 ml volumetric flask.
2. Add approximately 9.7 ml of 0.5% sodium bicarbonate/ saline stock solution.
3. Sonicate until the candidate compound is completely dissolved.
4. Q.S. to 10.0 ml with 0.5% sodium bicarbonate/saline stock solution and mix Transdermal delivery devices ("patches") may also be employed. Such transdermal patches may be used to provide continuous or discontinuous infusion of the compounds in controlled amounts. The construction and use of transdermal patches for the delivery of pharmaceutical agents is well known in the art. See, e.g., U.S. Pat. No. 5,023,252, issued Jun. 11, 1991, incorporated herein by reference. Such patches may be constructed for continuous, pulsatile, or on-demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid-soluble and amenable to transportation across the blood-brain barrier. Alternatively, the delivery of hydrophilic drugs may be enhanced by intra-arterial infusion of hypertonic solutions which can transiently open the blood-brain barrier.

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

Pharmaceutical compositions are suitable for use in a variety of drug delivery systems. Suitable formulations for use in the present invention are found in *Remington's Pharmaceutical Sciences*, Mace Publishing Company, Philadelphia, Pa., 17th ed. (1985).

Utility

The provided compounds and pharmaceutical compositions show biological activity in treating and preventing viral infections and associated diseases, and, accordingly, have utility in treating viral infections and associated diseases, such as hemorrhagic fever viruses, in mammals including humans.

Hemorrhagic fever viruses (HFVs) are RNA viruses that cause a variety of disease syndromes with similar clinical characteristics. HFVs that are of concern as potential biological weapons include but are not limited to Arenaviridae (Junin, Machupo, Guanarito, Sabia, Lassa, Tacaribe, Pinchinde, and VSV), Filoviridae (ebola and Marburg viruses), Flaviviridae (yellow fever, omsk hemorrhagic fever and Kyasanur Forest disease viruses), and Bunyaviridae (Rift Valley fever). The naturally-occurring arenaviruses and potential engineered arenaviruses are included in the Category A Pathogen list according to the Center for Disease Control and Prevention as being among those agents that have greatest potential for mass casualties.

Risk factors include: travel to Africa or Asia, handling of animal carcasses, contact with infected animals or people, and/orarthropod bites. Arenaviruses are highly infectious after direct contact with infected blood and/or bodily secretions. Humans usually become infected through contact with infected rodents, the bite of an infected arthropod, direct contact with animal carcasses, inhalation of infectious rodent excreta and/or injection of food contaminated with rodent excreta. The Tacaribe virus has been associated with bats. Airborne transmission of hemorrhagic fever is another mode, but somewhat less common. Person-to-person contact may also occur in some cases.

All of the hemorrhagic fevers exhibit similar clinical symptoms. However, in general the clinical manifestations are non-specific and variable. The incubation period is approximately 7-14 days. The onset is gradual with fever and malaise, tachypnea, relative bradycardia, hypotension, circulatory shock, conjeunctival injection, pharyngitis, lymphadenopathy, encephalitis, myalgia, back pain, headache and dizziness, as well as hyperesthesia of the skin. Some infected patients may not develop hemorrhagic manifestations.

Methods of diagnosis at specialized laboratories include antigen detection by antigen-capture enzyme-linked immunosorbent assay (ELISA), IgM antibody detection by antibody-capture enzyme-linked immunosorbent assay, reverse transcriptase polymerase chain reaction (RT-PCR), and viral isolation. Antigen detection (by enzyme-linked immunosorbent assay) and reverse transcriptase polymerase chain reaction are the most useful diagnostic techniques in the acute clinical setting. Viral isolation is of limited value because it requires a biosafety level 4 (BSL-4) laboratory.

EXAMPLES

Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric. Abbreviations not defined above take their generally accepted meaning.

Synthesis of Compounds

The compounds are readily prepared via several divergent synthetic routes with the particular route selected relative to the ease of compound preparation, the commercial availability of starting materials, and the like.

The compounds can be prepared from readily-available starting materials using the following general methods and procedures. ft will be appreciated that where process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included unless otherwise indicated. Pure stereoisomers (or enriched mixtures) may be prepared using, for example, optically-active starting materials or stereoselective reagents well-known in the art. Alternatively, racemic mixtures of such compounds can be separated using, for example, chiral column chromatography, chiral resolving agents, and the like.

Unless otherwise indicated, the products are a mixture of R, S enantiomers. However, when a chiral product is desired, the chiral product can be obtained via purification techniques which separate enantiomers from a R, S mixture to provide for one or the other stereoisomer. Such techniques are known in the art.

In another embodiment, the compounds can be provided as pro-drugs which convert (e.g., hydrolyze, metabolize, etc.) in vivo to a compound above.

The following Methods were used to prepare the compounds set forth below as indicated.

Examples 1-12, 14-45, 47-50

The compounds of Examples 1-50 were prepared following the below-mentioned general procedure for Example 13 using compound 13 (a) and reacting it with the following benzenesulfonylhydrazines: 4-Phenylbenzenesulfonyl hydrazine, 4-t-butylbenzenesulfonyl hydrazine, 4-methyl-3,4-dihydro-2,7-benzo[1,4]oxazine-7-sulfonyl hydrazine, 5-(1-dimethylaminonaphthyl)sulfonyl hydrazine, 2,4,6-trimethylbenzenesulfonyl hydrazine, 3-chloro-6-methoxybenzenesulfonyl hydrazine, 2,5-dimethoxybenzenesulfonyl hydrazine, 4-(4-[1,2,3]thiadiazolyl)benzenesulfonyl hydrazine, 3-bromobenzenesulfonylhydrazine, 4-bromobenzenesulfonyl hydrazine, 4-methylbenzenesulfonyl hydrazine, 4-methoxybenzenesulfonyl hydrazine, 3-fluoro-4-chlorobenzenesulfonyl hydrazine, 4-trifluoromethoxybenzenesulfonyl hydrazine, 4-fluorobenzenesulfonyl hydrazine, 3-methoxybenzenesulfonyl hydrazine, 2-methylbenzenesulfonyl hydrazine, 3-trifluoromethylbenzenesulfonyl hydrazine, 2,4-dimethoxybenzenesulfonyl hydrazine, 5-chloro-1,3-dimethyl-1H-pyrazolylsulfonyl hydrazine, 3-methylbenzenesulfonyl hydrazine, 4-trifluoromethylbenzenesulfonyl hydrazine, 2-trifluoromethylbenzenesulfonyl hydrazine, 4-(pyrrolidin-1-sulfonyl)benzenesulfonyl hydrazine, 2-chlorobenzenesulfonyl hydrazine, 5-(2-morpholin-4-yl)pyridylsulfonyl hydrazine, 2-trifluoromethoxybenzenesulfonyl hydrazine, 2,4-dichlorobenzenesulfonyl hydrazine; benzenesulfonyl hydrazine, 3-difluoromethylbenzenesulfonyl hydrazine, 3-cyanobenzenesulfonyl hydrazine, 4-cyanobenzenesulfonyl hydrazine, 5-(2,3-dihydrobenzo[1,4]dioxinyl)sulfonyl hydrazine, 2-(4-methylbenzenesulfonyl)-1-methyl hydrazine, 3-fluorobenzenesulfonyl hydrazine, 3,4-difluorobenzenesulfonyl hydrazine, 2,4-dimethylthiazol-5-ylsulfonyl hydrazine, 4-acetylbenzenesulfonyl hydrazine, 2,6-difluorobenzenesulfonyl hydrazine, 2-fluorobenzenesulfonyl hydrazine, 2,5-difluorobenzenesulfonyl hydrazine, 1-(4-methylbenzenesulfonyl)-1-methyl hydrazine, 2,6-dichlorobenzenesulfonyl hydrazine, 2,6-ditrifluoromethylbenzenesulfonyl hydrazine, 3,5-dimethylisoxazol-5-ylsulfonyl hydrazine, 4-nitrobenzenesulfonyl hydrazine, (1-methylimidazol-4-yl)sulfonyl hydrazine, and methylsulfonyl hydrazine.

Example 13

Preparation of N-2-(1,1,1,3,3,3-Hexafluoro-2-methylpropyl)-2-[(4-difluoromethoxyphenyl)sulfonyl]hydrazine-1-carboxamide a. Preparation of 1,1,1,3,3,3-Hexafluoro-2-isocyanato-2-methylpropane, compound 13(a)

13(a)

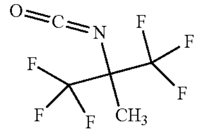

A solution of trimethylsilylazide (26 ml, 180 mmol) was slowly added dropwise to a solution of 2,2-bis(trifluoromethyl)propionyl fluoride (38 g, 179 mmol) and benzyltriethylammonium chloride (0.065 g, 0.28 mmol) in xylenes (120 ml) at 0° C. Upon completion of the addition, the resulting mixture was heated at 110° C. After 4 h, the mixture was distilled at 760 mm Hg, and the fraction boiling at 40-50° C. contained 13(a). Yield of the liquid product is 60%.

b. Preparation of N-2-(1,1,1,3,3,3-Hexafluoro-2-methylpropyl)-2-[(4-difluoromethoxyphenyl)sulfonyl]hydrazine-1-carboxamide

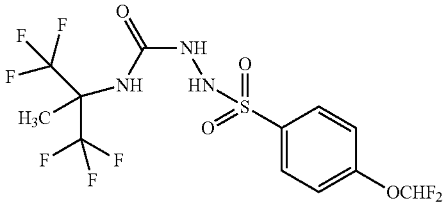

13

To a solution of 4-difluorobenzenesulfonyl chloride (60 mg, 0.25 mmol) in methylamine (25 mg, 0.25 mmol) in 1 ml of dry THF was added anhydrous hydrazine (15 mg, 0.26 mmol) at room temperature. After stirring at room temperature for 2 h, a solution of 1,1,1,3,3,3-hexafluoro-2-isocyanato-2-methylpropane (13a) (54 mg, 0.26 mmol) in 1 ml of diethylether. The reaction mixture was stirred at room temperature for 12 h. The solvent was removed in vacuo, and the crude material subjected to reverse phase HPLC affording the product as a white, waxy solid (83 mg, 75%).

Example 46

Preparation of N-2-(1,1,1,3,3,3-Hexafluoro-2-methylpropyl)-2-[(4-methylphenyl)sulfonyl]hydrazine-1-methylcarboxamide

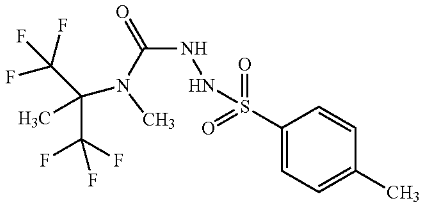 [SMILES: Cc1ccc(S(=O)(=O)NNC(=O)N(C)C(C)(C(F)(F)F)C(F)(F)F)cc1]

To a solution of N-2-(1,1,1,3,3,3-Hexafluoro-2-methylpropyl)-2-[(4-methylphenyl)sulfonyl]hydrazine-1-carboxamide (100 mg, 0.254 mmol) prepared as described above, and cesium carbonate (165 mg, 0.51 mmol) in 1.6 ml of NMP was added iodomethane (17.5 yL, 0.28 mmol). The yellow mixture was stirred at room temperature for 2 h before adding 5 ml of water. The mixture was extracted with EtOAc, and the organic phase washed successively with water and brine. The organic phase was dried over MgSO4, and concentrated in vacuo. The crude product was chromatographed on silica gel with 10% EtOAc in hexanes.

Example 51

Preparation of 4-Phenylpiperazine-1-(2,2,2-trifluoro-1-methyl-1-trifluoromethylethyl)-carboxamide To 1-phenylpiperazine (0.04 ml, 0.25 mmol) was added 1,1,1,3,3,3-hexafluoro-2-isocyanato-2-methylpropane (13a) (124 mg, 0.6 mmol) in 1 ml of diethylether. The mixture was stirred at room temperature in a tightly capped vial for 12 h. The reaction mixture was subjected to reverse phase HPLC ($CH_3CN/H_2O$) and the isolated product lyophilized to provide the product as a white solid.

Examples 52-98

The compounds of Examples 52-98 were prepared following the above mentioned general procedure for Example 51 using compound 13(a) and reacting it with the following amines or anilines: morpholine, 2-acetylaniline, piperidine, 3,4,5-trimethoxyaniline, 4-trifluoromethylaniline, 4-methylpiperazine, 1-aminonaphthalene, 2-chloroaniline, 4-phenylpiperidine, 2-phenylaniline, 2,6-difluoroaniline, 2-amimobenzamide, 2-chloro-6-fluoroaniline, 3-trifluoromethylaniline, 2-aminobenzenesulfonamide, 5-amino(2,2,3,3-Tetrafluoro-2,3-dihydrobenzo[1,4]dioxane), 3-trifluoromethoxyaniline, 4-trifluoromethoxyaniline, 4-methylpiperidine, 2-aminonaphthalene, 2-fluoroaniline, 2,6-dimethoxyaniline, 4-amino-3-trifluoromethoxybenzoic acid, aniline, 3-cyanoaniline, 3-methoxyaniline, 2-(1,1,2,2-tetrafluoroethoxy)aniline, 3-aminobenzenesulfonamide, 3-fluoroaniline, 4-bromoaniline, 2-cyanoaniline, 4-cyanoaniline, 3-amino-2,2-difluorobenzo[1,3]dioxane, 4-chloroaniline, 3-methylaniline, 4-aminobenzenesulfonamide, 2,6-dibromoaniline, 2-methylaniline, 4-methylaniline, pyrrolidine, 4-fluoroaniline, 2,4-dibromoaniline, azepane, 4-bromo-2-trifluoromethoxyaniline, 2-trifluoromethoxyaniline, 2-trifluoromethylaniline, and 2-methoxyaniline.

| Example Number | Structure | Name |
|---|---|---|
| 1 | 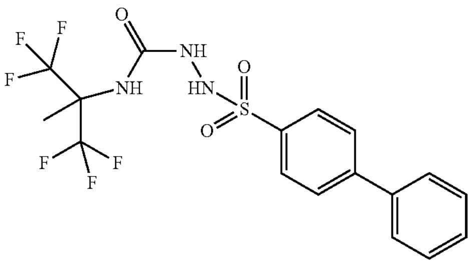 [SMILES: CC(NC(=O)NNS(=O)(=O)c1ccc(-c2ccccc2)cc1)(C(F)(F)F)C(F)(F)F] | N-2-(1,1,1,3,3,3-Hexafluoro-2-methylpropyl)-2-[(4-(phenyl)-phenylsulfonyl]hydrazine-1-carboxamide |

-continued

| Example Number | Structure | Name |
|---|---|---|
| 2 | 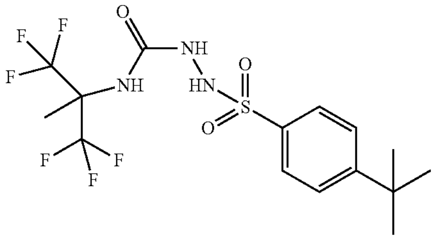 [SMILES: CC(C)(C)c1ccc(S(=O)(=O)NNC(=O)NC(C)(C(F)(F)F)C(F)(F)F)cc1] | N-2-(1,1,1,3,3,3-Hexafluoro-2-methylpropyl)-2-[(4-(2-methyl-2-propyl)-phenylsulfonyl]hydrazine-1-carboxamide |
| 3 | 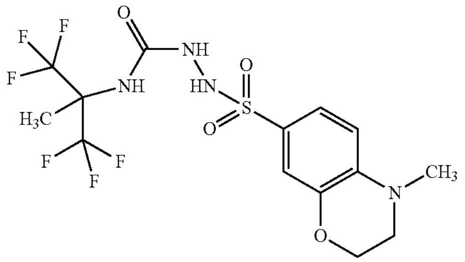 [SMILES: CN1CCOc2cc(S(=O)(=O)NNC(=O)NC(C)(C(F)(F)F)C(F)(F)F)ccc21] | N-2-(1,1,1,3,3,3-Hexafluoro-2-methylpropyl)-2-[7-(4-methyl-3,4-dihydro-2H-benzo[1,4]oxazinyl)sulfonyl] hydrazine-1-carboxamide |
| 4 | 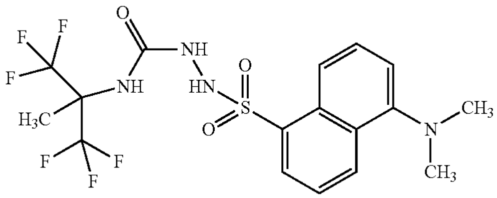 [SMILES: CN(C)c1cccc2c(S(=O)(=O)NNC(=O)NC(C)(C(F)(F)F)C(F)(F)F)cccc12] | N-2-(1,1,1,3,3,3-Hexafluoro-2-methylpropyl)-2-[5-(1-dimethylamino-naphthy)sulfonyl]hydrazine-1-carboxamide |
| 5 | 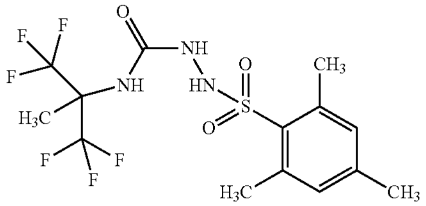 [SMILES: Cc1cc(C)c(S(=O)(=O)NNC(=O)NC(C)(C(F)(F)F)C(F)(F)F)c(C)c1] | N-2-(1,1,1,3,3,3-Hexafluoro-2-methylpropyl)-2-[(2,4,6-trimethylphenyl)sulfonyl]hydrazine-1-carboxamide |
| 6 | 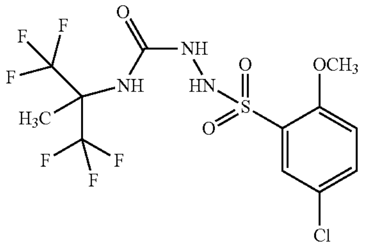 [SMILES: COc1ccc(Cl)cc1S(=O)(=O)NNC(=O)NC(C)(C(F)(F)F)C(F)(F)F] | N-2-(1,1,1,3,3,3-Hexafluoro-2-methylpropyl)-2-[(3-chloro-6-methoxyphenyl)sulfonyl]hydrazine-1-carboxamide |
| 7 | 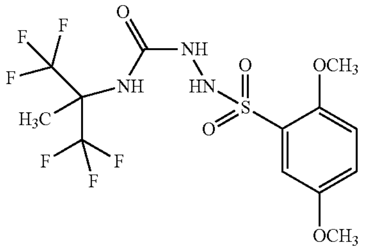 [SMILES: COc1ccc(OC)c(S(=O)(=O)NNC(=O)NC(C)(C(F)(F)F)C(F)(F)F)c1] | N-2-(1,1,1,3,3,3-Hexafluoro-2-methylpropyl)-2-[(3,6-dimethoxyphenyl)sulfonyl] hydrazine-1-carboxamide |

-continued

| Example Number | Structure | Name |
|---|---|---|
| 8 | 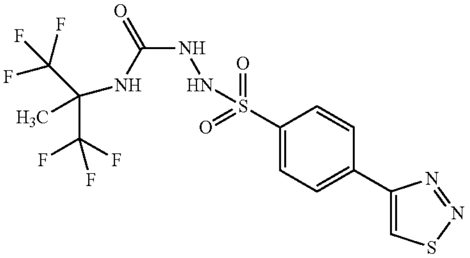 [SMILES: CC(NC(=O)NNS(=O)(=O)c1ccc(-c2csnn2)cc1)(C(F)(F)F)C(F)(F)F] | N-2-(1,1,1,3,3,3-Hexafluoro-2-methylpropyl)-2-[(4-(4-[1,2,3]thiadiazolyl)phenyl)sulfonyl] hydrazine-1-carboxamide |
| 9 | 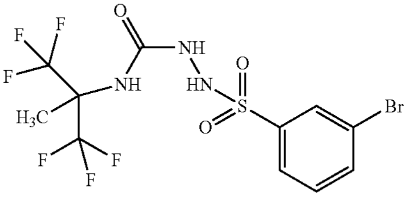 [SMILES: CC(NC(=O)NNS(=O)(=O)c1cccc(Br)c1)(C(F)(F)F)C(F)(F)F] | N-2-(1,1,1,3,3,3-Hexafluoro-2-methylpropyl)-2-[(3-bromophenyl)sulfonyl]hydrazine-1-carboxamide |
| 10 | 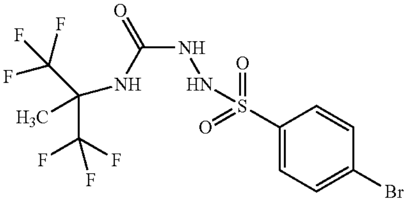 [SMILES: CC(NC(=O)NNS(=O)(=O)c1ccc(Br)cc1)(C(F)(F)F)C(F)(F)F] | N-2-(1,1,1,3,3,3-Hexafluoro-2-methylpropyl)-2-[(4-bromophenyl)sulfonyl]hydrazine-1-carboxamide |
| 11 | 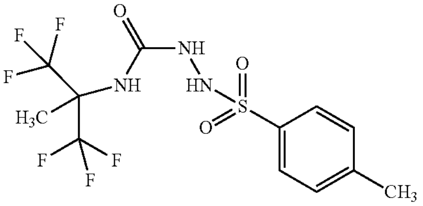 | N-2-(1,1,1,3,3,3-Hexafluoro-2-methylpropyl)-2-[(4-methylphenyl)sulfonyl]hydrazine-1-carboxamide |
| 12 | 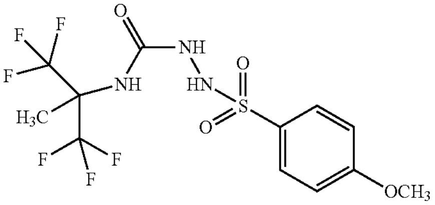 [SMILES: COc1ccc(S(=O)(=O)NNC(=O)NC(C)(C(F)(F)F)C(F)(F)F)cc1] | N-2-(1,1,1,3,3,3-Hexafluoro-2-methylpropyl)-2-[(4-methoxyphenyl)sulfonyl]hydrazine-1-carboxamide |
| 13 | 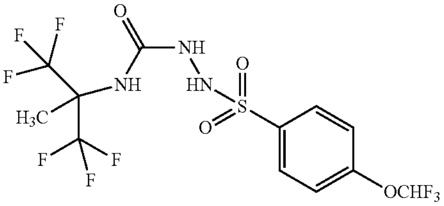 | N-2-(1,1,1,3,3,3-Hexafluoro-2-methylpropyl)-2-[(4-difluoromethoxyphenyl)sulfonyl] hydrazine-1-carboxamide |
| 14 | 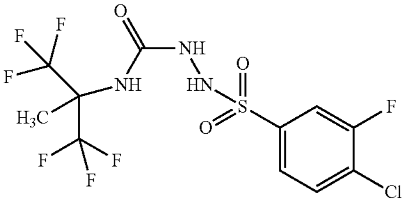 [SMILES: CC(NC(=O)NNS(=O)(=O)c1ccc(Cl)c(F)c1)(C(F)(F)F)C(F)(F)F] | N-2-(1,1,1,3,3,3-Hexafluoro-2-methylpropyl)-2-[(3-fluoro-4-chloro-phenyll)sulfonyl]hydrazine-1-carboxamide |

-continued

| Example Number | Structure | Name |
|---|---|---|
| 15 | 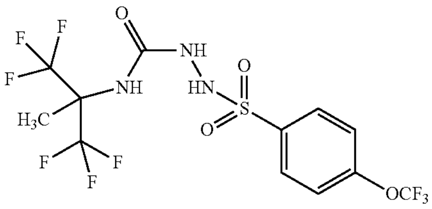 | N-2-(1,1,1,3,3,3-Hexafluoro-2-methylpropyl)-2-[(4-trifluoromethoxyphenyl)sulfonyl] hydrazine-1-carboxamide |
| 16 | 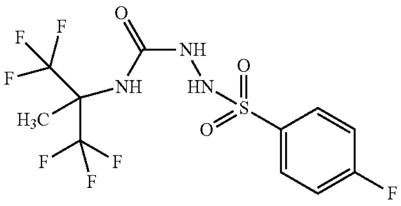 [SMILES: CC(NC(=O)NNS(=O)(=O)c1ccc(F)cc1)(C(F)(F)F)C(F)(F)F] | N-2-(1,1,1,3,3,3-Hexafluoro-2-methylpropyl)-2-[(4-fluoro-phenyl)sulfonyl]hydrazine-1-carboxamide |
| 17 | 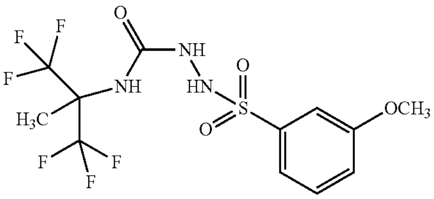 [SMILES: COc1cccc(S(=O)(=O)NNC(=O)NC(C)(C(F)(F)F)C(F)(F)F)c1] | N-2-(1,1,1,3,3,3-Hexafluoro-2-methylpropyl)-2-[(3-methoxyphenyl)sulfonyl]hydrazine-1-carboxamide |
| 18 | 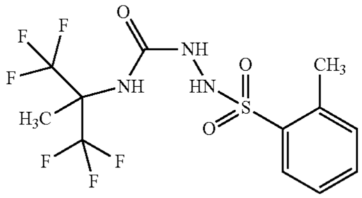 | N-2-(1,1,1,3,3,3-Hexafluoro-2-methylpropyl)-2-[(2-methylphenyl)sulfonyl]hydrazine-1-carboxamide |
| 19 | 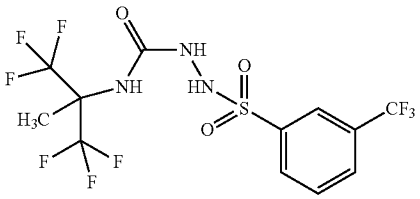 [SMILES: CC(NC(=O)NNS(=O)(=O)c1cccc(C(F)(F)F)c1)(C(F)(F)F)C(F)(F)F] | N-2-(1,1,1,3,3,3-Hexafluoro-2-methylpropyl)-2-[(3-trifluoromethylphenyl)sulfonyl] hydrazine-1-carboxamide |
| 20 | 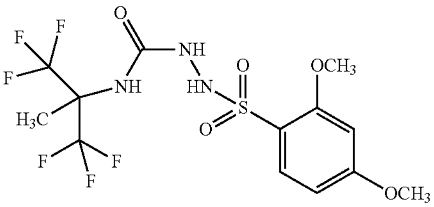 [SMILES: COc1ccc(S(=O)(=O)NNC(=O)NC(C)(C(F)(F)F)C(F)(F)F)c(OC)c1] | N-2-(1,1,1,3,3,3-Hexafluoro-2-methylpropyl)-2-[(2,4-dimethoxyphenyl)sulfonyl] hydrazine-1-carboxamide |
| 21 | 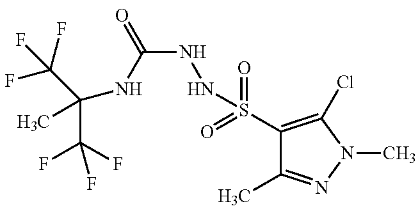 [SMILES: Cc1nn(C)c(Cl)c1S(=O)(=O)NNC(=O)NC(C)(C(F)(F)F)C(F)(F)F] | N-2-(1,1,1,3,3,3-Hexafluoro-2-methylpropyl)-2-[2-(5-chloro-1,3-dimethyl-1H-pyrazolyl)sulfonyl]hydrazine-1-carboxamide |

-continued

| Example Number | Structure | Name |
|---|---|---|
| 22 | 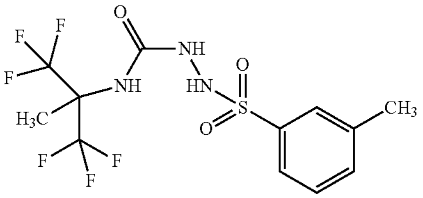 [SMILES: Cc1cccc(S(=O)(=O)NNC(=O)NC(C)(C(F)(F)F)C(F)(F)F)c1] | N-2-(1,1,1,3,3,3-Hexafluoro-2-methylpropyl)-2-[(3-methylphenyl)sulfonyl]hydrazine-1-carboxamide |
| 23 | 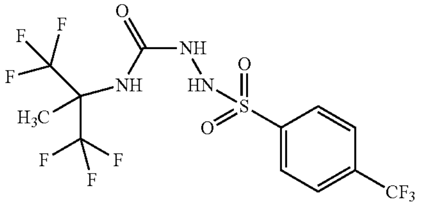 | N-2-(1,1,1,3,3,3-Hexafluoro-2-methylpropyl)-2-[(4-trifluoromethylphenyl)sulfonyl] hydrazine-1-carboxamide |
| 24 | 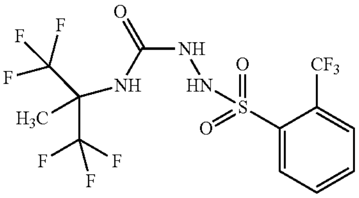 [SMILES: CC(NC(=O)NNS(=O)(=O)c1ccccc1C(F)(F)F)(C(F)(F)F)C(F)(F)F] | N-2-(1,1,1,3,3,3-Hexafluoro-2-methylpropyl)-2-[(2-trifluoromethylphenyl)sulfonyl] hydrazine-1-carboxamide |
| 25 | 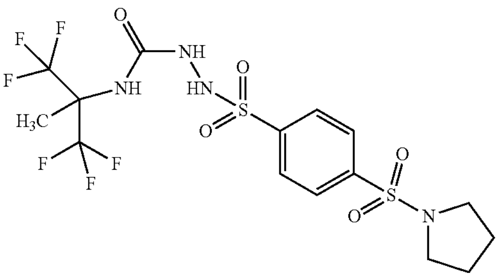 [SMILES: CC(NC(=O)NNS(=O)(=O)c1ccc(S(=O)(=O)N2CCCC2)cc1)(C(F)(F)F)C(F)(F)F] | N-2-(1,1,1,3,3,3-Hexafluoro-2-methylpropyl)-2-[4-(pyrrolidin-1-sulfonyl)phenylsulfonyl]hydrazine-1-carboxamide |
| 26 | 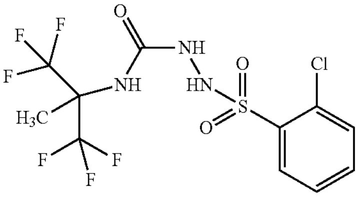 | N-2-(1,1,1,3,3,3-Hexafluoro-2-methylpropyl)-2-[(2-chlorophenyl)sulfonyl]hydrazine-1-carboxamide |
| 27 | 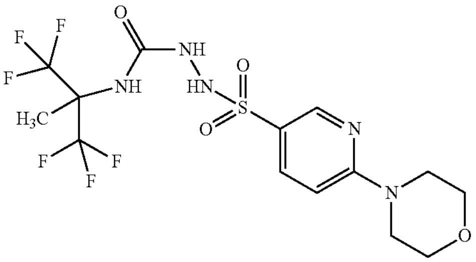 [SMILES: CC(NC(=O)NNS(=O)(=O)c1ccc(N2CCOCC2)nc1)(C(F)(F)F)C(F)(F)F] | N-2-(1,1,1,3,3,3-Hexafluoro-2-methylpropyl)-2-[2-(5-morpholin-4-yl)pyridylsulfonyl]hydrazine-1-carboxamide |

-continued

| Example Number | Structure | Name |
|---|---|---|
| 28 | 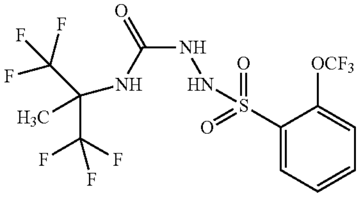 | N-2-(1,1,1,3,3,3-Hexafluoro-2-methylpropyl)-2-[(2-trifluoromethoxyphenyl)sulfonyl] hydrazine-1-carboxamide |
| 29 | 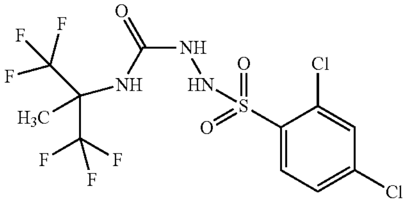 [SMILES: CC(NC(=O)NNS(=O)(=O)c1ccc(Cl)cc1Cl)(C(F)(F)F)C(F)(F)F] | N-2-(1,1,1,3,3,3-Hexafluoro-2-methylpropyl)-2-[(2,4-dichlorophenyl)sulfonyl]hydrazine-1-carboxamide |
| 30 | 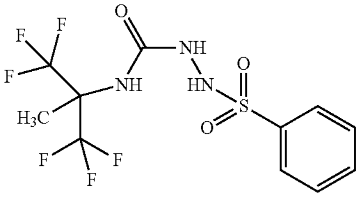 [SMILES: CC(NC(=O)NNS(=O)(=O)c1ccccc1)(C(F)(F)F)C(F)(F)F] | N-2-(1,1,1,3,3,3-Hexafluoro-2-methylpropyl)-2-[phenylsulfonyl]hydrazine-1-carboxamide |
| 31 | 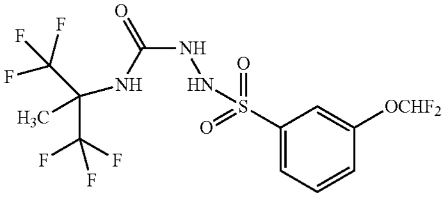 [SMILES: CC(NC(=O)NNS(=O)(=O)c1cccc(OC(F)F)c1)(C(F)(F)F)C(F)(F)F] | N-2-(1,1,1,3,3,3-Hexafluoro-2-methylpropyl)-2-[(3-difluoromethoxyphenyl)sulfonyl] hydrazine-1-carboxamide |
| 32 | 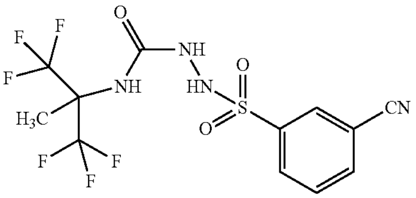 [SMILES: CC(NC(=O)NNS(=O)(=O)c1cccc(C#N)c1)(C(F)(F)F)C(F)(F)F] | N-2-(1,1,1,3,3,3-Hexafluoro-2-methylpropyl)-2-[(3-cyanophenyl)sulfonyl]hydrazine-1-carboxamide |
| 33 | 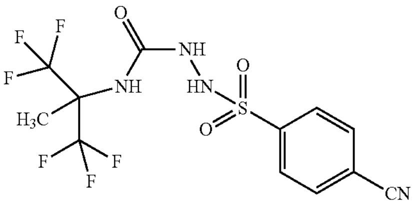 [SMILES: CC(NC(=O)NNS(=O)(=O)c1ccc(C#N)cc1)(C(F)(F)F)C(F)(F)F] | N-2-(1,1,1,3,3,3-Hexafluoro-2-methylpropyl)-2-[(4-cyanophenyl)sulfonyl]hydrazine-1-carboxamide |
| 34 | 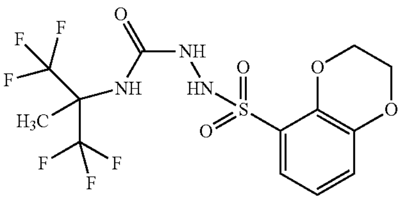 [SMILES: CC(NC(=O)NNS(=O)(=O)c1cccc2c1OCCO2)(C(F)(F)F)C(F)(F)F] | N-2-(1,1,1,3,3,3-Hexafluoro-2-methylpropyl)-2-[5-(2,3-dihydrobenzo[1,4]dioxinyl)sulfonyl] hydrazine-1-carboxamide |

-continued

| Example Number | Structure | Name |
|---|---|---|
| 35 | 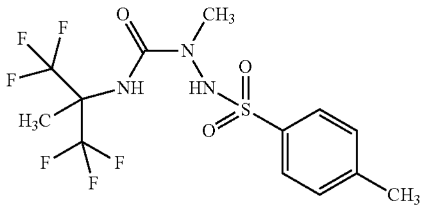 [SMILES: Cc1ccc(S(=O)(=O)NN(C)C(=O)NC(C)(C(F)(F)F)C(F)(F)F)cc1] | N-2-(1,1,1,3,3,3-Hexafluoro-2-methylpropyl)-2-[(4-methylphenyl)sulfonyl]-1-methylhydrazine-1-carboxamide |
| 36 | 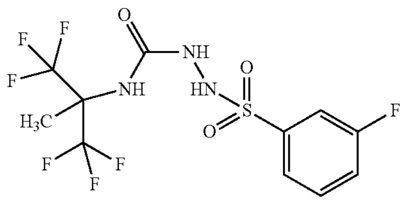 [SMILES: CC(NC(=O)NNS(=O)(=O)c1cccc(F)c1)(C(F)(F)F)C(F)(F)F] | N-2-(1,1,1,3,3,3-Hexafluoro-2-methylpropyl)-2-[(3-fluorophenyl)sulfonyl]hydrazine-1-carboxamide |
| 37 | 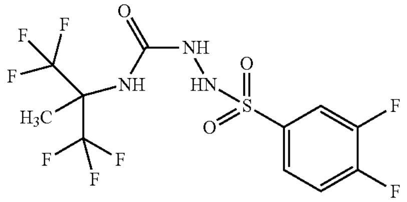 [SMILES: CC(NC(=O)NNS(=O)(=O)c1ccc(F)c(F)c1)(C(F)(F)F)C(F)(F)F] | N-2-(1,1,1,3,3,3-Hexafluoro-2-methylpropyl)-2-[(3,4-difluorophenyl)sulfonyl]hydrazine-1-carboxamide |
| 38 | 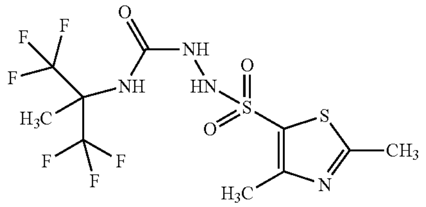 [SMILES: Cc1nc(C)c(S(=O)(=O)NNC(=O)NC(C)(C(F)(F)F)C(F)(F)F)s1] | N-2-(1,1,1,3,3,3-Hexafluoro-2-methylpropyl)-2-[(2,4-dimethylthiazol-5-yl)sulfonyl]hydrazine-1-carboxamide |
| 39 | 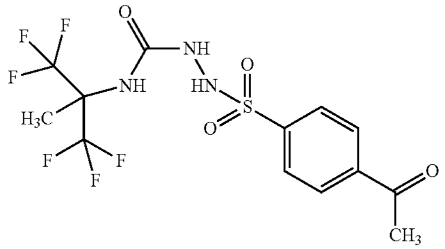 [SMILES: CC(=O)c1ccc(S(=O)(=O)NNC(=O)NC(C)(C(F)(F)F)C(F)(F)F)cc1] | N-2-(1,1,1,3,3,3-Hexafluoro-2-methylpropyl)-2-[(4-acetylphenyl)sulfonyl]hydrazine-1-carboxamide |
| 40 | 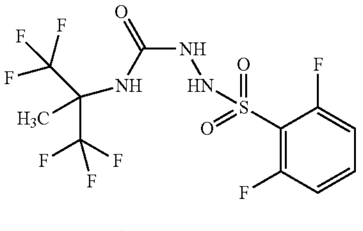 | N-2-(1,1,1,3,3,3-Hexafluoro-2-methylpropyl)-2-[(2,6-difluorophenyl)sulfonyl]hydrazine-1-carboxamide |
| 41 | 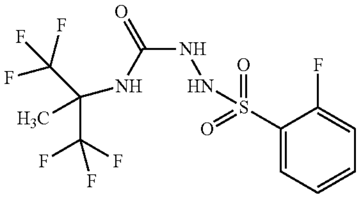 [SMILES: CC(NC(=O)NNS(=O)(=O)c1ccccc1F)(C(F)(F)F)C(F)(F)F] | N-2-(1,1,1,3,3,3-Hexafluoro-2-methylpropyl)-2-[(2-fluorophenyl)sulfonyl]hydrazine-1-carboxamide |

-continued

| Example Number | Structure | Name |
|---|---|---|
| 42 | 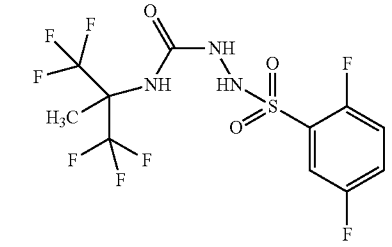 [SMILES: CC(NC(=O)NNS(=O)(=O)c1cc(F)ccc1F)(C(F)(F)F)C(F)(F)F] | N-2-(1,1,1,3,3,3-Hexafluoro-2-methylpropyl)-2-[(2,5-difluorophenyl)sulfonyl]hydrazine-1-carboxamide |
| 43 | 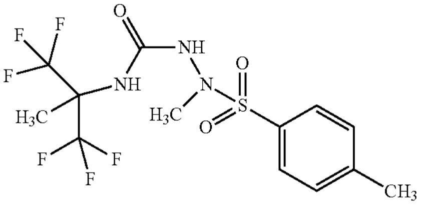 [SMILES: Cc1ccc(S(=O)(=O)N(C)NC(=O)NC(C)(C(F)(F)F)C(F)(F)F)cc1] | N-2-(1,1,1,3,3,3-Hexafluoro-2-methylpropyl)-2-[(4-methylphenyl)sulfonyl]-2-methylhydrazine-1-carboxamide |
| 44 | 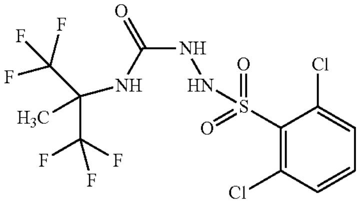 [SMILES: CC(NC(=O)NNS(=O)(=O)c1c(Cl)cccc1Cl)(C(F)(F)F)C(F)(F)F] | N-2-(l,1,1,3,3,3-Hexafluoro-2-methylpropyl)-2-[(2,6-dichlorophenyl)sulfonyl]hydrazine-1-carboxomide |
| 45 | 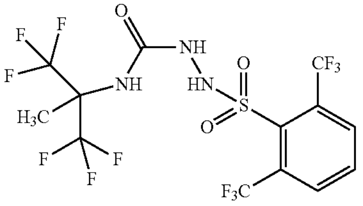 [SMILES: CC(NC(=O)NNS(=O)(=O)c1c(C(F)(F)F)cccc1C(F)(F)F)(C(F)(F)F)C(F)(F)F] | N-2-(1,1,1,3,3,3-Hexafluoro-2-methylpropyl)-2-[(2,6-ditrifluoromethylphenyl)sulfonyl] hydrazine-1-carboxamide |
| 46 | 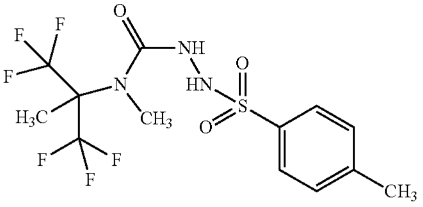 [SMILES: Cc1ccc(S(=O)(=O)NNC(=O)N(C)C(C)(C(F)(F)F)C(F)(F)F)cc1] | N-2-(1,1,1,3,3,3-Hexafluoro-2-methylpropyl)-2-[(4-methylphenyl)sulfonyl]hydrazine-1-methylcarboxamide |
| 47 | 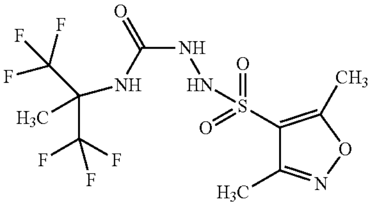 [SMILES: Cc1noc(C)c1S(=O)(=O)NNC(=O)NC(C)(C(F)(F)F)C(F)(F)F] | N-2-(1,1,1,3,3,3-Hexafluoro-2-methylpropyl)-2-[(3,5-dimethylisoxazol-5-yl)sulfonyl]hydrazine-1-carboxamide |
| 48 | 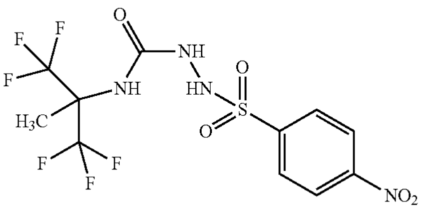 [SMILES: CC(NC(=O)NNS(=O)(=O)c1ccc([N+](=O)[O-])cc1)(C(F)(F)F)C(F)(F)F] | N-2-(1,1,1,3,3,3-Hexafluoro-2-methylpropyl)-2-[(4-nitrophenyl)sulfonyl]hydrazine-1-carboxamide |

-continued

| Example Number | Structure | Name |
|---|---|---|
| 49 | 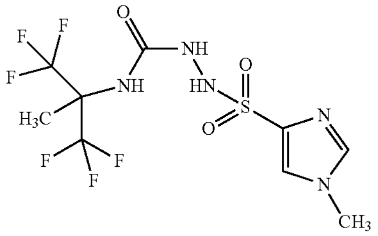 [SMILES: Cn1cnc(S(=O)(=O)NNC(=O)NC(C)(C(F)(F)F)C(F)(F)F)c1] | N-2-(1,1,1,3,3,3-Hexafluoro-2-methylpropyl)-2-[(1-methylimidazol-4-yl)sulfonyl]hydrazine-1-carboxamide |
| 50 | 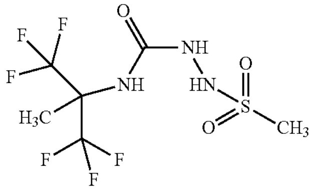 [SMILES: CC(NC(=O)NNS(C)(=O)=O)(C(F)(F)F)C(F)(F)F] | N-2-(1,1,1,3,3,3-Hexafluoro-2-methylpropyl)-2-[methylsulfonyl]hydrazine-1-carboxamide |
| 51 | 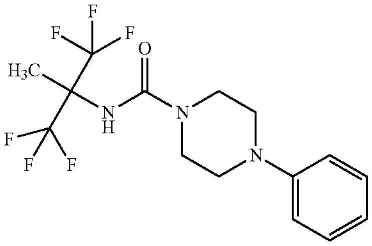 [SMILES: CC(NC(=O)N1CCN(c2ccccc2)CC1)(C(F)(F)F)C(F)(F)F] | 4-Phenylpiperazine-1-(2,2,2-trifluoro-1-methyl-1-trifluoromethylethyl)-carboxamide |
| 52 | 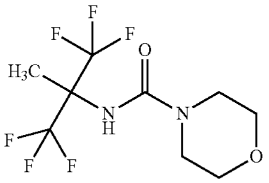 [SMILES: CC(NC(=O)N1CCOCC1)(C(F)(F)F)C(F)(F)F] | 4-Morpholino-1-(2,2,2-trifluoro-1-methyl-1-trifluoromethylethyl)-carboxamide |
| 53 | 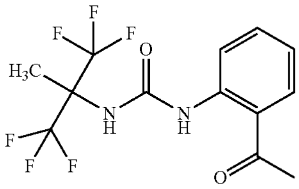 [SMILES: CC(=O)c1ccccc1NC(=O)NC(C)(C(F)(F)F)C(F)(F)F] | 1-(2-Acetylphenyl)-3-(2,2,2-trifluoro-1-methyl-1-trifluoromethylethyl)-urea |
| 54 | 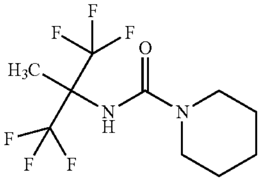 [SMILES: CC(NC(=O)N1CCCCC1)(C(F)(F)F)C(F)(F)F] | 1-Piperidino-1-(2,2,2-trifluoro-1-methyl-1-trifluoromethylethyl)-carboxamide |
| 55 | 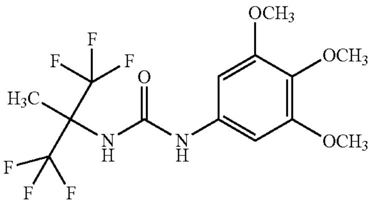 [SMILES: COc1cc(NC(=O)NC(C)(C(F)(F)F)C(F)(F)F)cc(OC)c1OC] | 1-(2,2,2-trifluoro-1-methyl-1-trifluoromethylethyl)-3-(3,4,5-trimethoxyphenyl)-urea |

-continued

| Example Number | Structure | Name |
|---|---|---|
| 56 | 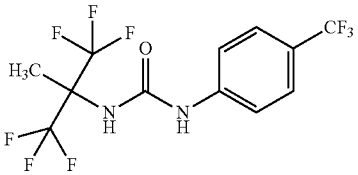 [SMILES: CC(NC(=O)Nc1ccc(C(F)(F)F)cc1)(C(F)(F)F)C(F)(F)F] | 1-(4-Trifluoromethylphenyl)-3-(2,2,2-trifluoro-1-methyl-1-trifluoromethylethyl)-urea |
| 57 | 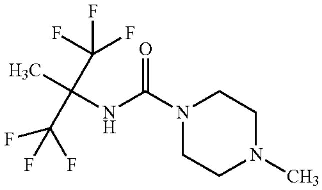 | 4-Methylpiperazine-1-(2,2,2-trifluoro-1-methyl-1-trifluoromethylethyl)-carboxamide |
| 58 | 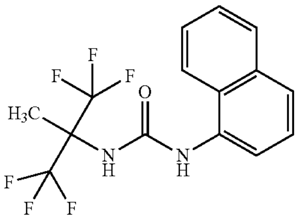 [SMILES: CC(NC(=O)Nc1cccc2ccccc12)(C(F)(F)F)C(F)(F)F] | 1-Naphthalen-1-yl-3-(2,2,2-trifluoro-1-methyl-1-trifluoromethylethyl)-urea |
| 59 | 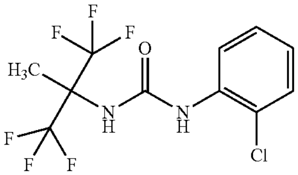 [SMILES: CC(NC(=O)Nc1ccccc1Cl)(C(F)(F)F)C(F)(F)F] | 1-(4-Chlorophenyl)-3-(2,2,2-trifluoro-1-methyl-1-trifluoromethylethyl)-urea |
| 60 | 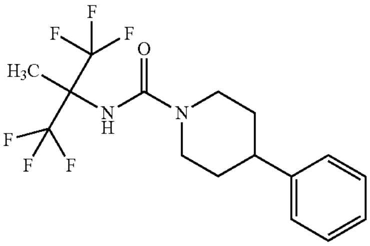 [SMILES: CC(NC(=O)N1CCC(c2ccccc2)CC1)(C(F)(F)F)C(F)(F)F] | 4-Phenylpiperidin-1-yl-1-(2,2,2-trifluoro-1-methyl-1-trifluoromethylethyl)-carboxamide |
| 61 | 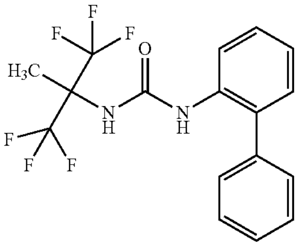 [SMILES: CC(NC(=O)Nc1ccccc1-c1ccccc1)(C(F)(F)F)C(F)(F)F] | 1-(2-Phenyl(phenyl))-3-(2,2,2-trifluoro-1-methyl-1-trifluoromethylethyl)-urea |
| 62 | 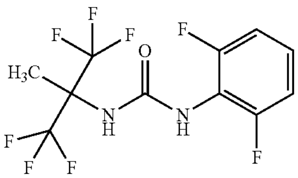 [SMILES: CC(NC(=O)Nc1c(F)cccc1F)(C(F)(F)F)C(F)(F)F] | 1-(2,6-Difluorophenyl)-3-(2,2,2-trifluoro-1-methyl-1-trifluoromethylethyl)-urea |

-continued

| Example Number | Structure | Name |
|---|---|---|
| 63 | 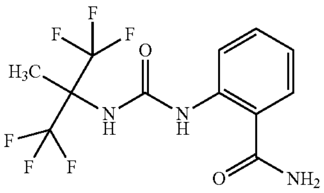 [SMILES: CC(NC(=O)Nc1ccccc1C(N)=O)(C(F)(F)F)C(F)(F)F] | 2-[3-(1,1-Bis-trifluoromethylethyl)-ureido]benzamide |
| 64 | 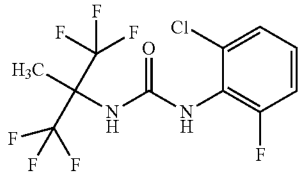 [SMILES: CC(NC(=O)Nc1c(F)cccc1Cl)(C(F)(F)F)C(F)(F)F] | 1-(2-Chloro-6-fluorophenyl)-3-(2,2,2-trifluoro-1-methyl-1-trifluoromethylethyl)-urea |
| 65 | 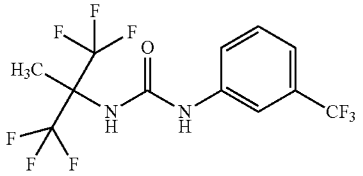 [SMILES: CC(NC(=O)Nc1cccc(C(F)(F)F)c1)(C(F)(F)F)C(F)(F)F] | 1-(3-Trifluoromethylphenyl)-3-(2,2,2-trifluoro-1-methyl-1-trifluoromethylethyl)-urea |
| 66 | 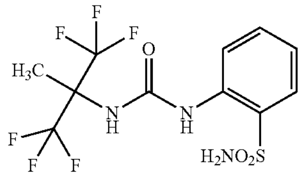 [SMILES: CC(NC(=O)Nc1ccccc1S(N)(=O)=O)(C(F)(F)F)C(F)(F)F] | 2-[3-(1,1-Bis-trifluoromethylethyl)-ureido]benzenesulfonamide |
| 67 | 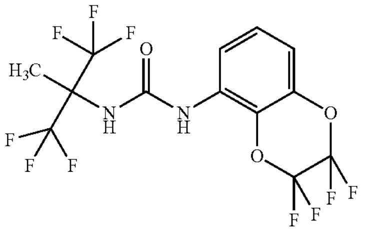 [SMILES: CC(NC(=O)Nc1cccc2c1OC(F)(F)C(F)(F)O2)(C(F)(F)F)C(F)(F)F] | 1-(2,2,3,3-Tetrafluoro-2,3-dihydrobenzo[1,4]dioxin-5-yl)-3-(2,2,2-trifluoro-1-methyl-1-trifluoromethylethyl)-urea |
| 68 | 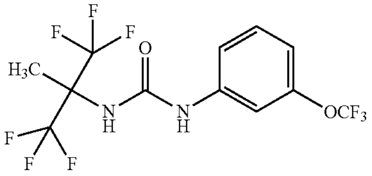 [SMILES: CC(NC(=O)Nc1cccc(OC(F)(F)F)c1)(C(F)(F)F)C(F)(F)F] | 1-(3-Trifluoromethoxyphenyl)-3-(2,2,2-trifluoro-1-methyl-1-trifluoromethylethyl)-urea |
| 69 | 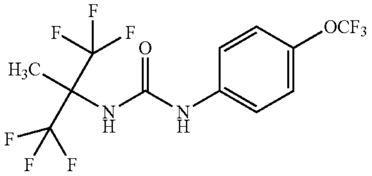 [SMILES: CC(NC(=O)Nc1ccc(OC(F)(F)F)cc1)(C(F)(F)F)C(F)(F)F] | 1-(4-Trifluoromethoxyphenyl)-3-(2,2,2-trifluoro-1-methyl-1-trifluoromethylethyl)-urea |
| 70 | 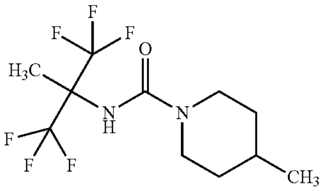 [SMILES: CC1CCN(C(=O)NC(C)(C(F)(F)F)C(F)(F)F)CC1] | 4-Methyl-1-piperidine-1-(2,2,2-trifluoro-1-methyl-1-trifluoromethylethyl)-carboxamide |

-continued

| Example Number | Structure | Name |
|---|---|---|
| 71 | 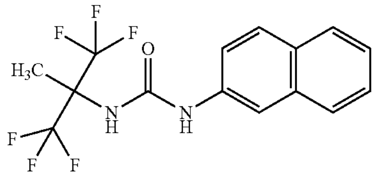 [SMILES: CC(NC(=O)Nc1ccc2ccccc2c1)(C(F)(F)F)C(F)(F)F] | 1-Naphthalen-2-yl-3-(2,2,2-trifluoro-1-methyl-1-trifluoromethylethyl)-urea |
| 72 | 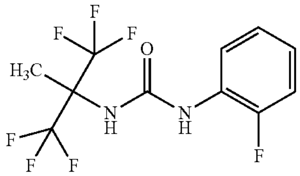 [SMILES: CC(NC(=O)Nc1ccccc1F)(C(F)(F)F)C(F)(F)F] | 1-(2-fluorophenyl)-3-(2,2,2-trifluoro-1-methyl-1-trifluoromethylthyl)-urea |
| 73 | 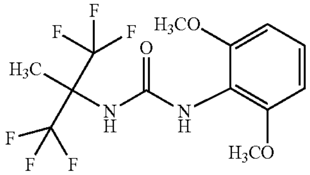 [SMILES: COc1cccc(OC)c1NC(=O)NC(C)(C(F)(F)F)C(F)(F)F] | 1-(2,6-Dimethoxyphenyl)-3-(2,2,2-trifluoro-1-methyl-1-trifluoromethylethyl)-urea |
| 74 | 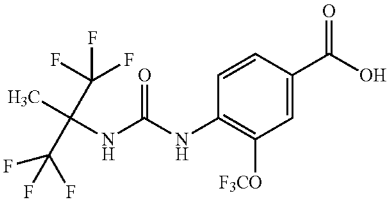 [SMILES: CC(NC(=O)Nc1ccc(C(=O)O)cc1OC(F)(F)F)(C(F)(F)F)C(F)(F)F] | 3-Trifluormethoxy-4-[3-(1,1-bis-trifluoromethylethyl)-ureido]benzoic acid |
| 75 | 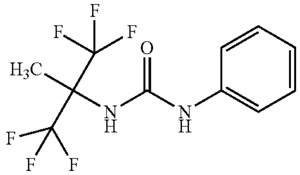 [SMILES: CC(NC(=O)Nc1ccccc1)(C(F)(F)F)C(F)(F)F] | 1-Phenyl-3-(2,2,2-trifluoro-1-methyl-1-trifluoromethylethyl)-urea |
| 76 | 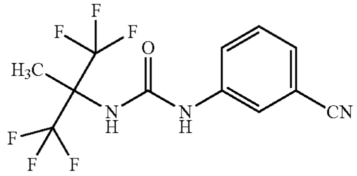 [SMILES: CC(NC(=O)Nc1cccc(C#N)c1)(C(F)(F)F)C(F)(F)F] | 1-(3-Cyanophenyl)-3-(2,2,2-trifluoro-1-methyl-1-trifluoromethylethyl)-urea |
| 77 | 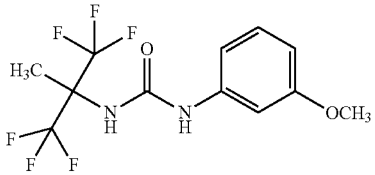 [SMILES: COc1cccc(NC(=O)NC(C)(C(F)(F)F)C(F)(F)F)c1] | 1-(3-Methoxyphenyl)-3-(2,2,2-trifluoro-1-methyl-1-trifluoromethylethyl)-urea |
| 78 | 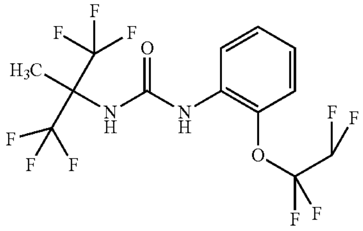 [SMILES: CC(NC(=O)Nc1ccccc1OC(F)(F)C(F)F)(C(F)(F)F)C(F)(F)F] | 1-(2-(1,1,2,2-Tetrafluoroethoxy)phenyl)-3-(2,2,2-trifluoro-1-methyl-1-trifluoromethylethyl)-urea |

-continued

| Example Number | Structure | Name |
|---|---|---|
| 79 | 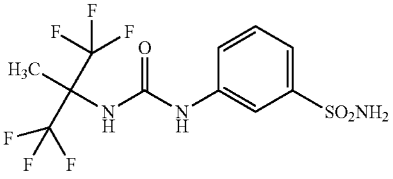 [SMILES: CC(NC(=O)Nc1cccc(S(N)(=O)=O)c1)(C(F)(F)F)C(F)(F)F] | 3-[3-(1,1-Bis-trifluoromethylethyl)-ureido]benzenesulfonamide |
| 80 | 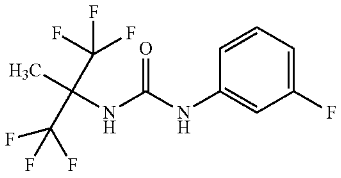 [SMILES: CC(NC(=O)Nc1cccc(F)c1)(C(F)(F)F)C(F)(F)F] | 1-(3-fluorophenyl)-3-(2,2,2-trifluoro-1-methyl-1-trifluoromethylethyl)-urea |
| 81 | 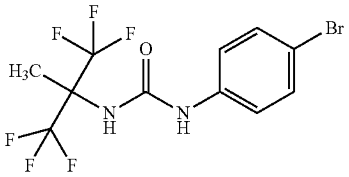 | l-(4-Bromophenyl)-3-(2,2,2-trifluoro-1-methyl-1-trifluoromethylethyl)-urea |
| 82 | 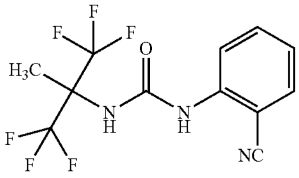 [SMILES: CC(NC(=O)Nc1ccccc1C#N)(C(F)(F)F)C(F)(F)F] | l-(2-Cyanophenyl)-3-(2,2,2-trifluoro-1-methyl-1-trifluoromethylethyl)-urea |
| 83 | 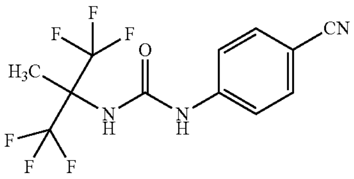 | 1-(4-Cyanophenyl)-3-(2,2,2-trifluoro-1-methyl-1-trifluoromethylethyl)-urea |
| 84 | 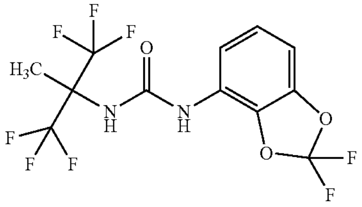 [SMILES: CC(NC(=O)Nc1cccc2c1OC(F)(F)O2)(C(F)(F)F)C(F)(F)F] | 1-(2,2-Difluorobenzo[1,3]dioxol-4-yl)-3-(2,2,2-trifluoro-1-methyl-1-trifluoromethylethyl)-urea |
| 85 | 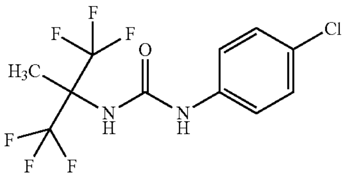 | 1-(4-Chlorophenyl)-3-(2,2,2-trifluoro-1-methyl-1-trifluoromethylethyl)-urea |
| 86 | 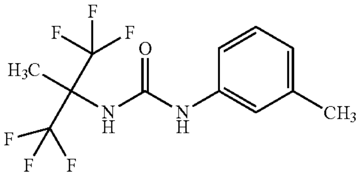 [SMILES: Cc1cccc(NC(=O)NC(C)(C(F)(F)F)C(F)(F)F)c1] | 1-(3-Methylphenyl)-3-(2,2,2-trifluoro-1-methyl-1-trifluoromethylethyl)-urea |

-continued

| Example Number | Structure | Name |
|---|---|---|
| 87 | 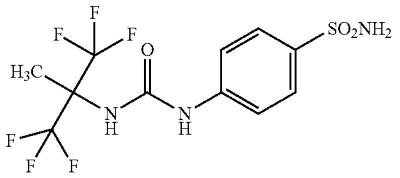 [SMILES: CC(NC(=O)Nc1ccc(S(N)(=O)=O)cc1)(C(F)(F)F)C(F)(F)F] | 4-[3-(1,1-Bis-trifluoromethylethyl)-ureido]benzenesulfonamide |
| 88 | 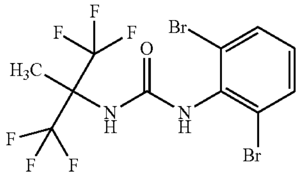 [SMILES: CC(NC(=O)Nc1c(Br)cccc1Br)(C(F)(F)F)C(F)(F)F] | 1-(2,6-Dibromophenyl)-3-(2,2,2-trifluoro-1-methyl-1-trifluoromethylethyl)-urea |
| 89 | 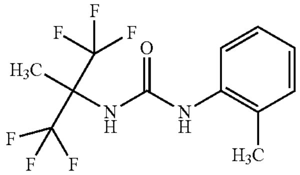 [SMILES: Cc1ccccc1NC(=O)NC(C)(C(F)(F)F)C(F)(F)F] | l-(2-Methylphenyl)-3-(2,2,2-trifluoro-1-methyl-1-trifluoromethylethyl)-urea |
| 90 | 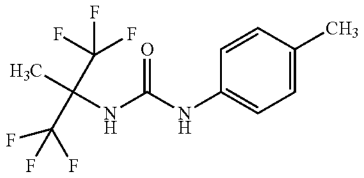 [SMILES: Cc1ccc(NC(=O)NC(C)(C(F)(F)F)C(F)(F)F)cc1] | 1-(4-Methylphenyl)-3-(2,2,2-trifluoro-1-methyl-1-trifluoromethylethyl)-urea |
| 91 | 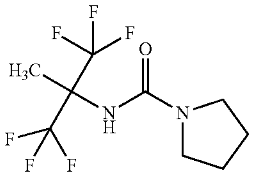 [SMILES: CC(NC(=O)N1CCCC1)(C(F)(F)F)C(F)(F)F] | 1-Pyrrolidinyl-1-(2,2,2-trifluoro-1-methyl-1-trifluoromethylethyl)-carboxamide |
| 92 | 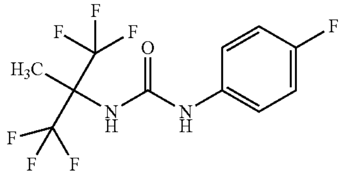 [SMILES: CC(NC(=O)Nc1ccc(F)cc1)(C(F)(F)F)C(F)(F)F] | 1-(4-Fluorophenyl)-3-(2,2,2-trifluoro-1-methyl-1-trifluoromethylethyl)-urea |
| 93 | 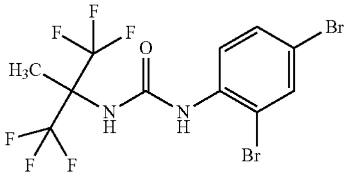 [SMILES: CC(NC(=O)Nc1ccc(Br)cc1Br)(C(F)(F)F)C(F)(F)F] | 1-(2,4-Dibromophenyl)-3-(2,2,2-trifluoro-1-methyl-1-trifluoromethylethyl)-urea |
| 94 | 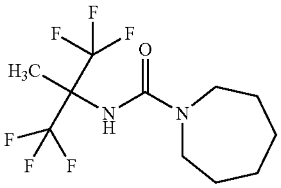 [SMILES: CC(NC(=O)N1CCCCCC1)(C(F)(F)F)C(F)(F)F] | Azepane-1-carboxylic acid (2,2,2-trifluoro-1-methyl-1-trifluoromethylethyl)-amide |

-continued

| Example Number | Structure | Name |
|---|---|---|
| 95 | 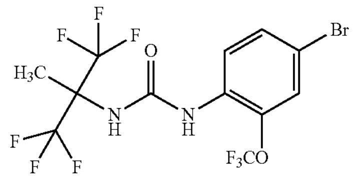 [SMILES: CC(NC(=O)Nc1ccc(Br)cc1OC(F)(F)F)(C(F)(F)F)C(F)(F)F] | 1-(4-Bromo-2-trifluoromethoxyphenyl)-3-(2,2,2-trifluoro-1-methyl-1-trifluoromethylethyl)-urea |
| 96 | 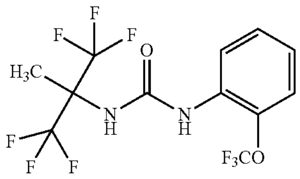 [SMILES: CC(NC(=O)Nc1ccccc1OC(F)(F)F)(C(F)(F)F)C(F)(F)F] | 1-(2-Trifluoromethoxyphenyl)-3-(2,2,2-trifluoro-1-methyl-1-trifluoromethylethyl)-urea |
| 97 | 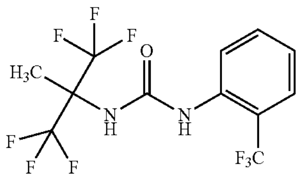 | 1-(2-Trifluoromethylphenyl)-3-(2,2,2-trifluoro-1-methyl-1-trifluoromethylethyl)-urea |
| 98 | 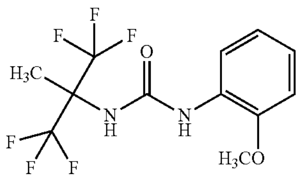 [SMILES: COc1ccccc1NC(=O)NC(C)(C(F)(F)F)C(F)(F)F] | l-(2-Methoxyphenyl)-3-(2,2,2-trifluoro-1-methyl-1-trifluoromtthylethyl)-urea |

Examples 99-112

The compounds of Examples 99-112 were prepared using the following synthetic route;

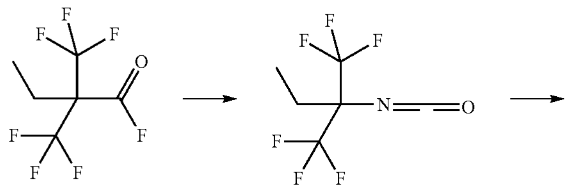

1

2

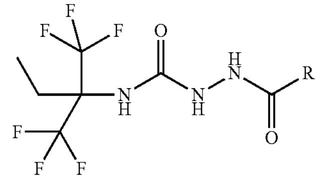

3

To synthesize isocyanate, 2, a solution of $Me_3SiN_3$ (3.12 ml, 25 mMol) in dry o-xylene (15 ml) was slowly added to a solution of the fluoride, 1 (5.34 g, 24 mMol), and triethylbenzylammonium chloride (TEBA, 22 mg, 4 mMol) in dry o-xylene (20 ml) at room temperature. The reaction mixture was heated to 110° C. and stirred for 4 hours. The desired isocyanate, 2, was isolated by distillation of the crude reaction mixture (2.49 g, 46% yield).

The general procedure, using hydrazine as starting reagent is as follows:

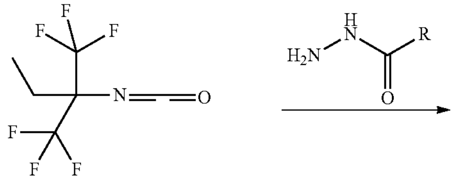

2

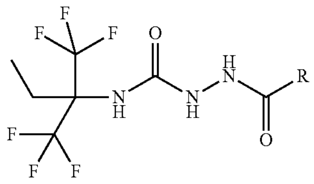

3

To a solution of hydrazide (1 eq) in dry THF was added a solution of the isocyanate (1 eq) in dry THF. The reaction mixture was stirred at room temperature overnight. The required product was isolated using HPLC eluting with 10-80% acetonitrile/$H_2O$ (with 0.1% TFA) solvent system.

The general procedure using acid chloride as starting reagent is as follows:

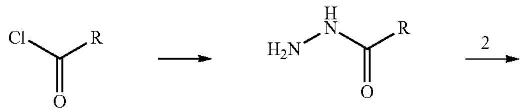

-continued

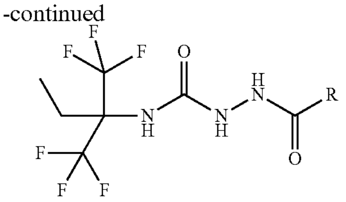

3

To a solution of anhydrous hydrazine (1 eq) in dry THF was slowly added a solution of acid chloride (1 eq) in dry THF. The reaction mixture was stirred at room temperature for 1 hour, after which a solution of the isocyanate (1 eq) in dry THF was added. The reaction mixture was stirred at room temperature overnight. The required product was isolated using HPLC eluting with 10-80% acetonitrile/$H_2O$ (with 0.1% TFA) solvent system.

| Example Number | Structure | NMR/MS Data | Name |
|---|---|---|---|
| N/A | 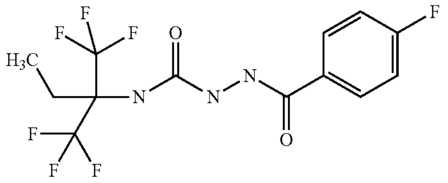 [SMILES: CCC(NC(=O)NNC(=O)c1ccc(F)cc1)(C(F)(F)F)C(F)(F)F] | | N-[1,1-bis(trifluoromethyl)propyl]-2-(4-fluorobenzoyl)hydrazinecarboxamide |
| N/A | 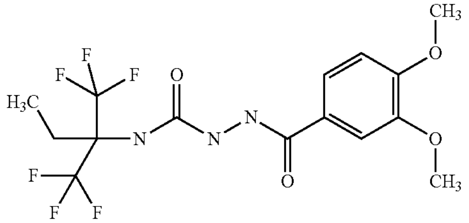 [SMILES: CCC(NC(=O)NNC(=O)c1ccc(OC)c(OC)c1)(C(F)(F)F)C(F)(F)F] | | N-[1,1-bis(trifluoromethyl)propyl]-2-(3,4-dimethoxybenzoyl)hydrazinecarboxamide |
| 99[1] | 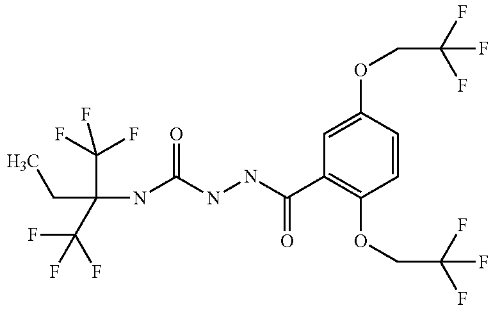 [SMILES: CCC(NC(=O)NNC(=O)c1cc(OCC(F)(F)F)ccc1OCC(F)(F)F)(C(F)(F)F)C(F)(F)F] | $^1$H NMR in DMSO-$d_6$: δ 9.92 (d, 1H), 8.36 (s, 1H), 7.26 (m, 4H), 4.80 (m, 4H), 2.43 (q, 2H), 1.03 (t, 3H) | 2-[2,5-bis(2,2,2-trifluoroethoxy)benzoyl]-N-[1,1-bis(trifluoromethyl)propyl] hydrazinecarboxamide |
| 100[1] | 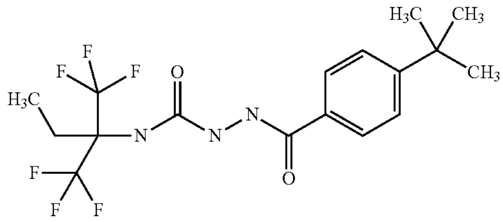 [SMILES: CCC(NC(=O)NNC(=O)c1ccc(C(C)(C)C)cc1)(C(F)(F)F)C(F)(F)F] | $^1$H NMR in $CD_3OD$: δ 7.80 (dd, 2H), 7.52 (dd, 2H), 2.50 (q, 2H), 1.34 (s, 9H), 1.11 (t, 3H) | N-[1,1-bis(2,2,2-trifluoromethyl)propyl]-2-(4-tert-butylbenzoyl)hydrazinecarboxamide |

-continued

| Example Number | Structure | NMR/MS Data | Name |
|---|---|---|---|
| 101[2] | 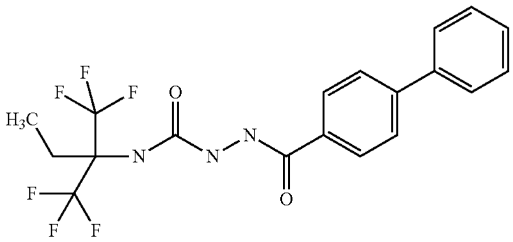 [SMILES: CCC(NC(=O)NNC(=O)c1ccc(-c2ccccc2)cc1)(C(F)(F)F)C(F)(F)F] | $^1$H NMR in $CD_3OD$: δ 7.94 (d, 2H), 7.74 (d, 2H), 7.67 (dd, 2H), 7.47 (t, 2H), 7.38 (t, 1H), 2.50 (q, 2H), 1.12 (t, 3H) | 2-(1,1'-biphenyl-4-ylcarbonyl)-N-[1,1-bis(trifluoromethyl)propyl] hydrazinecarboxamide |
| 102[1] | 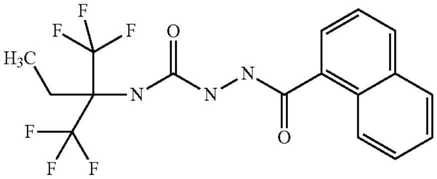 [SMILES: CCC(NC(=O)NNC(=O)c1cccc2ccccc12)(C(F)(F)F)C(F)(F)F] | $^1$H NMR in $CD_3OD$: δ 8.34 (d, 1H), 8.01 (d, 1H), 7.93 (d, 1H), 7.76 (dd, 1H), 7.56 (m, 3H), 2.55 (q, 2H), 1.15 (t, 3H) | N-[1,1-bis(trifluoromethyl)propyl]-2-(1-naphthoyl)hydrazinecarboxamide |
| 103[3] | 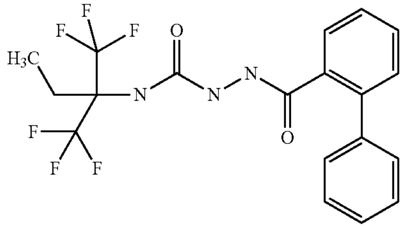 [SMILES: CCC(NC(=O)NNC(=O)c1ccccc1-c1ccccc1)(C(F)(F)F)C(F)(F)F] | $^1$H NMR in $CD_3OD$: δ 7.65 (d, 1H), 7.54 (t, 1H), 7.39 (m, 7H), 2.49 (q, 2H), 1.07 (t, 3H) | 2-(1,1'-biphenyl-2-ylcarbonyl)-N-[1,1-bis(trifluoromethyl)propyl] hydrazinecarboxamide |
| 104[1] | 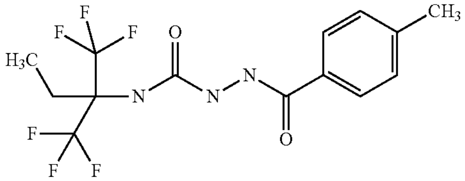 [SMILES: CCC(NC(=O)NNC(=O)c1ccc(C)cc1)(C(F)(F)F)C(F)(F)F] | $^1$H NMR in $CD_3OD$: δ 7.76 (d, 2H), 7.29 (d, 2H), 2.49 (q, 2H), 2.40 (s, 3H), 1.10 (t, 3H) | N-[1,1-bis(trifluoromethyl)propyl]-2-(4-methylbenzoyl)hydrazinecarboxamide |
| 105[3] | 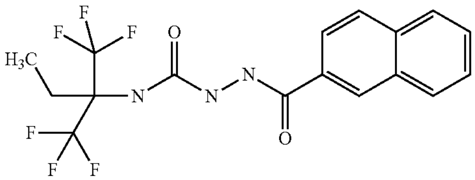 [SMILES: CCC(NC(=O)NNC(=O)c1ccc2ccccc2c1)(C(F)(F)F)C(F)(F)F] | $^1$H NMR in $CD_3OD$: δ 8.44 (s, 1H), 7.93 (m, 4H), 7.59 (m, 2H), 2.51 (q, 2H), 1.13 (t, 3H) | N-[1,1-bis(trifluoromethyl)propyl]-2-(2-naphthoyl)hydrazinecarboxamide |
| 106[4] | 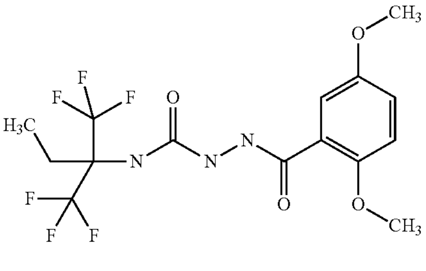 [SMILES: CCC(NC(=O)NNC(=O)c1cc(OC)ccc1OC)(C(F)(F)F)C(F)(F)F] | $^1$H NMR in $CD_3OD$: δ 7.49 (s, 1H), 7.10 (s, 2H), 3.93 (s, 3H), 3.79 (s, 3H), 2.50 (q, 2H), 1.11 (t, 3H); MS $ESI^+$ m/z 417.9 $(M + H)^+$ | N-[1,1-bis(trifluoromethyl)propyl]-2-(2,5-dimethoxybenzoyl)hydrazinecarboxamide |
| 107[3] | 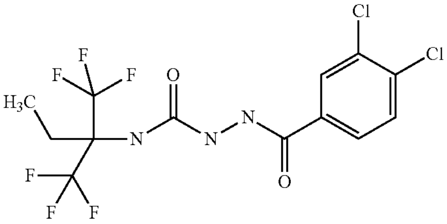 [SMILES: CCC(NC(=O)NNC(=O)c1ccc(Cl)c(Cl)c1)(C(F)(F)F)C(F)(F)F] | $^1$H NMR in DMSO-$d_6$: δ 10.54 (s, 1H), 8.29 (s, 1H), 8.13 (s, 1H), 7.84 (m, 2H), 7.46 (s, 1H), 2.41 (q, 2H), 1.03 (t, 3H) | N-[1,1-bis(trifluoromethyl)propyl]-2-(3,4-dichlorobenzoyl)hydrazinecarboxamide |

-continued

| Example Number | Structure | NMR/MS Data | Name |
|---|---|---|---|
| 108[3] | 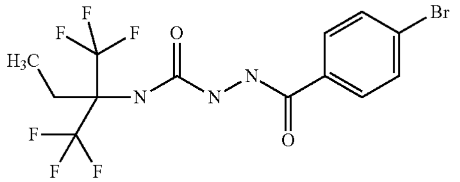 [SMILES: CCC(NC(=O)NNC(=O)c1ccc(Br)cc1)(C(F)(F)F)C(F)(F)F] | $^1$H NMR in $CD_3OD$: δ 7.78 (d, 2H), 7.65 (d, 2H), 2.49 (q, 2H), 1.10 (t, 3H) | N-[1,1-bis(trifluoromethyl)propyl]-2-(4-bromobenzoyl)hydrazinecarboxamide |
| 109[1] | 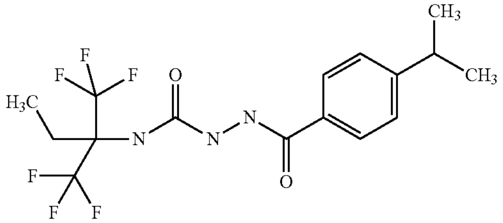 [SMILES: CCC(NC(=O)NNC(=O)c1ccc(C(C)C)cc1)(C(F)(F)F)C(F)(F)F] | $^1$H NMR in $CD_3OD$: δ 7.79 (d, 2H, 7.35 (d, 2H), 2.97 (m, 1H), 2.49 (q, 2H), 1.27 (d, 6H), 1.11 (t, 3H) | N-[1,1-bis(trifluoromethyl)propyl]-2-(4-isopropylbenzoyl)hydrazinecarboxamide |
| 110[1] | 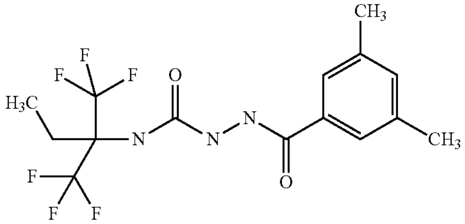 [SMILES: CCC(NC(=O)NNC(=O)c1cc(C)cc(C)c1)(C(F)(F)F)C(F)(F)F] | $^1$H NMR in $CD_3OD$: δ 7.47 (s, 2H),7.22 (s, 1H), 2.49 (q, 2H), 2.35 (s, 6H), 1.11 (t, 3H) | N-[1,1-bis(trifluoromethyl)propyl]-2-(3,5-dimethylbenzoyl)hydrazinecarboxamide |
| 111[4] | 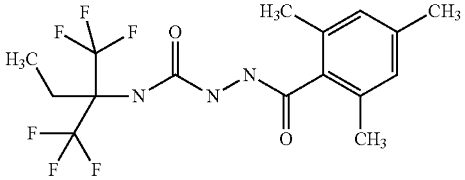 [SMILES: CCC(NC(=O)NNC(=O)c1c(C)cc(C)cc1C)(C(F)(F)F)C(F)(F)F] | $^1$H NMR in $CD_3OD$: δ 6.88 (s, 2H), 2.52 (q, 2H), 2.32 (s, 6H), 2.26 (s, 3H), 1.11 (t, 3H) | N-[1,1-bis(trifluoromethyl)propyl]-2-(mesitylcarbonyl)hydrazinecarboxamide |
| 112[3] | 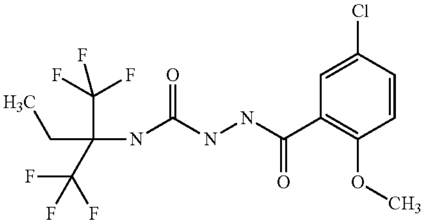 [SMILES: CCC(NC(=O)NNC(=O)c1cc(Cl)ccc1OC)(C(F)(F)F)C(F)(F)F] | $^1$H NMR in $CD_3OD$: δ 7.86 (d, 1H), 7.50 (dd, 1H), 7.16 (d, 1H), 3.97 (s, 3H), 2.48 (q, 2H), 1.10 (t, 3H) | N-[1,1-bis(trifluoromethyl)propyl]-2-(5-chloro-2-methoxybenzoyl)hydrazinecarboxamide |

[1]Purified by HPLC; 98% purity.
[2]Purified by HPLC; 99% purity.
[3]Purified by HPLC; 97% purity.
[4]Purified by HPLC; 96% purity.

Assay 1

Approximately 400,000 compounds from the compound library were tested in this assay. Assay plates were set up as follows. Vero cells were plated at 80% confluency on 96-well plates. Test compounds (80 per plate) from the library were added to wells at a final concentration of 5 μM. Tacaribe virus (TRVL 11573) was then added at a virus dilution that would result in 90% CPE after 5 days (pre-determined as an 800-fold dilution of the virus stock; multiplicity of infection [MOI] approximately 0.001). Plates were incubated at 37° C. and 5% $CO_2$ for 5 days, then fixed with 5% glutaraldehyde and stained with 0.1% crystal violet. The extent of virus. CPE was quantified spectrometrically at $OD_{570}$ using a Molecular Devices VersaMax Tunable Microplate Reader. The inhibitory activity of each compound was calculated by subtracting from the $OD_{570}$ of test compound well from the average $OD_{570}$ of virus-infected cell wells, then dividing by the average $OD_{570}$ of mock-infected cell wells. The result represents the percent protection against Tacaribe virus CPE activity conferred by the compound. "Hits" in this assay were defined as compounds that inhibited virus-induced CPE by greater than 50% at the test concentration. Of the approximately 400,000 compounds screened in the Tacaribe virus HTS campaign, 2,347 hits were identified (0.58% hit rate).

Quality hits are defined as inhibitor compounds (hits) that exhibit acceptable chemical structures, antiviral potency and selectivity, and spectrum of antiviral activity. Specifically, compounds identified as hits in HTS assays (described above) were evaluated against four criteria: (i) chemical tractability, (ii) inhibitory potency, (iii) inhibitory selectivity and, (iv) antiviral specificity. Based on the HTS parameters, all hits have $EC_{50}$ values <5 μM. The chemical structures of compounds that met this initial criterion were visually examined for chemical tractability. A chemically tractable compound is defined as an entity that is synthetically accessible using reasonable chemical methodology, and which possesses chemically stable functionalities and (potential) drug-like qualities. Hits that passed this medicinal chemistry filter were evaluated for their inhibitory potency. $EC_{50}$ values were determined from a plot of the compound inhibitory activity typically across eight compound concentrations (50, 15, 5, 1.5, 0.5, 0.15, 0.05 and 0.015 uM). To assess whether the hit is a selective inhibitor, the effect on cellular functions was determined using a standard cell proliferation assay. A 50% cytotoxicity concentration (CCso) was determined using a tetrazolium-based colorimetric method, which measures the in situ reduction of 3-(4,5-dimethylthiazol-2-yl)-2,5-diphenyl tetrazolium bromide (MTT) to insoluble blue formazan crystals by mitochondrial enzymes in metabolically active cells. Solubilized crystals were quantified spectrometrically. Using the $EC_{50}$ and $CC_{50}$ values, a Selective Index (SI) was calculated ($SI═CC_{50}/EC_{50}$). Hits with SI values of at least 10 were considered further.

The specificity of the antiviral activity exhibited by hit compounds was determined by testing the compounds against a number of related and unrelated viruses. Compounds are tested against a variety of unrelated DNA (HSV, CMV, vaccinia virus) and RNA (RSV, rotavirus, Rift Valley fever, Ebola virus, Ebola GP-pseudotype, Lassa GP-pseudotype, I IIV env-pseudotype) viruses. Compounds that will be selected for further development are those that are selective against the selected original target virus and inactive against unrelated viruses.

| Example Number | Tacaribe $EC_{50}$<br>A = <0.5 μM<br>B = 0.5 to <1.0 μM<br>C = 1.0 to <5 μM<br>D = ≥5 μM | Candide 1<br>A = <0.5 μM<br>B = 0.5 to <1.0 μM<br>C = 1.0 to <5 μM<br>D = 5≥ μM |
|---|---|---|
| 1 | A | |
| 2 | A | |
| 3 | A | |
| 4 | A | |
| 5 | A | |
| 6 | A | |
| 7 | A | |
| 8 | A | |
| 9 | A | |
| 10 | A | |
| 11 | A | |
| 12 | A | |
| 13 | A | |
| 14 | B | |
| 15 | B | |
| 16 | B | |
| 17 | B | |
| 18 | B | |
| 19 | B | |
| 20 | B | |
| 21 | B | C |
| 22 | B | |
| 23 | B | |
| 24 | C | |
| 25 | C | |
| 26 | C | |
| 27 | C | |
| 28 | C | |
| 29 | C | |
| 30 | C | |

-continued

| Example Number | Tacaribe $EC_{50}$<br>A = <0.5 μM<br>B = 0.5 to <1.0 μM<br>C = 1.0 to <5 μM<br>D = ≥5 μM | Candide 1<br>A = <0.5 μM<br>B = 0.5 to <1.0 μM<br>C = 1.0 to <5 μM<br>D = 5≥ μM |
|---|---|---|
| 31 | C | |
| 32 | C | |
| 33 | C | |
| 34 | C | |
| 35 | C | |
| 36 | C | |
| 37 | C | |
| 38 | C | |
| 39 | C | D |
| 40 | C | |
| 41 | C | |
| 42 | C | |
| 43 | C | |
| 44 | C | |
| 45 | C | |
| 46 | D | |
| 47 | D | |
| 48 | D | |
| 49 | D | |
| 50 | D | |
| 51 | A | |
| 52 | A | |
| 53 | B | |
| 54 | B | |
| 55 | B | |
| 56 | B | |
| 57 | C | |
| 58 | C | |
| 59 | C | |
| 60 | C | |
| 61 | C | |
| 62 | C | |
| 63 | C | |
| 64 | C | |
| 65 | C | |
| 66 | C | |
| 67 | C | |
| 68 | C | |
| 69 | C | |
| 70 | C | |
| 71 | C | |
| 72 | C | |
| 73 | C | |
| 74 | C | |
| 75 | C | |
| 76 | C | |
| 77 | C | |
| 78 | C | |
| 79 | C | |
| 80 | C | |
| 81 | C | |
| 82 | C | |
| 83 | C | |
| 84 | C | |
| 85 | D | |
| 86 | D | |
| 87 | D | |
| 88 | D | |
| 89 | D | |
| 90 | D | |
| 91 | D | |
| 92 | D | |
| 93 | D | |
| 94 | D | |
| 95 | D | |
| 96 | D | |
| 97 | D | |
| 98 | D | |

Assay 2

A chemical library was created and screened that represents a broad and well-balanced collection of 400,000 compounds accumulated over a number of years from a variety of distinct sources. The library achieves broad coverage across property space involving the following chemical descriptors: calculated logarithm of n-octanol/water partition coefficient (ClogP), polar (water-accessible surface area (PSA), globularity (three dimensional structure) and molecular weight (average: 394.5 daltons).

Cells and Viruses

Vero (African green monkey kidney epithelial, ATCC #CCL-81) cells were grown in Eagle's minimum essential medium (MEM, Gibco) supplemented with 2 mM L-glutamine, 25 μg/ml gentamicin, and 10% heat-inactivated fetal bovine serum (FBS). For infection medium (IM), the serum concentration was reduced to 2%. HEp-2 cells (human carcinoma of the larynx epithelial; ATCC 4CCL-23) were cultured in MEM containing 10% heat-inactivated FBS and 1% penicillin/streptomycin. MRC-5 cells (human normal lung fibroblast; ATCC #CCL-171) were cultured in MEM containing 10% heat-inactivated EBS, 1% penicillin/streptomycin, 1% L-glutamine (Invitrogen 25030-081), 1% Non-Essential Amino Acids (Invitrogen #11140-050), 1% sodium pyruvate (Invitrogen #11360-070), and 2% sodium bicarbonate. MA 104 cells (epithelial African green monkey kidney, ATCC CRL-2378.1) were cultured in MEM with 1% penicillin/streptomycin, 1% L-glutamine, 1% Non-Essential Amino Acids, 1% sodium pyruvate, and 2% sodium bicarbonate and 62.5 ug/ml trypsin and no serum during virus infection. All cell lines were incubated at 37° C. and 5% $CO_2$. Respiratory syncytial virus (RSV; A isolate), lymphocytic choriomeningitis virus (LCMV; Armstrong E350 isolate), cytomegalovirus (CMV; AD-169 isolate), herpes simplex virus I (HSV-1; KOS isolate), Vaccinia virus (Strain WR), Tacaribe virus (strain TRVL 11573) and rotavirus (strain WA) were obtained from ATCC (#VR-1422, #VR-1540, #VR-134, #VR-538, #VR-1493, #VR-1354, #VR-114, and #VR-2018 respectively). Candid 1 and Amapari BeAn 70563 were obtained from Dr. Robert Tesh at the University of Texas Medical Branch (Galveston, Tex.). Work done with BSL 4 viruses (Lassa, Machupo, Guanarito, and Junin) as well as severe acute respiratory syndrome-associated coronavirus (SARS-CoV) was conducted by collaborators at USAMRIID (Fort Detrick, Md.).

Antiviral Assays for Specificity Screening: Cytopathic Effect ("CPE") Assay Virus Plaque Reduction Assay, and ELISA A viral CPE assay was used to evaluate the antiviral effect of compounds against Tacaribe virus (Vero cells), Candid-1 vaccine virus (Vero cells), Amapari virus (Vero cells), SARS-CoV (Vero cells), HSV-1 (Vero cells), RSV (HEp-2 cells), vaccinia virus (Vero cells), and Rotavirus (MA104). An enzyme-linked immunosorbent assay ("ELISA") was used to evaluate the antiviral effect of compounds against CMV (MRC-5 cells) and LCMV (Vero cells). All of these assays were carried out in the appropriate media containing 2% heat-inactivated FBS. Ninety-six-well cell culture plates were seeded 24 hours before use with $1.5\times10^4$ (Vero), $2.2\times10^4$ (HEp-2 and MA 104), and $4.5\times10^4$ (MRC-5) cells per well. For compound susceptibility testing, compounds (solubilized with 100% DMSO) were added to duplicate wells at final concentrations of 50, 15.8, 5, 1.6, 0.5, 0.16, 0.05, 0.016 and 0 μM. The final concentration of DMSO in the assays was 0.5%. Virus stocks were titrated in a separate experiment to determine the concentration that resulted in 90% destruction of the cell monolayer (CPE assay) after 3 days (HSV-1, Rotavirus and vaccinia) or 4 days (SARS-CoV, RSV, Tacaribe virus, Candid 1 vaccine virus and Amapari virus) or the concentration that generated an ELISA signal of 2.5 at an optical density of 650 nm ($OD_{650}$) after 3 days (LCMV) or 4 days (CMV). These pre-established dilutions of virus were added to wells containing serial dilutions of compound. Uninfected cells and cells receiving virus without compound were included on each assay plate. In addition, reference agents, when available, were included on each assay plate (gancyclovir for HSV-1 and CMV, Sigma #G2536; ribavirin for LCMV and RSV, Sigma #R9644; and rifampicin for vaccinia virus, Sigma #R3501). Plates were incubated at 37° C. and 5% $CO_2$ for either 3 days (HSV-1, Rotavirus, LCMV, Vaccinia virus) or 4 days (Tacaribe virus, Amapari virus, Candid I virus, SARS-CoV, RSV, and CMV). HSV-1, SARS-CoV, Rotavirus, Vaccinia virus, RSV, Tacaribe virus, Amapari virus, Candid 1 vaccine virus infected plates were processed for crystal violet staining while plates infected with CMV and LCMV were processed for ELISA analysis. For crystal violet staining, the plates were fixed with 5% glutaraldehyde and stained with 0.1% crystal violet. After rinsing and drying, the optical density at 570 nm ($OD_{570}$) was measured using a Microplate Reader. For ELISA analysis, the medium from the LCMV and CMV-infected plates was removed and the cells were fixed with 100% methanol (Fisher, CAS #67-56-1, HPLC grade) for 20 minutes at room temperature. The methanol solution was removed and the plates were washed 3 times with PBS. Non-specific binding sites were blocked by the addition of 130 μL of Superblock Blocking Buffer (Pierce #37515) for 1 hour at 37° C. The blocking agent was removed and the wells were washed 3 times with PBS. Thirty μL of a 1:20 dilution of LCMV Nuclear Protein (NP) specific monoclonal antibody (generous gift of Juan Carlos de la Torre, The Scripps Research Institute, La Jolla Calif.) or 30 μL of a 1:200 dilution of CMV (protein 52 and unique long gene 44 product) specific cocktail monoclonal antibodies (Dako, #M0854) in Superblock Blocking Buffer containing 0.1% Tween-20 was added. Following 1 hour incubation at 37° C., the primary antibody solution was removed and the wells were washed 3 times with PBS containing 0.1% Tween-20. Forty μL of goat anti-mouse horseradish peroxidase conjugated monoclonal antibody (Bio-Rad #172-1011) diluted 1:4000 (LCMV) or 1:400 (CMV) in Superblock Blocking Buffer containing 0.1% Tween-20 was added to the wells and the plates were incubated for 1 hour at 37° C. The secondary antibody solution was removed and the wells were washed 5 times with PBS. The assay was developed for 15 minutes by the addition of 130 μL of 3,3',5,5-tetramethylbenzidine substrate (Sigma #T0440) to quantify peroxidase activity. The $OD_{650}$ of the resulting reaction product was measured using a Molecular Devices Kinetic Microplate Reader with a 650 nm filter.

Antiviral activity against Tacaribe virus was evaluated by three methods: CPE Assay, Plaque Reduction, and Virus Yield Inhibition Assay. For the FITS CPE Assay, Vero cells were plated at 80% confluency on 96-well plates. Test compounds (80 per plate) from the library were added to wells at a final concentration of 5 μM. Tacaribe virus was then added at a virus dilution that would result in 90% CPE after 5 days (multiplicity of infection ("MOI") approximately 0.001). Plates were incubated at 37° C. and 5% $CO_2$ for 5 days, then fixed with 5% glutaraldehyde and stained with 0.1% crystal violet. The extent of virus CPE was quantified spectrometrically at $OD_{570}$ using an Envision Microplate Reader. The inhibitory activity of each compound was calculated by subtracting from the $OD_{570}$ of test compound well from the average $OD_{570}$ of virus-infected cell wells, then dividing by the average $OD_{570}$ of mock-infected cell wells. The result represents the percent protection against Tacaribe virus CPE activity conferred by each compound. "Hits" in this assay were defined as compound that inhibited virus-induced CPE by greater than 50% at the test concentration (5 mM). Hits that possessed chemical tractability were further evaluated for their inhibitory potency. The inhibitory concentration 50% ($EC_{50}$) values were determined from a plot of the compound inhibitory activity following the CPE assay across eight compound concentrations (50, 15, 5, 1.5, 0.5, 0.15, 0.05 and 0.015 μM). All determinations were performed in duplicate.

In the Plaque Reduction Assay, Vero cell monolayers grown in 6-well plates were infected with about 50 PFU/well in the absence or presence of various concentrations of the compounds. After 1 h of virus adsorption at 37° C., residual inoculum was replaced by a 50:50 mix of 1% seaplaque agarose (in de-ionized water) and 2×MEM. Plaques were counted after 5-7 days of incubation at 37° C. The $EC_{50}$ was calculated as the compound concentration required to reduce virus plaque numbers by 50%. Under BSL 4 conditions at USAMRIID the plaque reduction assays (with Lassa, Machupo, Guanarito, and Junin viruses) were performed as follows: 200 PFU of each virus was used to infect Vero cells. After virus adsorption, cell monolayers were rinsed and overlaid with complete medium containing 1% agarose and either lacking test compound or with different concentrations ranging from 15 μM to 0.05 μM. After 5 days incubation at 37° C., the monolayers were stained with neutral red and the numbers of plaques were counted.

In Virus Yield Reduction Assays, Vero cells grown in 24-well plates were infected with Tacaribe virus at a multiplicity of infection ("MOI") of 0.1 in the presence of different concentrations of the compounds, two wells per concentration. After 48 h of incubation at 37° C. virus was harvested and the virus yields were determined by plaque formation in Vero cells. The $EC_{50}$ values were calculated as indicated above and similar calculations were performed to determine $EC_{90}$ and $EC_{99}$.

Cytotoxicity Assay

Cell viability was measured by a cell proliferation assay to determine a compound's effect on cellular functions so that a 50% cytotoxicity concentration ($CC_{50}$) could be calculated; the ratio of this value to the $EC_{50}$ is referred to as the selective index (S.I.=$CC_{50}$/$EC_{50}$). Two types of assays were used to determine cytotoxicity. One was a colorimetric method that measures the reduction of 3-(4,5-dimethylthiazol-2-yl)-2,5-diphenyl-tetrazolium bromide (MTT), and the other uses fluorimetry to measure the reduction of resazurin (Alamar Blue). Both methods produced similar data. Confluent cultures in 96-well plates were exposed to different concentrations of the compounds, with two wells for each concentration, using incubation conditions equivalent to those used in the antiviral assays.

Medicinal Chemistry

Several potent compounds were identified by the Tacaribe HTS and were grouped into several clusters of structure type. One cluster of compounds, with ST-336 (FW=407.3) representing the prototype based on antiviral activity and chemical tractability, was chosen for further development. Through retrosynthetic analysis of ST-336, it was determined that a library of analogues could be prepared convergently in a single synthetic step by combining an isocyanate with an acyl hydrazide. Using this chemistry, 165 analogues were prepared and the most potent examined for in vitro metabolism.

Time of Addition Experiment

This experiment was designed to characterize the mechanism of action of the anti-viral compounds. Vero cells were grown in 24 well culture plates. The medium was removed when the cells reached 70-80% confluency and replaced with infection medium. Cells were infected with Tacaribe virus at MOI=0.1. After 1 hour adsorption, the viral inoculum was removed and replaced with fresh infection medium. Duplicate wells were treated with 3 μM ST-336 1 h prior to infection, at the time of infection or at specific times post infection (from 1 to 20 h p.i.). Control infected cell cultures were treated with drug vehicle (DMSO) only. ST-336 was removed 1 hour post absorption and the monolayer was washed twice with cold PBS-M and replaced with fresh infection medium. The cells were harvested at 24 h p.i. and were titrated as described above.

In a separated experiment, Vero cells plated in a 6 well dish were infected with Tacaribe virus at MOI=4. Absorption was carried out for 1 hour. Three μM of ST-336 was added for 1 hour at 1 hour before infection, during infection, and 1 hour following infection. Following drug addition and virus infection, monolayers were washed 3 times with complete media. Four hours following last drug addition, monolayers were overlaid with 1% agarose without compound until plaques developed. At 5 to 7 days post infection, monolayers were fixed, crystal violet stained and plaque numbers counted.

Assay for Compound Binding to Intact Virus

This experiment was designed to test the binding/fusion inhibitory properties of ST-336 towards Tacaribe virus. Vero cells were grown in MEM with 2% fetal calf serum. For this experiment, cells were grown to 70-80% confluency in 24-well culture plates. In one set of tubes Tacaribe virus (4000 pfu) was treated with 1% DMSO, serially diluted tenfold in infection medium and treated with the specific concentrations of ST-336 (400 pfu+0.5 μM ST-336, 40 pfu+0.05 μM ST-336) or DMSO only (400 pfu or 40 pfu+DMSO). In another set of tubes Tacaribe virus (4000 pfu) was treated with 5 μM ST-336 then serially diluted tenfold in infection medium. The suspensions were plated in wells and after adsorption for one hour inocula were removed and overlaid with 0.5% Seaplaque agarose in MEM. The plate was incubated at 37° C. until cytopathic effect was observed in the DMSO control well. The cells were fixed with 5% gluteraldehyde and stained with 0.1% crystal violet for plaque visualization.

Another assay employed to test the binding properties of ST-336 to pre-fusion F-proteins on virions was a dialysis experiment. Purified Tacaribe virus (1000 pfu) was incubated with 5 μM of ST-336 or 0.5% DMSO. The suspensions were dialyzed overnight at 4° C. in a dialysis chamber. Twenty four hours post dialysis viral suspensions were titrated on Vero cells. Post one hour adsorption, inocula were removed and a 0.5% Seaplaque agarose in MEM overlay was applied. The plate was incubated at 37° C. until cytopathic effect was observed. The cells were fixed with 5% gluteraldehyde and stained with 0.1% crystal violet. To confirm absence of free drug in dialysed virus-drug sample, virus was spiked in dialysed mixture at time of infection and plaques developed as described above.

Isolation of Drug Resistant Variant Viruses

Initially, single plaques of WT Tacaribe virus were isolated. For this plaque-purification Vero cells in a 6-well plate were infected with 50 pfu/well of WT Tacaribe virus for 1 hour at 37° C. Following virus adsorption the inoculum was removed and each well was overlaid with 0.5% Seaplaque agarose in MEM and incubated at 37° C. until plaques were visible (5-7 days). Four plaques were picked and further amplified in Vero cells in a 24-well plate until CPE developed (5-7 days). Virus-infected cell extracts were harvested by scraping cells into the media and then collected in 1.5-ml microcentrifuge tubes. Each plaque-purified isolate was further amplified in 150 mm plates, and then each virus stock that originated from one virus plaque was titrated.

For the isolation of compound-resistant Tacaribe virus variants, each wild type plaque-purified isolate was titrated in the presence of 3 μM ST-336 as described. Vero cells in a 6-well plate were infected with $10^4$-$10^6$ pfu/well in media containing 3 μM ST-336 for 1 hour, then the cells were overlaid with 0.5% seaplaque agarose in MEM containing 3 μM ST-336 and incubated until plaques formed. Plaques were picked and used to infect Vero cells in a 24-well plate without compound. When CPE developed the infected wells were harvested. Each drug-resistant isolate was then titrated on a 96-well plate in 0.5 log dilutions, starting with 25 μL of pure virus stock, without compound and with 1 μM and 3 μM ST-336. Each mutant went through several rounds of plaque purification before final virus stocks were made.

Sequencing

RNA was extracted from each of the Tacaribe WT isolates (1-4) and four of the drug resistant isolates (DR#1-4) and used for reverse transcription PCR. Primers specific to the GPC (Tac-forward: 5' GCCTAACTGAACCAGGTGAATC (SEQ ID NO:1) and Tac-reverse: 5' TAAGACTTCCGCACCACAGG (SEQ ID NO:2)) from Tacaribe were used for amplification and sequencing.

Solubility

Two tests were used to assess compound solubility: solubility in cell culture medium with and without various concentrations of serum and solubility in aqueous buffer at pH 7.4. The solutions were stirred overnight and then filtered through an Amicon Centrifree YM-30 column with a 30,000 MW cutoff to remove potentially precipitated compound and compound bound to protein. The compound was quantified by LC/MS or UV spectrometry.

Stability

In vitro metabolic stability was determined by Absorption Systems (Exton, Pa.) using the 9000×g supernatant (S9) of homogenized liver from various species as a source of oxidative conjugation enzymes (e.g., cytochromes P450, UdP-glucuronosyl transferase) that are known to be the primary pathways of biotransformation for most drugs. The metabolic stability was measured as the persistence of parent compound over incubation time in the S9 fractions by mass spectrometry. Briefly, human, rat, mouse, and guinea pig S9 fractions were obtained from Xenotech (Lenexa, Kans.). The reaction mixture, minus cofactor cocktails, was prepared (1 mg/ml liver S9 fractions, 1 mM NADPH, 1 mM UDPGA, 1 mM PAPS, 1 mM GSH, 100 mM potassium phosphate pH 7.4, 10 mM magnesium chloride, 10 μM test article) and equilibrated at 37° C. for 3 min. An aliquot of reaction mixture was taken as a negative control. The reaction was initiated by the addition of cofactor cocktails to the reaction mixture only, and then the reaction mixture and negative control were incubated in a shaking water bath at 37° C. Aliquots (100 μl) were withdrawn in triplicate at 0, 15, 30, and 60 minutes and combined with 900 μl of ice-cold 50/50 acetonitrile/$dH_2O$ to terminate the reaction. Each sample was analyzed via LC/MS/MS. The natural log of the percent remaining was plotted versus time. A linear fit was used to determine the rate constant. The fit was truncated when percent remaining of test article was less than 10%. The elimination half-lives associated with the disappearance of test and control articles were determined to compare their relative metabolic stability.

Genotoxicity

An exploratory bacterial mutagenicity assay (Ames test) was used to assess the potential of the compound genotoxicity. This assay utilized *S. typhimurium* tester strains TA7007 and TA7006 (single base pair mutations) and TA98 (frame shift mutation) with and without metabolic activation (Arochlor-induced rat liver S9) as described previously.[32]

Pharmacokinetic ("PK") Assessments in Rats and Newborn Mice

Analysis of the oral pharmacokinetics of selected compounds was performed in Sprague Dawley rats in a single dose study with serum samples taken over a 24 h period. For the newborn mice PK evaluation, 4 day old BALB/c mice were dosed intraperitoneally (IP) and serum samples were taken over a 24 hour period. A 50 μl aliquot of plasma was combined with 150 μl of 100% acetonitrile containing an internal standard (100 ng/ml tolbutamide) in a 1.5 ml centrifuge tube. Samples were vortexed and centrifuged at 13,000 rpm for ten minutes. An 80 μl aliquot of the resulting supernatant was then transferred to an HPLC for vial analysis. Plasma levels of each compound were determined by LC/MS/MS, and pharmacokinetic parameters were determined using WinNolin software.

Efficacy in Newborn Mouse Model

To determine tolerability of ST-294, newborn (4 days old) BA LF3/c mice were given IP dosages of 0 (vehicle), 10, 25, or 100 mg/kg/day of ST-294 for 5 days with assessment of clinical status daily.

To test the efficacy of ST-294 in the Tacaribe newborn mouse model, four day old BALB/c mice (8 per dose group) were challenged with $3\times10^3$ PFU ($30\times LD_{50}$) of Tacaribe virus per mouse by IP injection with death as the end point. Mice were either treated with placebo (vehicle), ribavirin (MP Biomedical) administered IP at 25 mg/kg once a day for 10 days, or ST-294 administered IP at 100 mg/kg once a day or at 50 mg/kg twice a day for 10 days. Mice were monitored daily and weighed every other day throughout the study. Any mice showing signs of morbidity were euthanized by $CO_2$ asphyxiation. All animal studies conformed to the Institute for Laboratory Animal Research and were approved through appropriate IACUC review.

Results

Homology Between Tacaribe and Other BSL 4 NWA

There are currently 23 recognized viral species of the Arenaviridae family.[4] These viruses have been classified into two groups: the Old World (Lassa/LCM) arenaviruses and the New World (Tacaribe complex) group. The New World Tacaribe complex comprises three phylogenetic lineages, designated clades A, B, and C. Clade B includes the prototypic Tacaribe virus, Amapari virus and the four South American Category A pathogens (Junin, Machupo, Guanarito and Sabia). Tacaribe virus is 67% to 78% identical to Junin virus at the amino acid level for all four viral proteins.[23] Working with authentic Category A arenaviruses requires maximum laboratory containment (BSL-4), and therefore presents significant logistical and safety issues. Since Tacaribe virus is closely related to the Category A pathogens it was chosen as a surrogate BSL 2 NWA for the development of a HTS assay to screen for inhibitors of virus replication.

Tacaribe HTS Assay

Since Tacaribe virus grows well in cell culture and causes clear virus-induced cytopathic effect (CPE) a robust HIS CPE assay was developed in a 96-well plate. The CPE assay is a whole cell assay which allows for calculation of the selective index of the compounds and identification of inhibitors of any essential steps in the virus life cycle. Of the 400,000 compounds screened in the Tacaribe virus HTS assay, 2,347 hits were identified (0.58% hit rate). All of these hits had $EC_{50}$ values ≤5 μM. The 2,347 hits were then qualified based on four criteria: i) chemical tractability, ii) inhibitory potency, iii) inhibitory selectivity, and iv) antiviral specificity. A chemically tractable compound is defined as an entity that is synthetically accessible using reasonable chemical methodology, and which possesses chemically stable functionalities and potential drug-like qualities. Hits that passed this medicinal chemistry filter were evaluated for their inhibitory potency. $EC_{50}$, $CC_{50}$, and selective index (SI) values were determined to assess whether the hit was a selective inhibitor. Hits with SI values of at least 10 were considered further. Of the 2,347 hits identified, 36 compounds exhibited all the characteristics of quality hits. These compounds were chemically tractable, had $EC_{50}$ values ≤5 μM and SI values ≥10. Among the 36 quality hits, there were several clusters of structure type. One structure type was chosen for further development and ST-336 is the representative prototype for this series. ST-336 is a 407.33 dalton compound and its structure is shown in FIG. 1.

TABLE 1

Specificity of ST-336

| Virus (assay) | | ST-336 (μM) |
|---|---|---|
| NWA Tacaribe | | |
| (CPE) | EC50 | 0.055 |
| (CPE) | EC90 | 0.125 |
| (Virus yield) | EC90 | 0.068 |
| (Virus yield) | EC99 | 0.085 |
| (Plaque reduction) | EC50 | 0.100 |
| Candid1 (CPE) | EC50 | 0.062 |
| Amapari (CPE) | EC50 | >20* |
| Machupo (Plaque reduction) | EC50 | 0.150 |
| Guanarito (Plaque reduction) | EC50 | 0.300 |
| Junin (Plaque reduction) | EC50 | 0.150 |
| OWA | | |
| Lassa (plaque reduction) | EC50 | >20 |
| LCMV (Elisa) | EC50 | >20 |

Results represent the average of at least two independent determinations.
*20 μM represents limit of compound solubility Characterization of ST-336

As seen in Table I, ST-336 has submicromolar potency, good selectivity, and antiviral specificity against Tacaribe virus as well as the Category A NWA. Evaluation of ST-336 in a virus yield reduction assay against Tacaribe virus produced $EC_{90}$ and $EC_{99}$ values of 0.068 μM and 0.085 μM respectively. The $CC_{50}$ value for ST-336 on Vero cells is >20 μM, which represents the solubility limit of this compound in cell culture media, giving it a selective index of >363. The activity of ST-336 against Tacaribe virus was tested on multiple cell lines and all the $EC_{50}$ values were similar to those achieved on Vero cells (data not shown). When tested against several arenaviruses, ST-336 showed no inhibitory activity against OWA, either LCM virus or authentic Lassa virus (Table 1). This drug also lacked activity against the NWA Amapari virus. This was a surprising result given the close phylogenetic relationship between Amapari and Tacaribe viruses.[23,19] This discrepancy is later discussed following sequencing of GP2 of all NWA. However, importantly ST-336 showed potent antiviral activity against the vaccine strain of Junin virus (Candid 1) as well as Machupo, Guanarito, and Junin (Table 1).

TABLE 2

Selectivity of ST-336

| Virus (assay) | ST-336 EC50 (μM) |
|---|---|
| DNA viruses | |
| HSV-1 (CPE) | >20* |
| CMV (Elisa) | >20 |
| Vaccinia (CPE) | >20 |
| RNA viruses | |
| RSV-A (CPE) | >20 |
| Rotavirus (CPE) | >20 |
| SARS (CPE) | >20 |
| Ebola (CPE) | >20 |

Results represent the average of at least two independent determinations.
*20 μM represents limit of compound solubility The specificity of the antiviral activity exhibited by ST-336 was determined by testing against a number of related and unrelated viruses. As shown in Table 2, ST-336 showed no activity against a variety of unrelated DNA (HSV, CMV, vaccinia virus) and RNA (RSV, Rotavirus, SARS and Ebola virus) viruses.

Mechanism of Action of ST-336

Figure 2A:
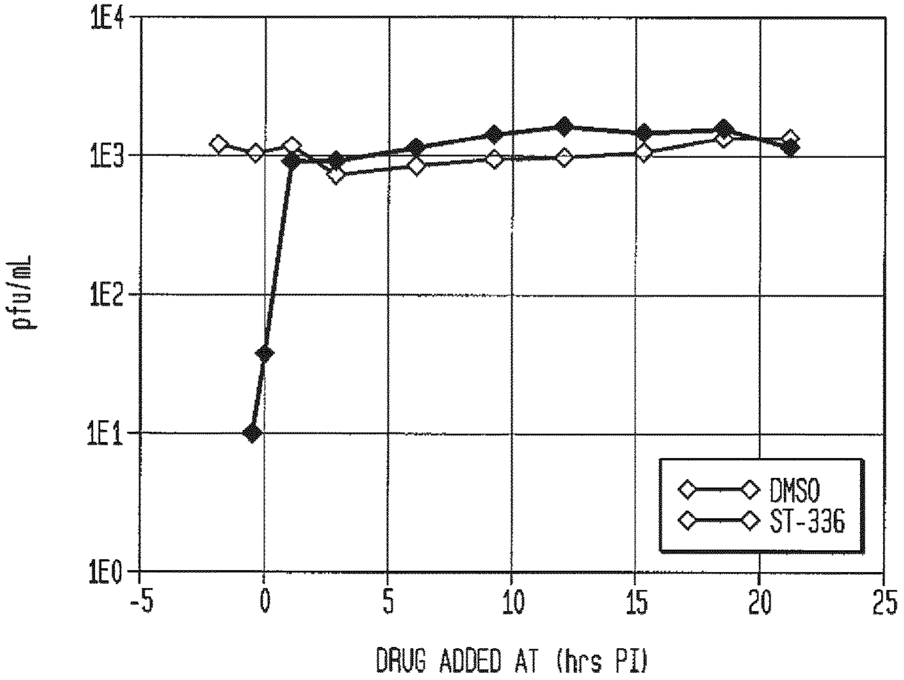
In FIG. 2A, Vero cells were infected with Tacaribe virus at a MOI=0.01. ST-336 was added prior to or during Tacaribe infection (−1, 3, 6, 9, 12, 15, 18 or 21 hours post-infection). At 24 hours post-infection, virus yields were determined by plaque assay.

A single cycle (24 h) time of addition experiment was done to determine when during the virus replication cycle ST-336 exerts its antiviral activity. The effect of ST-336 on Tacaribe virus yield was determined following addition of compound to Vero cell cultures at various times before or after infection. ST-336 was added at one hour before infection (−1 h), during virus adsorption (0 h), and at several times post-infection. Drug was kept, following sequential addition, on infected cell cultures for the entire time of the experiment. Control infected cultures were treated with drug vehicle (DMSO) only. At 24 hours post-infection, samples were collected, and virus yields were determined by plaque assay. As shown in FIG. 2A, ST-336 exerted its inhibitory effect only at the very early stage in the virus life cycle. Addition of ST-336 at any time points post-infection had no effect on virus yield. These data suggest that ST-336 is an early stage inhibitor of virus replication.

Figure 2B:
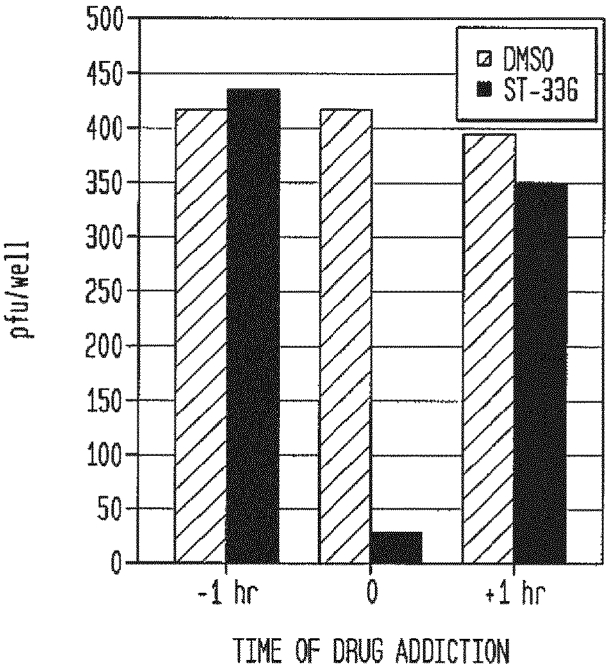
In FIG. 2B, Vero cells were infected with 400 pfu Tacaribe virus. ST-336 was added for 1 hour before the infection (−1), for 1 hour during adsorption (0), and for 1 hour after the infection (+1). Infected monolayers were washed with PBS and overlayed with medium containing agarose. Five days post-infection, cells were glutaraldehyde fixed and crystal violet stained prior to plaque counting.

These results were confirmed in a second type of time addition experiment. In this experiment, compound was spiked in the culture medium for only 1 hour, at 1 hour before infection (−1 h), during infection (0) and at 1 hour post infection (+1 h), and then removed. The cultures were washed to remove any residual compound and overlaid with agarose. Virus plaque numbers were then determined at 5 days post-infection. Data in FIG. 2B showed that while compound added before and after virus adsorption for 1 hour had no effect on plaque formation, compound added during the 1 h adsorption/entry process dramatically reduced Tacaribe plaque formation. These data are consistent with ST-336 being an adsorption/entry inhibitor.

Figure 3A:
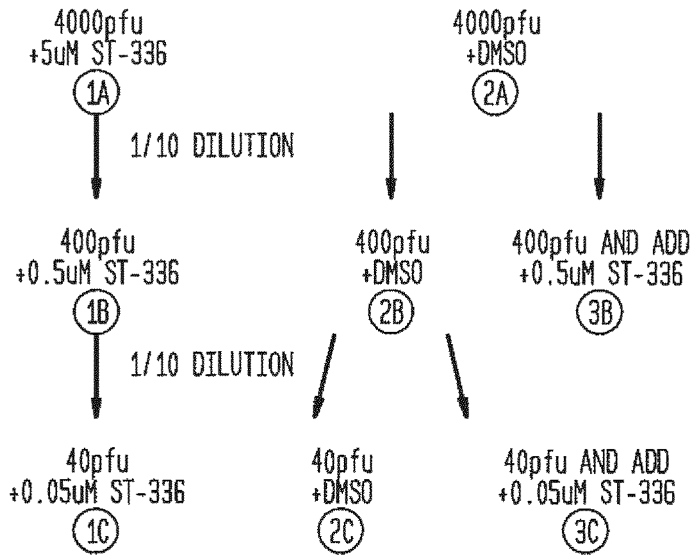
In FIG. 3A, a diagram of the virus dilution scheme prior to plating is provided. The virus mixed with ST-336 and diluted (left side) or virus diluted and ST-336 added after dilution (right side).
Figure 3B:
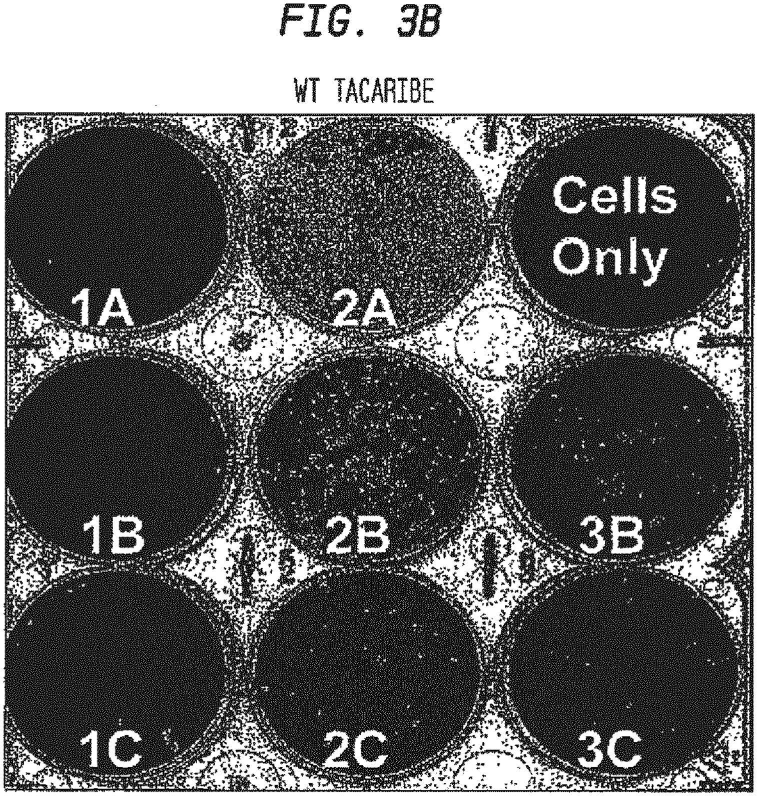
In FIG. 3B, pictures of the plaques that resulted after plating each dilution shown in FIG. 3A on Vero cells is provided.

Two approaches were taken to determine if ST-336 is binding to intact virions. In the first experiment, 1000 PFU of purified Tacaribe virus were incubated with ST-336 or DMSO and dialyzed overnight at 4° C. and titrated. While no virus were titrated from the dialyzed bag originally incubated with drug, more than 300 PFU of virus was titrated from the DMSO vehicle dialyzed bag (data not shown). No drug was biologically detected in the dialysis bag originally containing 5 μM of drug as measured by the incapability of the virus plus drug dialyzed mixture to inhibit freshly added Tacaribe virus (300 PFU). These data suggested that ST-336 binds intact virions with a very slow dissociation constant. In the second experiment (FIG. 3), Tacaribe virus was incubated in a test tube with 5 μM of ST-336 or DMSO. Serial 1:10 dilutions were performed and for some samples ST-336 was added as a specified dilution representing the concentration of drug expected following sample dilution. As virus and compound are diluted with media, the compound concentration will reach a concentration without an inhibitory effect, unless the compound was capable of binding to virus. Test virus without compound in the initial tube was also diluted in media and compound concentrations corresponding to that found in the tubes where virus and compound were diluted together was added to each virus dilution. Titration on Vero cells showed that ST-336 present in excess in the initial tube was carried over for two additional 1:10 dilutions through specific virus binding and inhibits virus infection. In contrast, when drug was added at a specified dilution virus was not inhibited to the same degree as virus diluted with drug (data not shown). These data suggest that ST-336 binds with at least a slow $K_{off}$ to intact protein present on Tacaribe virus.

Isolation of Drug Resistant Variants

The expected mutation rate of RNA viruses is very high (~1 mutant in 10,000) and a common approach to determining the target of an antiviral is to isolate virus resistance to the antiviral and then map the site of resistance. Virus variants with reduced susceptibility to ST-336 were isolated from wild type Tacaribc virus stocks plated in the presence of ST-336. The observed frequency of ST-336 drug resistant (ST-$336^{DR}$) variants was as expected for RNA viruses. Sixteen ST-$336^{DR}$ isolates from four independent wild type Tacaribe virus stocks were isolated and plaque purified three times. All ST-$336^{DR}$ isolates were tested for their ability to grow in the presence of ST-336. The growth of ST-$336^{DR}$ isolates was unaffected by the presence of ST-336 at concentrations that completely inhibited wild type Tacaribe virus replication (data not shown). The isolation and confirmation of drug resistant virus variants strongly suggest that ST-336 acts as a direct antiviral inhibitor.

Figure 4A:
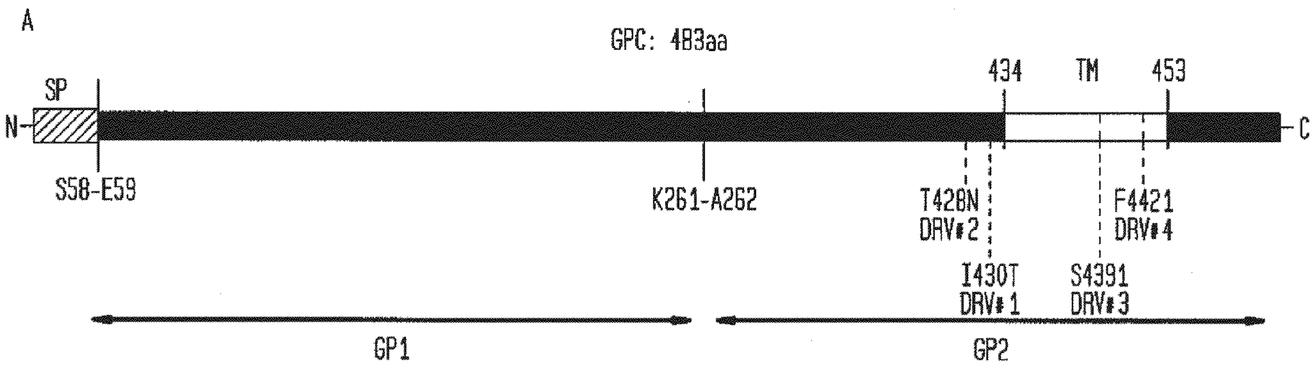
In FIG. 4A, a linear map of the glycoprotein precursor ("GPC") showing the location of the signal peptide ("SP"), transmembrane domain ("TM"), the cleavage site between GP1 and GP2 (K261-A262), the location of the four ST-336 resistant mutants ("DR #1-4"), and the amino acid change for each is provided.
Figure 4B:
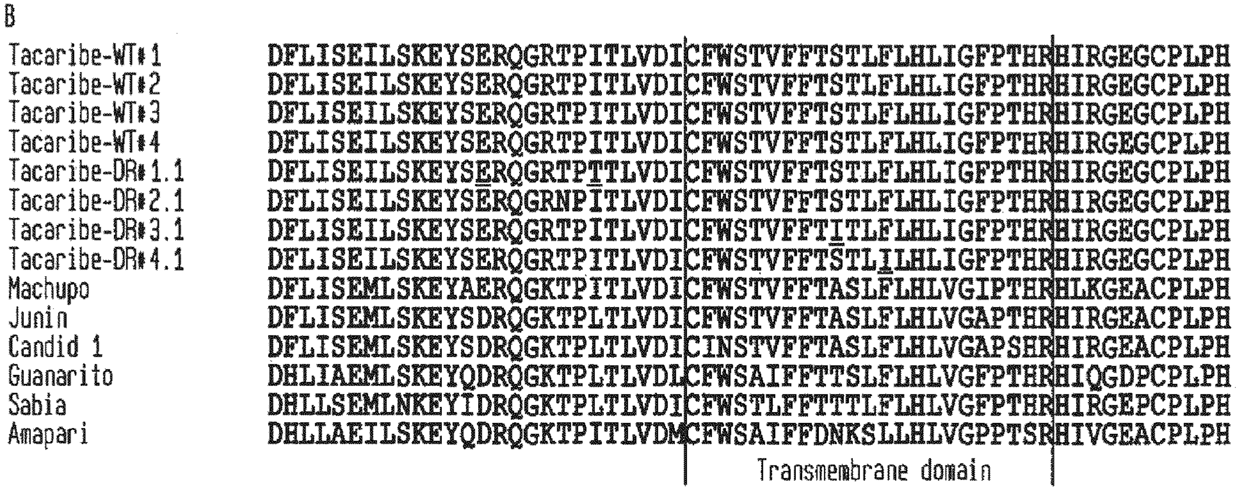
In FIG. 4B, the amino acid sequence alignment of GP2 from wild type NWA and ST 336 DRVs is shown. Shown is the amino acid sequence of the C-terminal portion of GP2 (amino acids 397 to 457) containing the transmembrane domain (marked by vertical lines), the location of the mutations for DR#1-4 (underlined), and the amino acid difference in Amapari (in bold).

To determine the genetic basis for resistance and the molecular target of ST-336, RNA was isolated from the wild type and ST-$336^{DR}$ isolates. Based on the time of addition experiments, it was suspected that the viral glycoproteins might be the target of ST-336. The entire glycoprotein precursor GPC region of the S segment was sequenced. Sequence analysis was performed on four wild type isolates (WT#1-4) and four ST-$336^{DR}$ isolates derived from drug selection applied to each corresponding parental wild type isolate (DR#1.1 from WT#1, DR#2.1 from WT#2, DR#3.1 from WT#3 and DR#4.1 from WT#4). The sequence analysis showed that the GPC gene from the four parental wild type isolates had identical sequences. When compared to the GPC sequences of four drug resistant variants, each possessed a single nucleotide change that in all cases resulted in an amino acid change. FIG. 4A shows the location of each of the mutations which are located in or around the transmembrane domain of GP2. The sequence alignments of the region of the GP2 containing the changes is presented in FIG. 4B. The single change in DR#1.1 was at amino acid position 418 (I418T), in DR#2.1 at amino acid 416 (T416N), in DR#3.1 at amino acid 433 (S4331) and in DR#4.1 at amino acid 436 (F4361). 1418 is similarly conserved (I or L, but never a T) in all Glade B New World arenavirus, while T416 is conserved among all Glade B NWA. F436 is similarly conserved with one exception; Amapari virus encodes a leucine at position 436. This change in Amapari virus may explain its lack of susceptibility to ST-336 (Table 2). I418, T416, S433 and F436 lie near the N-terminal and C-terminal limits of the putative transmembrane domain of GP2, a region known to play a vital role in enveloped virus fusion.[17,27,28,38,39] Taken together, these data suggest that amino acid changes in arenavirus GP2 at either position 416, 418, 433 or 436 arc sufficient to confer reduced susceptibility to ST-336 and arc consistent with the proposed fusion inhibition mechanism suggested by virological experiments.

Hit-to-Lead Optimization

Preliminary data showed that ST-336, while demonstrating interesting antiviral activity and specificity, had poor pharmacokinetic (PK) properties in rodents (mouse and rats, data not shown). In order to improve the PK properties of ST-336, a lead optimization chemistry campaign was initiated. The objective of the optimization program was to develop compounds that possess attributes consistent with the ultimate drug product profile. Lead optimization activities comprised a series of iterations involving design and chemical synthesis of analogs of the Lead structure, followed by a series of biological, physiochemical, and pharmacological evaluations of the new compounds. Chemical analogs flowed through a compound evaluation paradigm that involved first in vitro virological and cytotoxicity assessments, followed by a series of evaluations as listed: in vitro metabolic stability (S9), solubility, exploratory bacterial mutagenesis and pharmacokinetic assessments. 165 analogues were prepared and the most potent were examined for in vitro metabolism in S9 liver extracts. The most stable were dosed in rats, and ST-294 emerged as a potent, orally bioavailable representative of the compounds.

Characterization of ST-294

Figure 5:
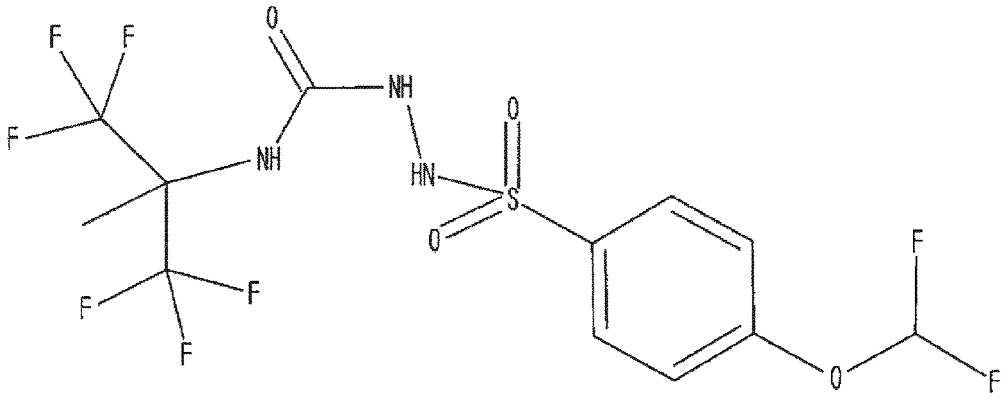
FIG. 5 provides the chemical structure, formula, and molecular weight for ST-294.

The structure of ST-294 (N-2-(1,1,1,3,3,3-hexafluoro-1-methylpropyl)-2-[(4-difluoromethoxyphenyl)sulfonyl]hydrazine-1-carboxamide) is show in FIG. 5. ST-294 was tested against the drug resistant Tacaribc mutants generated with ST-336 (DR#1-4) and all of the mutants elicited cross-resistance to ST-294 suggesting that this compound is targeting the same area of GP2 as ST-336 (data not shown). The activity of ST-294 against Tacaribe, Machupo, Guanarito, and Junin viruses was similar to that seen with ST-336 (Table 3). The $CC_{53}$ of ST-294 on Vero cells is >50 μM yielding a selective index of >416. Further characterization of ST-294 showed that this compound is soluble up to 23 μM in media containing 10% fetal calf serum and up to 480 μM in buffer at pH 7.4 (Table 3). The metabolic stability of ST-294 was tested in S9 liver extracts from rat, mouse, human, and guinea pigs and was found to be most stable in human S9 followed by mouse, rat and guinea pig respectively (Table 3). Analysis of the oral pharmacokinetics of ST-294 was initially performed in the rat as this species is well characterized for this type of study. The rats were dosed with ST-294 by oral gavage and samples were taken over a 24 h period. Serum levels were very high ($C_{max}$=6670 ng/ml) and ST-294 has good oral bioavailability (68.2%) (Table 3).

TABLE 3

Characterization of ST-294

| Virus (assay) | | ST-294 |
|---|---|---|
| Tacaribe | | |
| (CPE) | EC50 | 0.120 μM |
| (Plaque reduction) | EC50 | 0.100 μM |
| Machupo | | |
| (Plaque reduction) | EC50 | 0.300 μM |
| Guanarito | | |
| (Plaque reduction) | EC50 | 1.0 μM |

TABLE 3-continued

| Characterization of ST-294 | | |
|---|---|---|
| Virus (assay) | | ST-294 |
| Junin | | |
| (Plaque reduction) | EC50 | 0.300 μM |
| Properties | | |
| Solubility (0%, 2%, 10% FBS) | | 18, 21 and 23 μM |
| Solubility (pIon, pH 7.4) | | 480 μM |
| Stability (S9) rat/mouse/human/g.p | | 26/74/100/23 min |
| Genotoxicity (Ames test) | | negative |
| PK (rat/oral) | | |
| ½ life | | 2 hours |
| bioavailability (F) | | 68.2% |
| PK (newborn mouse/IP) | | |
| ½ life | | 3 hours |
| $C_{max}$ | | 2910 ng/ml |

Efficacy Study with ST-294 in Newborn Mouse Model

ST-294 has potent antiviral activity against NWA and good drug-like properties, so the next step was to test the ability of ST-294 to inhibit NWA-induced disease in an animal model. For the Category A agents, the experiments require BSL 4 containment. However, in an effort to obtain an initial readout, a Tacaribe virus challenge model in newborn mice was established. In preparation for this study, PK and tolerability experiments were performed with ST-294 in newborn mice prior to conducting an efficacy trial. Newborn (4 day old) BALB/c mice were dosed IP with 10 mg/kg of ST-294 and blood samples were collected for analysis. Relative to in vitro antiviral concentrations required to inhibit Tacaribe virus CPE ($EC_{50}$=66 ng/ml), mean plasma concentrations in newborn mice were well above this level for prolonged periods of time (>15× through 8 h and 6× at 24 h after dosing, data not shown). In this model the drug is delivered via the IP route due to the difficulty of performing multiple oral gavages on newborn mice. To test tolerability, newborn mice were given IP dosages ranging from 0-100 mg/kg/day of ST-294 for 5 days. Dosages of 100 mg/kg/day for 5 days were well tolerated by the newborn mice as there were no clinical signs of toxicity and the mice gained weight at the same rate as the control mice (data not shown). This highest tested concentration of ST-294 of 100 mg/kg/day was used in a Tacaribe animal efficacy study.

Figure 6:
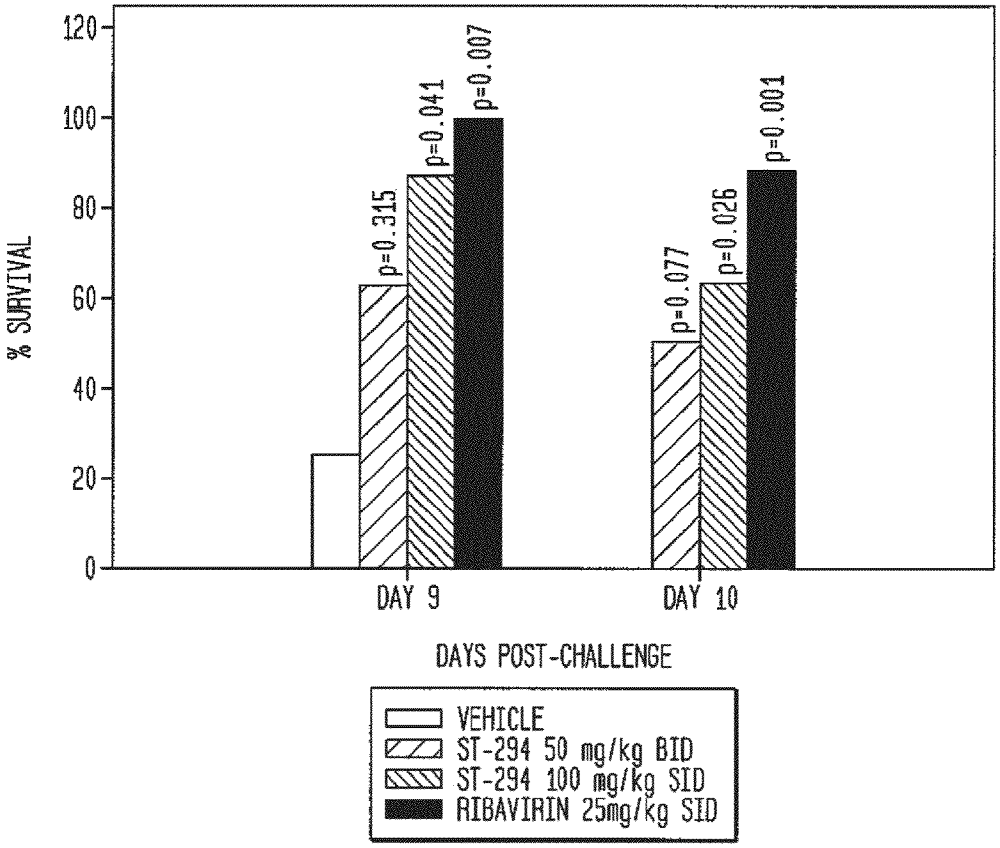
FIG. 6 shows the effect of ST-294 in newborn mice challenged with Tacaribe virus. Four day old BALB/c mice were infected IP with 30×LD50 Tacarbide virus and treated daily for 10 days with vehicle (control), ribavarin at 25 mg/kg, ST-294 twice a day (BID) at 50 mg/kg or once a day (SID) at 100 mg/kg. Shown in FIG. 6 are the percent survivors in each treatment group on day 9 and day 10 after infection.

The drug levels and half-life shown in the PK study in the newborn mice was not equivalent to that seen in the rats, but the serum levels seemed sufficient to perform a proof-of-concept animal study in the Tacaribe animal model. Four day old mice were challenged with 30×LD50 of Tacaribe virus and treated with placebo, ribavirin as a control or ST-294. As the results in FIG. 6 demonstrate, ST-294 showed efficacy in the Tacaribe infected newborn mice with both survival and a delay in death similar to the drug control (ribavirin). Taken together these data suggest that ST-294 is a promising and appropriate drug candidate to advance into definitive animal studies where guinea pigs and primates will be challenged with authentic NWA (Junin and Guanarito viruses) and treated at various times post infection and prophylactically with ST-294.

Discussion

Through a successful HTS and medicinal chemistry program, a NWA antiviral drug candidate, ST-294, has been identified. This drug potently and selectively inhibits NWA viruses in vitro including the 3 NIAID/CDC Category A viruses (Junin, Machupo, and Guanarito viruses). This compound was also evaluated for stability in S9 liver extracts and for its pharmacokinetic properties and was found to be metabolically stable and orally bioavailable. In a preliminary animal efficacy study, ST-294 showed significant protection against Tacaribe virus induced disease in newborn mice. Through mechanism of action studies it is apparent that this series of compounds targets GP2 and are viral entry inhibitors.

From the dialysis and dilution experiments (FIG. 3) it is apparent that the drug binds to virus and is carried over during dilutions. This phenomenon could potentially have an effect when titrating virus samples during other experiments. However, in the time of addition experiment, there was not enough drug carryover due to high dilution to affect the titers when added 1 hour or more after infection (FIG. 2).

Since ST-294 has better S9 stability than ST-336 does, it is thought that metabolism occurs at the methyl group on the aromatic ring (FIG. 1). The benzylic position is susceptible to oxidation. When there is no benzylic hydrogen present as in ST-294 (FIG. 2), the oxidation is blocked and thus eliminates the fastest metabolism pathway. The addition of the difluoromethoxy group in ST-294 gave this compound increased S9 stability, but did not reduce antiviral activity.

In the Tacaribe newborn mouse model the mice appear to die of a neurological disease (indicated by hindquarter paralysis) and it is not known whether ST-294 can cross the blood brain barrier. Also the drug levels and half-life of this drug candidate given IP in newborn mice is not as good as oral dosing in rats so serum levels and compound getting to the brain may have compromised the ability to obtain complete protection in this model. The more appropriate animal models for hemorrhagic fever caused by arenaviruses are in guinea pigs and non-human primates where the virus replicates predominantly in the spleen, lymph nodes and bone marrow causing hemorrhagic diathesis. Guinea pig models are well established for Junin, Machupo, and Guanarito virus diseases, and represent the best small animal model for evaluation during preclinical studies.[26,34] Guinea pigs infected with pathogenic strains of Junin virus develop a fatal disease akin to human AHF.[37]

There are many reports of the role of the transmembrane domain in the function of viral fusion proteins. In the case of influenza virus hemagglutinin, it is clear that a transmemebrane anchor is required for full fusion activity.[27] In contrast, specific sequence requirements within the trasmembrane domain have been identified, for example, in human immunodeficiency virus (HIV) type 1, murine leukemia virus, foamy viruses, coronavirus, Newcastle disease virus and measles virus.[27] Based on the drug resistant variants generated during these studies, the ST-336 class of compounds targets the GP2 envelope protein, with mutations eliciting reduced susceptibility to the drug arising in or around the transmembrane region (FIG. 4).

Drugs that target the interactions between the virus envelope and the cellular receptor represent a new class of antiviral drugs. For HIV therapy, entry inhibitors have recently raised great interest because of their activity against multi-drug resistant viruses. A new antiviral against HIV was recently approved by the FDA called enfuvirtide. Enfuvirtide (Fuzeon®) is a potent fusion inhibitor that blocks formation of the six-helix bundle and thus prevents membrane fusion.[29]

Enfuvirtide has been successful in improving the virological and immunological response in treatment-experienced HIV-infected patients.[33] There are several other compounds that counter HIV entry that are in different developmental stages, among them: 1) the attachment inhibitor dextrin-2-sulfate; 2) the inhibitors of the glycoprotein (gp) 120/CD4 interaction PRO 542, TNX 355 and BMS 488043; and 3) the co-receptor inhibitors subdivided in those targeting CCR5 or CXCR4.[20] The success of enfuvirtide and others in the development pathway are proof that virus entry inhibitors can be used to treat viral diseases in humans.

ST-294 also has the potential for prophylactic use since this drug appears to bind to the virus (FIG. 3) and would prevent infection. Other virus entry inhibitors have demonstrated protection when given prophylactically.[22]

The results presented here show that ST-294 is a potent specific inhibitor of New World arenaviruses including the Category A hemorrhagic fever viruses (Junin, Machupo, and Guanarito). More importantly, the target of ST-294 (virus entry into the cell) serves as a viable target for antiviral development. Since virus infection can be completely inhibited at concentrations in the nanomolar range, the target for ST-294 would seem to be both accessible and extremely sensitive to reagents that disrupt its role in the infection process.

Assay 3

Cytopathic Effect ("CPE") Assay

A viral CPE assay was used to evaluate the antiviral effect of Examples 100-113 against Tacaribe virus (Vero cells), Candid-1 vaccine virus (Vero cells), Amapari virus (Vero cells), SARS-CoV (Vero cells), HSV-I (Vero cells), RSV (HEp-2 cells), vaccinia virus (Vero cells), and Rotavirus (MAI 04). An enzyme-linked immunosorbent assay ("ELISA") was used to evaluate the antiviral effect of compounds against CMV (MRC-5 cells) and LCMV (Vero cells). All of these assays were carried out in the appropriate media containing 2% heat-inactivated FBS. Ninety-six-well cell culture plates were seeded 24 hours before use with $7\times10^4$ (Vero), $2.2\times10^4$ (HEp-2 and MAI 04), and $4.5\times10^4$ (MRC-5) cells per well. For compound susceptibility testing, compounds (solubilized with 100% DMSO) were added to duplicate wells at final concentrations of 50, 15.8, 5, 1.6, 0.5, 0.16, 0.05, 0.016 and 0 μM. The final concentration of DMSO in the assays was 0.5%. Virus stocks were titrated in a separate experiment to determine the concentration that resulted in 90% destruction of the cell monolayer (CPE assay) after 3 days (HSV-I, Rotavirus and vaccinia) or 7 days (SARS-CoV, RSV, Tacaribe virus, Candid 1 vaccine virus and Amapari virus) or the concentration that generated an ELISA signal of 2.5 at an optical density of 650 nm ($OD_{650}$) after 3 days (LCMV) or 4 days (CMV). These pre-established dilutions of virus were added to wells containing serial dilutions of compound. Uninfected cells and cells receiving virus without compound were included on each assay plate. In addition, reference agents, when available, were included on each assay plate (gancyclovir for HSV-I and CMV, Sigma #02536; ribavirin for LCMV and RSV, Sigma #R9644; and rifampicin for vaccinia virus, Sigma #R3501). Plates were incubated at 37° C. and 5% $CO_2$ for either 3 days (HSV-I, Rotavirus, LCMV, Vaccinia virus) or 7 days (Tacaribe virus, Amapari virus, Candid 1 virus, SARS-CoV, RSV, and CMV). HSV-1, SARS-CoV, Rotavirus, Vaccinia virus, RSV, Tacaribe virus, Amapari virus, Candid I vaccine virus infected plates were processed for crystal violet staining while plates infected with CMV and LCMV were processed for ELISA analysis. For crystal violet staining, the plates were fixed with 5% glutaraldehyde and stained with 0.1% crystal violet. After rinsing and drying, the optical density at 570 nm ($OD_{570}$) was measured using a Microplate Reader. For ELISA analysis, the medium from the LCMV and CMV-infected plates was removed and the cells were fixed with 100% methanol (Fisher, CAS #67-56-1, HPLC grade) for 20 minutes at room temperature. The methanol solution was removed and the plates were washed 3 times with PBS. Non-specific binding sites were blocked by the addition of 130 μL of Superblock Blocking Buffer (Pierce #37515) for 1 hour at 37° C. The blocking agent was removed and the wells were washed 3 times with PBS. Thirty 30 μL of a 1:20 dilution of LCMV Nuclear Protein (NP) specific monoclonal antibody (generous gift of Juan Carlos de la Torre, The Scripps Research Institute, La Jolla, Calif.) or 30 μL of a 1:200 dilution of CMV (protein 52 and unique long gene 44 product) specific cocktail monoclonal antibodies (Dako, #M0854) in Superblock Blocking Buffer containing 0.1% Tween-20 was added. Following 1 hour incubation at 37° C., the primary antibody solution was removed and the wells were washed 3 times with PBS containing 0.1% Tween-20. Forty μL of goat anti-mouse horseradish peroxidase conjugated monoclonal antibody (Bio-Rad #172-1011) diluted 1:4000 (LCMV) or 1:400 (CMV) in Superblock Blocking Buffer containing 0.1% Tween-20 was added to the wells and the plates were incubated for 1 hour at 37° C. The secondary antibody solution was removed and the wells were washed 5 times with PBS. The assay was developed for 15 minutes by the addition of 130 μL of 3,3',5,5-tetramethylbenzidine substrate (Sigma #10440) to quantify peroxidase activity. The $OD_{650}$ of the resulting reaction product was measured using a Molecular Devices Kinetic Microplate Reader with a 650 nm filter.

Antiviral activity against Tacaribe virus was evaluated by three methods: CPE Assay, Plaque Reduction, and Virus Yield Inhibition Assay. For the HTS CPE Assay, Vero cells were plated at 80% confluency on 96-well plates. Test compounds (80 per plate) from the library were added to wells at a final concentration of 5 μM. Tacaribe virus was then added at a virus dilution that would result in 90% CPE after 7 days (multiplicity of infection ("MOI") approximately 0.001). Plates were incubated at 37° C. and 5% $CO_2$ for 7 days, then fixed with 5% glutaraldehyde and stained with 0.1% crystal violet. The extent of virus CPE was quantified spectrometrically at $OD_{570}$ using an Envision Microplate Reader. The inhibitory activity of each compound was calculated by subtracting from the $OD_{570}$ of test compound well from the average $OD_{570}$ of virus infected cell wells, then dividing by the average $OD_{570}$ of mock-infected cell wells. The result represents the percent protection against Tacaribe virus CPE activity conferred by each compound. The inhibitory concentration 50% ($EC_{50}$) values were determined from a plot of the compound inhibitory activity following the CPE assay across eight compound concentrations (50, 16, 5, 1.6, 0.5, 0.16, 0.05 and 0.016 μM). AU determinations were performed in duplicate.

In the Plaque Reduction Assay, Vero cell monolayers grown in 6-well plates were infected with about 50 PFU/well in the absence or presence of various concentrations of the compounds. After 1 h of virus adsorption at 37° C. and 5% $CO_2$, residual inoculum was replaced by a 50:50 mix of 1% seaplaque agarose (in de-ionized water) and 2×MEM. Plaques were counted after 5-7 days of incubation at 37° C. The $EC_{50}$ was calculated as the compound concentration required to reduce virus plaque numbers by 50%. Under BSL 4 conditions at USAMRIID the plaque reduction assays (with Lassa, Machupo, Guanarito, and Junin viruses) were performed as follows: 200 PFU of each virus was used to infect Vero cells. After virus adsorption, cell monolayers were rinsed and overlaid with complete medium containing 1% agarose and either lacking test compound or with different concentrations ranging from 15 μM to 0.05 μM. After 5 days incubation at 37° C. and 5% $CO_2$, the monolayers were stained with neutral red and the numbers of plaques were counted.

In Virus Yield Reduction Assays, Vero cells grown in 24-well plates were infected with Tacaribe virus at a multiplicity of infection ("MOI") of 0.01 in the presence of different concentrations of the compounds, two wells per concentration. After 48 h of incubation at 37° C. virus was harvested and the virus yields were determined by plaque formation in Vero cells. The $EC_{50}$ values were calculated as indicated above and similar calculations were performed to determine $EC_{90}$ and $EC_{99}$.

Cytotoxicity Assay

Cell viability was measured by a cell proliferation assay to determine a compound's effect on cellular functions so that a 50% cytotoxicity concentration ($CC_{50}$) could be calculated; the ratio of this value to the $EC_{50}$ is referred to as the selective index (S.I.=CC50/$EC_{50}$). Three types of assays were used to determine cytotoxicity. One was a colorimetric method that measures the reduction of 3-(4,5-dimethylthiazol-2-yl)-2,5-diphenyl-tetrazolium bromide (MTT), one uses fluorimetry to measure the reduction of resazurin (Alamar Blue) and the final method uses optical density measurements of crystal violet. All three methods produced similar data. Confluent cultures in 96-well plates were exposed to different concentrations of the compounds, with two wells for each concentration, using incubation conditions equivalent to those used in the antiviral assays. For crystal violet staining, the plates were fixed with 5% glutaraldehyde and stained with 0.1% crystal violet. After rinsing and drying, the optical density at 570 nm ($OD_{570}$) was measured using a Envision Microplate Reader.

| Example Number | Tacaribe $EC_{50}$ A = <0.5 μM B = 0.5 to <1.0 μM C = 1.0 to <5 μM D = ≥5 μM | Candid 1 $EC_{50}$ A = <0.5 μM B = 0.5 to <1.0 μM C = 1.0 to <5 μM D = ≥5 μM |
|---|---|---|
| 99 | A | D |
| 100 | A | C |
| 101 | A | C |
| 102 | A | D |
| 103 | 8 | C |
| 104 | B | D |
| 105 | A | C |
| 106 | A | C |
| 107 | B | C |
| 108 | 8 | C |
| 109 | A | C |
| 110 | A | C |
| 111 | C | N/A |
| 112 | A | D |

Assay 4

Pseudotyped Antivirus Assay

Viral pseudotypes were used to demonstrate that the viral target of ST-336, described above, is the arenavirus envelope glycoprotein. This is a surrogate assay that uses only the envelope protein of the target virus, not the virus itself. Viral pseudotypes are generated by cotransfection of a replication-defective retroviral provirus containing a reporter gene, and a plasmid expressing a heterologous viral envelope. The provirus is engineered so that the homologous retroviral envelope is not expressed, and thus heterologous viral envelope proteins are acquired as budding viral particles nonspecifically capture cell surface proteins. Pseudotypes prepared in this manner will infect cells via the heterologous envelope and are commonly used to assay functions of the heterologous envelope.[40-45] Infection is measured by the signal produced from the integrated reporter construct. An env-deficient HIV provirus with a firefly luciferase reporter was used for the work described here. The amount of infectious virus used to infect a cell culture line is directly proportional, over several orders of magnitude, to the luciferase-mediated luminescence produced in the infected cells. Pseudotyped viruses containing unrelated viral envelopes, usually the VSVg protein from vesicular stomatitis virus, are used as specificity controls.

Another use of viral pseudotypes is that they allow functional analysis of an envelope outside of the context of the virus from which it was derived. Many hemorrhagic fever viruses require maximum laboratory containment (BSL-4), which impart significant logistical and safety issues. Surrogate assays can be performed under less-restrictive BSL-2 laboratory conditions, since they do not use the pathogen itself. This strategy was used to examine antiviral efficacy against hemorrhagic fever arenaviruses that normally require maximum laboratory containment, such as Machupo and Guanarito viruses.

Pseudotype virus infection is assayed in tissue culture cells, usually 293T (human embryonic kidney) or MRC-5 (human lung). Cells are seeded into 96-well plates so that they are somewhat subconfluent on the following day. In order to test the inhibitory properties of a given compound, serial compound dilutions are prepared in DMSO. Each of these dilutions is then further diluted 100-fold in cell culture media. Cell culture media is replaced with the compound dilutions in media, and then subsequently an equal volume of pseudotype virus stock is added. The pseudotype virus is diluted in cell culture media such that the amount of virus added to each well is sufficient to produce a luciferase signal providing a signal-to-noise ratio of 20 to 50. Luciferase activity is measured 2-3 days post-infection using standard luciferin-based bioluminescence detection methods, such as Promega's Luciferase Assay System. Each compound dilution is tested in triplicate wells, and luciferase activity is converted to a percentage of infectivity based on positive (no compound) and negative (no virus) controls on the same plate. Fifty percent effective concentrations ($EC_{50}$s) are calculated with IDBS XLfit4.1 software for Microsoft Excel, using a four parameter logistic model fit to $y=A+B/(1+(x/C)^D)$, where A (bottom) and B (top) are fixed at 0 and 100% respectively, C=$EC_{50}$, D=slope factor, x=compound concentration, and y=response.

| Example | $EC_{50}$ vs. pseudotyped virus (μM) A = <0.5 μM B = 0.5 to <1.0 μM C = 1.0 to <5 μM D = ≥5 μM | | | | |
|---|---|---|---|---|---|
| Number | Tacaribe | Guanarito | Machupo | Pichinde | VSV |
| 99 | A | C | B | C | D |
| 100 | A | A | A | C | D |
| 101 | A | A | A | B | D |
| 102 | A | C | A | C | D |
| 103 | A | A | A | C | D |
| 104 | A | A | A | C | D |

-continued

| Example | EC$_{50}$ vs. pseudotyped virus (μM)<br>A = <0.5 μM<br>B = 0.5 to <1.0 μM<br>C = 1.0 to <5 μM<br>D = ≥5 μM | | | | |
|---|---|---|---|---|---|
| Number | Tacaribe | Guanarito | Machupo | Pichinde | VSV |
| 105 | A | A | A | C | D |
| 106 | A | A | A | D | D |
| 107 | A | A | A | C | D |
| 108 | A | A | A | C | D |
| 109 | A | A | A | D | D |
| 110 | A | B | A | C | D |
| 111 | A | B | A | C | D |
| 112 | A | A | A | C | D |

All references cited herein are herein incorporated by reference in their entirety for all purposes.

We claim:

1. A pharmaceutical composition comprising a pharmaceutically acceptable carrier and a pharmaceutically effective amount of a compound of Formula II:

Formula II

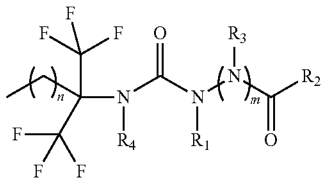

wherein, n is an integer from 0-6;

m is an integer from 0-1;

$R_1$ is selected from the group consisting of H and alkyl;

$R_2$ is selected from the group consisting of substituted or unsubstituted phenyl, substituted and unsubstituted aryl, substituted and unsubstituted heteroaryl, substituted or unsubstituted alkyl, substituted or unsubstituted branched alkyl, and substituted or unsubstituted unsaturated cycloheteroalkyls;

or where $R_1$ and $R_2$ combine together to form a substituted or unsubstituted $C_{4-10}$ cyclic saturated heteroalkyl;

$R_3$ and $R_4$ are independently selected from the group consisting of H and alkyl;

or a pharmaceutically acceptable salt thereof.

2. The pharmaceutical composition of claim 1, wherein n is 0, 1, or 2.

3. The pharmaceutical composition of claim 1, wherein n is 1.

4. The pharmaceutical composition of claim 1, wherein m is 1.

5. The pharmaceutical composition of claim 1, wherein m is 1 and n is 1.

6. The pharmaceutical composition of claim 1, wherein the compound of Formula II is selected from the group consisting of: 2-[2,5-bis(2,2,2-trifluoroethoxy)benzoyl]-N[-][1,1-bis(trifluoromethyl)propyl]hydrazinecarboxamide; N-[1,1-bis(trifluoromethyl)propyl]-2-(4-tert-butylbenzoyl)hydrazinecarboxamide; 2-(1,1'-biphenyl-4-ylcarbonyl)-N-[1,1-bis(trifluoromethyl)propyl]hydrazinecarboxamide; N-[1,1-bis (trifluoromethyl)propyl]-2-(1-naphthoyl) hydrazinecarboxamide; 2-(1,1'-biphenyl-2-ylcarbonyl)-N-[1,1-bis(trifluoromethyl)propyl]hydrazinecarboxamide; N-[1,1-bis(trifluoromethyl)propy 1]-2-(4-methylbenzoyl) hydrazinecarboxamide; N-[1,1-bis(trifluoromethyl)propyl]-2-(2-naphthoyl)drazinecarboxamide; N-[1,1-bis(trifluoromethy[l])propy[1]]-2-(2,5-d[i]methoxybenzoyl) hydrazinecarboxamide; N-[1,1-bis(trifluoromethyl)propyl]-2-(3,4-dichlorobenzoyl)hydrazinecarboxamide; N-[1,1-bis (trifluoromethyl)propy 1]-2-(4-bromobenzoyl) hydrazinecarboxamide; N-[1,1-bis(trifluoromethyl)propyl]-2-(4-isopropylbenzoyl)hydrazinecarboxamide; N-[1,1-bis (trifluoromethyl)propyl]-2-(3,5-dimethylbenzoyl) hydrazinecarboxamide; N-[1,1-bis(trifluoromethyl)propyl]-2-(mesitylcarbonyl)hydrazinecarboxamide; and N-[1,1-bis (trifluoromethyl)propyl]-2-(5-chloro-2-methoxybenzoyl) hydrazinecarboxamide.

7. The pharmaceutical composition of claim 1, wherein the compound of Formula II is N-[1,1-bis(trifluoromethyl)propyl]-2-(4-methylbenzoyl)hydrazinecarboxamide.

8. The pharmaceutical composition of claim 1, wherein the compound of Formula II is N-[1,1-bis(trifluoromethyl)propyl]-2-(2,5-dimethoxybenzoyl)hydrazinecarboxamide.

9. The pharmaceutical composition of claim 1, which further comprises cidofovir, cyclic cidofovir, or salts, esters, or prodrugs thereof.

10. A pharmaceutical composition comprising a pharmaceutically acceptable carrier and a pharmaceutically effective amount of a compound of Formula I:

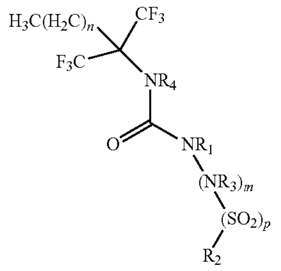

wherein n is an integer from 0-6;

m is an integer from 0-1;

p is an integer from 0-1;

$R_1$ isselected from the group consisting of H and alkyl;

$R_2$ is selected from the group consisting of substituted or unsubstituted phenyl, substituted and unsubstituted aryl, substituted and unsubstituted heteroaryl, substituted or unsubstituted alkyl, substituted or unsubstituted branched alkyl, and substituted or unsubstituted unsaturated cycloheteroalkyls; or where $R_1$ and $R_2$ combine together to form a substituted or unsubstituted $C_{4-10}$ cyclic saturated heteroalkyl;

$R_3$ is selected from the group consisting of H and alkyl;

or a pharmaceutically-acceptable salt thereof, and further comprising cidofovir, cyclic cidofovir, or salts, esters or prodrugs thereof.

* * * * *